US006200680B1

(12) United States Patent
Takeda et al.

(10) Patent No.: US 6,200,680 B1
(45) Date of Patent: Mar. 13, 2001

(54) FINE ZINC OXIDE PARTICLES, PROCESS FOR PRODUCING THE SAME, AND USE THEREOF

(75) Inventors: Mitsuo Takeda, Osaka; Tatsuhito Matsuda, Hyogo, both of (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 08/750,290

(22) PCT Filed: Jun. 6, 1995

(86) PCT No.: PCT/JP95/01113

§ 371 Date: Apr. 3, 1997

§ 102(e) Date: Apr. 3, 1997

(87) PCT Pub. No.: WO95/33688

PCT Pub. Date: Dec. 14, 1995

(30) Foreign Application Priority Data

Jun. 6, 1994 (JP) .................................................. 6/148575
Aug. 19, 1994 (JP) .................................................. 6/218066

(51) Int. Cl.⁷ .................................. B32B 5/16; C01G 9/02
(52) U.S. Cl. ........................... 428/402; 423/99; 423/111; 423/622; 423/624; 423/625; 424/401; 424/641; 424/642; 424/682; 428/403; 428/689; 428/700; 428/701; 428/702; 502/340; 502/341; 502/342; 502/343
(58) Field of Search ..................................... 428/402, 403, 428/689, 700, 701, 702; 423/99, 111, 622, 624, 625; 424/401, 641, 642, 682; 502/300, 340, 341, 342, 343

(56) References Cited

U.S. PATENT DOCUMENTS

| | | | |
|---|---|---|---|
| 4,207,377 | * | 6/1980 | Kindrick ........................... 428/404 |
| 4,331,706 | * | 5/1982 | Kindrick ........................... 427/74 |
| 5,093,099 | * | 3/1992 | Haishi et al. ..................... 423/622 |
| 5,306,522 | * | 4/1994 | Clough et al. ................. 427/126.3 |
| 5,407,743 | * | 4/1995 | Clough et al. ................... 428/357 |
| 5,750,609 | * | 5/1998 | Nosu et al. ...................... 524/413 |
| 6,086,666 | * | 7/2000 | Noguchi et al. ................. 106/425 |
| 6,099,695 | * | 8/2000 | Fujishima et al. ........... 204/157.44 |

FOREIGN PATENT DOCUMENTS

| | | |
|---|---|---|
| B1-46-16668 | 5/1971 | (JP) . |
| B2-55-19896 | 5/1980 | (JP) . |
| 56-74172 | 6/1981 | (JP) . |
| 61-86421 | 5/1986 | (JP) . |
| 63-277686 | 11/1988 | (JP) . |
| 4-357114 | 12/1992 | (JP) . |
| 7-165422 | 6/1995 | (JP) . |

* cited by examiner

Primary Examiner—H. Thi Le
(74) Attorney, Agent, or Firm—Pendorf & Cutliff

(57) ABSTRACT

A process for producing zinc oxide fine particles comprising heating a mixture comprising a zinc source, a carboxyl-containing compound, and an alcohol; a process for producing zinc oxide-polymer composite particles, which comprises heating a mixture comprising a zinc source, a carboxyl-containing compound, a polymer, and an alcohol at a temperature of 100° C. or higher; a process for producing inorganic compound particles having on their surface a cluster of thin plate like zinc oxide crystals with their tip projecting outward, which comprises heating a mixture comprising a zinc source, a carboxyl-containing compound, lactic acid or a compound thereof, and an alcohol at a temperature of 100° C. or higher; a process for producing zinc oxide-based particles comprising heating a mixture comprising a zinc source, a carboxyl-containing compound, at least one element additive selected from the group consisting of the group IIIB metal elements and the group IVB metal elements, and an alcohol at a temperature of 100° C. or higher; zinc oxide-based fine particles obtained by these processes; and uses of the zinc oxide-based fine particles.

21 Claims, 12 Drawing Sheets

15 μm

1 μm 20 nm

15 μm 860 nm

FINE ZINC OXIDE PARTICLES, PROCESS FOR PRODUCING THE SAME, AND USE THEREOF

TECHNICAL FIELD

This invention relates to a process for producing zinc oxide-based fine particles which are useful as a raw material or an additive for rubber vulcanization accelerators, various coatings, printing inks, colors, glass, catalysts, medicines, pigments, ferrite, etc. and can also be made use of in electrophotographic photoreceptors, printing materials, platemaking materials, UV screens, UV absorbing materials, gas sensors, etc. It also relates to a process for producing zinc oxide-based fine particles which are useful as such an additive that has high light-transmitting properties in the visible region and high UV absorbing properties, i.e., a so-called transparent UV absorber in coating materials, varnishes, resins, paper, cosmetics, and the like.

The present invention relates to zinc oxide-based fine particles having high transparency in the visible region, excellent UV absorbing properties, and heat ray screening properties as well as the above-mentioned functions and uses, which are useful as a so-called transparent UV and heat ray screening agent, an electrically conducting agent or an antistatic agent that in coatings (e.g., coating agent, ink, etc.), resins, paper, cosmetics, etc.; a process for producing the same; and products containing the same, i.e., coatings, coated articles, resin compositions, resin molded articles, cosmetics, and paper.

The present invention relates to zinc oxide-based fine particles which have a unique higher-order structure in which the constituent primary particles (zinc oxide crystals) have a controlled size and therefore exhibit high light transmitting properties combined with excellent scattering properties in the visible region, that is, excellent diffuse transmission properties in addition to the above-described functions and uses. The fine particles are therefore useful as a light diffusing agent. The invention also relates to a process for producing such zinc oxide-based particles and products containing the same, such as coatings (e.g., coating agent, ink, etc.), coated articles, resin compositions, resin molded articles, cosmetics, and paper, typified by a medium for diffuse transmission, such as a diffuser film for back-lighting liquid crystal displays.

The present invention relates to zinc oxide-based fine particles which not only have the above-described functions and uses but have controlled crystal morphology and a unique agglomerated state (higher-order structure) and are therefore also excellent in antimicrobial properties and deodorizing properties; a process for producing the same; and products containing the same, such as coatings (e.g., coating agent, ink, etc.), coated articles, resin compositions, resin molded articles, cosmetics, and paper.

BACKGROUND ART

Zinc oxide fine particles, what we call zinc white, have been conventionally produced by (1) a method consisting of gas phase oxidation of zinc vapor (called a France process or a American process) or (2) a method comprising reacting a zinc salt and an alkali metal carbonate in an aqueous solution to obtain zinc carbonate powder and, after washing with water and drying, pyrolyzing the powder in air. Zinc oxide obtained by the method (1) appears to have a particle size of submicron order but undergoes strong secondary agglomeration during the production process. Dispersing the particles in coating compositions or resin compositions requires much mechanical labor and yet results in a failure of obtaining a homogeneous dispersion. Compared with the method (1), the method (2) provides such finer particles as have a primary particle size of 0.1 μm or smaller, but the effects expected from the fineness are not manifested sufficiently on account of the strong agglomerating force among primary particles. Under the present situation, it is still less achievable with these methods to obtain zinc oxide fine particles with strictly controlled morphology, such as particle size, shape and surface condition of the primary particles, and the state of dispersion or agglomeration, in agreement with the end use.

In recent years, development of zinc oxide-based fine particles practically having a particle size of not greater than 0.1 μm has been demanded for use as a weatherable and heat-resistant material which is highly transparent in the visible region and also capable of absorbing ultraviolet light, i.e., a so-called transparent UV absorber. Processes hitherto proposed for producing such fine particles include (3) a method comprising gas phase oxidation of zinc vapor and (4) a wet process, such as a process comprising hydrolysis of a zinc salt in an alkali aqueous solution (see JP-A-4-164813 and JP-A-4-357114, the term "JP-A" as used herein means an "unexamined published Japanese patent application") and a process in which a mixed solution of an acidic salt of zinc and ammonium acetate and hydrogen sulfide are subjected to autoclaving to form zinc sulfide, which is then subjected to oxidation (see JP-A-2-311314). The fine particles as obtained by the method (3) are powder having undergone firm secondary agglomeration as stated above and, when added to plastic moldings, such as fiber, a plate or a film, or coatings for the purpose of imparting UV absorptivity or improving weatherability, fail to provide products having satisfactory transparency. Further, when the fine particles are dispersed in an appropriate solvent and, if necessary, mixed with a binder resin to prepare a coating agent, and the coating agent is applied to a transparent substrate, such as glass or a plastic film, for the purpose of imparting UV absorptivity, the resulting coating film has poor transparency and homogeneity. On the other hand, the wet processes (4) involve complicated steps and unavoidably incur high cost. Thus, a process for producing zinc oxide-based fine particles which manifest the functions and characteristics of fine particles to the full extent and still have general-purpose properties is unknown.

Since zinc oxide fine particles have excellent UV screening power (in absorbing or scattering), they are used in coating films or resin molded articles endowed with UV screening power. However, zinc oxide fine particles have low dispersibility due to their liability to agglomeration.

Light-diffusing compositions comprising transparent inorganic fine particles, e.g., calcium carbonate, silica or barium sulfate, as dispersed in a binder component capable of dispersing such fine particles (e.g., methacrylic resins) are known. The light-diffusing compositions are used as a coating composition to be applied to a transparent substrate to form a light-diffusing layer or as a molding material to be molded into a molded article having light-diffusing properties, to provide a diffuser. The diffusing properties of these diffusers are based on light scattering at the interface between the inorganic transparent fine particles and the binder component due to the difference in refractive index therebetween.

However, the inorganic transparent particles of calcium carbonate, silica, barium sulfate, and the like do not have a UV screening function. Further, these diffusers essentially have poor mechanical characteristics on account of low affinity between the inorganic transparent particles and the binder component. Furthermore, since the diffusers should contain a large quantity of the inorganic transparent particles for achieving high diffusing properties, they have a reduced percent transmission and further reduced mechanical characteristics.

There has recently been an increasing demand for antistatic treatment on glass products or plastic products (films and fibers) for use as window panes of a clean room, CRT screens, flooring, wall covering, clothing, and the like for the purpose of preventing adhesion of dust.

An insulator, such as resin, can be made electrically conductive by, for example, dispersing a conducting agent in resin or applying a coating composition having dispersed therein a conducting agent on a substrate to form an electrically conductive layer. Known conducting agents include fine particles of metals, e.g., nickel (Ni), copper (Cu) or aluminum (Al); fine particles of metal oxides, such as those obtained by reducing metal oxides represented by titanium black, and electrically conducting white metal oxides activated with different elements (e.g., tin oxide-based particles, indium oxide-based particles, and zinc oxide-based particles); carbonaceous fine particles of carbon black, graphite, etc.; and organic conducting agents represented by nonionic, anionic, cationic or amphoteric surface active agents.

Of these conducting agents, organic ones, whose conductivity-imparting action is based on ionic conduction and therefore dependent on humidity, unsuccessfully work at a low humidity. Besides, those having a low molecular weight bleed out with time and undergo deterioration in performance.

To the contrary, metallic, metal oxide type, or carbonaceous conducting agents, whose action is based on electron conduction, are substantially independent on humidity. Although superior to organic ones in this point, the metal oxide conducting agents obtained by reduction of titanium black, etc. and the carbonaceous conducting agents assume a black or nearly black color, and the metallic conducting agents reflect visible light strongly. Therefore, it is extremely difficult to retain the transparency of the substrate or matrix, and the application of these conducting agents is so limited.

On the other hand, it is known that a coating film formed of ink or a coating composition having dispersed therein such white conducting particles as antimony-doped tin oxide and tin-doped indium oxide or a film formed of a resin composition having dispersed therein these particles successfully impart conductivity for producing antistatic effect without impairing the hue of the substrate or the matrix. A film formed of these oxides by gas phase film formation, such as sputtering, has high electrical conductivity and has been used as a transparent electrode of flat displays, such as liquid crystal displays and electroluminescence displays, an electrode for touch panels of word processors, electronic game equipment, etc., and an antistatic film. However, because the raw materials of tin oxide- or indium oxide-based particles are very expensive, and gas phase film formation requires expensive equipment, this technique does not seem applicable generally.

In recent times, a material has been demanded, which can be applied to or incorporated into glass products, such as window panes, or resin products, such as polyester or (meth)acrylic films or sheets, without impairing the transparency or hue of the substrate or matrix and effectively shield these products from ultraviolet rays, inclusive of UV-B (280 to 320 nm) and UV-A (320 to 400 nm), and heat rays.

Conventional materials known for their UV screening effect include organic UV absorbers, such as benzotriazole compounds and benzophenone compounds, and inorganic UV absorbers, such as titanium oxide, zinc oxide, and cerium oxide. However, none of them has a heat ray screening effect.

Known heat ray screens include organic dyes having absorptivity in the infrared region, such as anthraquinone type, polymethine type, cyanine type, aluminum type or diimonium type dyes, and the aforementioned tin oxide- or indium oxide-based conducting particles, but none of them screens out ultraviolet rays effectively.

It is known that fine particles of mica coated with a titanium oxide thin film absorb ultraviolet light owing to the titanium oxide coat and, having a multi-layer structure, scatter electromagnetic waves in the heat ray region to some extent. However, the particles have insufficient visible light transmitting properties and are not deemed to fit the above-described needs.

Considering a combined use of a UV screen and a heat ray screen, there are disadvantages such that the organic dye (heat ray screen) shows absorptions in the visible light and unavoidably causes coloring; the heat ray absorption range of the organic dye is narrow; and the tin oxide- or indium oxide-based particles are expensive and economically disadvantageous as stated above.

Zinc oxide effectively absorbs both A and B waves of ultraviolet light and shows no selective absorption in the visible region. Therefore, a thin film having highly dispersed therein ultrafine particles of zinc oxide or a homogeneous zinc oxide thin film obtained by gas phase film formation serves as a transparent UV absorbing film. Doping of zinc oxide with a trivalent or tetravalent metal element gives zinc oxide electrical conductivity and, in some cases, heat ray screening properties.

However, as stated above, a process for producing zinc oxide fine particles which can manifest the functions and characteristics of fine particles to the full extent and still have general-purpose properties is unknown. Besides, all the zinc oxide fine particles so far obtained by conventional processes have UV absorbing properties but cannot screen out (near) infrared rays.

On the other hand, it is known that a zinc oxide film comprising zinc oxide doped with aluminum (Al) which is obtained by gas phase film formation exhibits high electrical conductivity and heat ray screening power (see Minami Uchitsugu, *Ohyo Butsuri* (Applied Physics), Vol. 61, No. 12 (1992)). It has been suggested that a solid solution of silicon (Si), germanium (Ge), zirconium (Zr), etc. in zinc oxide (JP-B-5-6766, the term "JP-B" as used herein means an "examined published Japanese patent application"), a solid solution of the group IIIB element, e.g., boron (B), scandium (Sc), yttrium (Y), indium (In), thallium (Tl), etc., in zinc oxide (JP-B-3-72011) or a solid solution of aluminum (Al) in zinc oxide (JP-B-4-929) can provide a transparent zinc oxide film excellent in conductivity and infrared reflecting properties. However, any of the techniques disclosed consists of gas phase film formation and cannot be a general-purpose process.

It is also known that an electrically conductive zinc oxide film can be obtained by a method for forming a zinc oxide thin film making use of pyrolysis of a zinc salt, in which the film is finally subjected to high temperature in a reducing atmosphere, or a dopant is previously added to a zinc salt solution and a resulting film is finally subjected to high temperature, as disclosed in JP-A-1-301515. This method still fails to provide heat ray screening properties.

Additional methods which are generally known for making zinc oxide powder electrically conductive include a method comprising calcining zinc oxide powder at a high temperature in a reducing atmosphere and a method comprising calcining zinc oxide powder mixed with a dopant, e.g., aluminum oxide, at a high temperature in a reducing atmosphere. The degree of conductivity attained by the former method is limited. In either method, because the particles are exposed to high temperature, fine particles, especially ultrafine particles of 0.1 µm or smaller cannot be obtained.

A transparent conducting film-forming composition containing conductive zinc oxide fine powder prepared by a specific process is known (JP-A-1-153769), in which the conductive zinc oxide fine powder is aluminum-activated powder having a specific surface area diameter of not greater than 0.1 µm and a volume resistivity of not higher than $10^4$ Ωcm under a specific pressure condition. However, since the preparation of the zinc oxide powder involves calcination at a high temperature, the powder, even having a specific surface area diameter of not greater than 0.1 µm, becomes larger as dispersed in the composition. It is assumed that the film obtained by application of the coating composition would have limited transparency. Heat ray screening properties of the film according to this technique are unknown.

Fine and thin particles of inorganic compounds having a tabular form, a flaky form and the like include titanium oxide fine particles (JP-A-58-88121), titanium oxide-coated mica (JP-B-31-9355, JP-B-33-294, and JP-A-2-173060), and zinc oxide fine flakes (JP-B-55-25133 and JP-A-6-80421).

These inorganic compound fine particles are added to resin compositions forming film, fiber or plates; coating compositions to be applied to film, fiber, resin plates, glass, paper, etc.; paper; cosmetics; and the like for the purpose of adding value to these products.

Inorganic compound fine particles which are added to resin compositions forming film, fiber or plates; coating compositions to be applied to film, fiber, resin plates, glass, paper, etc.; paper; cosmetics; and the like for the purpose of improving appearance, energy saving, and improving comfort of household goods in conformity with an advanced style of life are required to have:

(1) an attractive appearance brought about by designing to the effect that a tone changes with a change in viewing angle or angle of light incidence and also by transparency; and (2) a function of efficiently cutting heat rays, particularly near infrared rays, in seeking energy saving and comfort.

For protection of the body, particularly hair, eyes and the skin and for prevention of deterioration of resin products, the inorganic compound fine particles possessing the above characteristics (1) and (2) are additionally required to have (3) a function of efficiently cutting ultraviolet rays which are contained in sunlight or electromagnetic waves emitted from fluorescent tubes and cause harm to the body and deterioration in resin products. UV screens comprising inorganic compound fine particles are superior to organic UV absorbers in terms of toxicity, heat resistance, and stability with time. From this viewpoint, $TiO_2$ or ZnO has been made into ultrafine particles or thin particles for use for transparency improvement.

Ultrafine or thin titanium oxide particles do not possess the above-described effects of design, though having a UV cutting effect and higher visible light transmitting properties than titanium white that is a white pigment.

Although titanium oxide-coated mica is capable of preventing transmission of heat rays and ultraviolet rays, they have a pearly luster, lacking transparency, and is therefore inferior in terms of the above-mentioned attractiveness of appearance.

Ultrafine or thin plate like zinc oxide particles have transparency to visible light and, as compared with titanium oxide fine particles, cut ultraviolet rays over a longer wavelength side, and retain the UV cutting effect over an extended time period. However, zinc oxide fine particles do not possess the above-described effect of design and transmit heat rays.

An object of the present invention is to provide a highly productive process for producing zinc oxide fine particles with their size, shape and surface conditions controlled and also with the degree of dispersion and agglomeration controlled, which comprises heating a mixture of zinc or a compound thereof, a carboxyl-containing compound, and an alcohol.

Another object of the invention is to provide an industrial process for producing zinc oxide fine particles which can manifest the functions and characteristics of fine particles having excellent transparency to the full extent in practical use.

Still another object of the invention is to provide zinc oxide-polymer composite particles which exhibit UV screening power, controlled visible light transmitting properties combined with controlled light diffusing properties, and excellent dispersibility.

Yet another object of the invention is to provide a process for producing such zinc oxide-polymer composite particles with satisfactory productivity.

A further object of the invention is to provide inorganic compound particles which show abnormal light transmitting properties ascribed to their unique geometrical characteristics not heretofore attained.

A still further object of the invention is to provide a process for producing such inorganic compound particles with satisfactory productivity.

A yet further object of the invention is to provide zinc oxide-based particles which comprise zinc oxide having excellent UV screening properties as a base to which heat ray screening properties and electrical conductivity are imparted, and which are easily made transparent.

A yet another object of the invention is to provide a process for producing such zinc oxide-based particles with high productivity.

A yet another object of the invention is to provide coating compositions, coated articles, resin compositions, resin molded articles, paper, and cosmetics which contain the above-described zinc oxide fine particles, zinc oxide-polymer composite particles, inorganic compound particles or zinc oxide-based particles so that the characteristics possesses by these particles may be taken advantage of.

DISCLOSURE OF THE INVENTION

The inventors of the present invention have conducted extensive investigations in order to accomplish the above objects and, as a result, reached the invention.

The invention embraces the following embodiments.

(1) A process for producing zinc oxide fine particles comprising heating a mixture comprising a zinc source, a carboxyl-containing compound, and an alcohol.

(2) A process for producing zinc oxide fine particles as described in (1), which comprises a first mixing step of preparing a first mixture comprising a zinc source and a carboxyl-containing compound and a second mixing step of mixing the first mixture with a heated alcohol-containing solution.

(3) A process for producing zinc oxide fine particles as described in (2), wherein the second mixing step is a step of adding the first mixture to an alcohol-containing solution maintained at 100° C. or above and mixing them.

(4) A process for producing zinc oxide fine particles as described in any of (1) to (3), wherein the process comprises a first mixing step of preparing a first mixture comprising a zinc source and a carboxyl-containing compound, a second mixing step of mixing the first mixture maintained at 60° C. or above with an alcohol-containing solution maintained at 100° C. or above to obtain a second mixture, and a step of heating the second mixture.

(5) A process for producing zinc oxide fine particles as described in any of (1) to (4), wherein the resulting zinc oxide fine particles have an average primary particle size ranging from 0.005 to 10 $\mu$m.

(6) A process for producing zinc oxide fine particles as described in any of (1) to (5), wherein the zinc source is selected from the group consisting of zinc oxide, zinc hydroxide, and zinc acetate.

(7) A process for producing zinc oxide fine particles as described in any of (1) to (6), wherein the carboxyl-containing compound comprises a saturated fatty acid having a boiling point of 200° C. or lower at atmospheric pressure.

(8) A process for producing zinc oxide fine particles as described in any of (4) to (7), wherein the second mixing step and/or the heating step is/are carried out in the presence of a compound additive containing one or more than one atomic group of at least one kind selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group in the molecule thereof and having a molecular weight of less than 1,000.

(9) A process for producing zinc oxide fine particles as described in any of (4) to (8), wherein the second mixing step or the heating step is carried out in the presence of carbon dioxide and/or a carbonic acid source.

(10) A process for producing zinc oxide-polymer composite particles, which comprises heating a mixture comprising a zinc source, a carboxyl-containing compound, a polymer, and an alcohol at a temperature of 100° C. or higher.

(11) A process for producing zinc oxide-polymer composite particles as described in (10), wherein the process comprises a first mixing step of preparing a first mixture comprising a zinc source and a carboxyl-containing compound and a second mixing step of mixing the first mixture with a heated alcohol-containing solution, and the polymer is added in at least one step selected from the first mixing step and the second mixing step.

(12) A process for producing zinc oxide-polymer composite particles as described in (10) or (11), wherein the process comprises a first mixing step of preparing a first mixture comprising a zinc source and a carboxyl-containing compound, a second mixing step of mixing the first mixture maintained at 60° C. or above with an alcohol-containing solution maintained at 100° C. or above to obtain a second mixture, and a step of heating the second mixture, and the polymer is added in at least one step selected from the first mixing step, the second mixing step, and the heating step.

(13) A process for producing zinc oxide-polymer composite particles as described in (11), wherein the first mixing step is a step of dissolving the zinc source in a mixed solvent of the carboxyl-containing compound and water.

(14) A process for producing zinc oxide-polymer composite particles as described in any of (10) to (13), wherein the polymer contains at least one polar atomic group.

(15) A process for producing zinc oxide-polymer composite particles as described in (14), wherein the atomic group is at least one member selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group.

(16) A process for producing zinc oxide-polymer composite particles as described in any of (10) to (15), wherein the zinc source is selected from the group consisting of zinc oxide, zinc hydroxide, and zinc acetate.

(17) A process for producing zinc oxide-polymer composite particles as described in any of (10) to (16), wherein the carboxyl-containing compound comprises a saturated fatty acid having a boiling point of 200° C. or lower at atmospheric pressure.

(18) A process for producing zinc oxide-polymer composite particles as described in any of (10) to (17), wherein the polymer is used at a weight ratio of 0.01 to 1.0 to the zinc atoms, in terms of zinc oxide, present in the zinc source.

(19) A process for producing inorganic compound particles having on their surface a cluster of thin plate like zinc oxide crystals with their tip projecting outward, which comprises heating a mixture comprising a zinc source, a carboxyl-containing compound, lactic acid or a compound thereof, and an alcohol at a temperature of 100° C. or higher.

(20) A process for producing inorganic compound particles as described in (19), wherein the process comprises a first mixing step of preparing a first mixture comprising a zinc source and a carboxyl-containing compound and a second mixing step of mixing the first mixture with a heated alcohol-containing solution, and the lactic acid or a compound thereof is added in at least one step selected from the first mixing step and the second mixing step.

(21) A process for producing inorganic compound particles described in (19), wherein the process comprises a first mixing step of preparing a first mixture comprising a zinc source and a carboxyl-containing compound, a second mixing step of mixing the first mixture maintained at 60° C. or above with an alcohol-containing solution maintained at 100° C. or above to obtain a second mixture, and a heating step of heating the second mixture, and the lactic acid or a compound thereof is added in at least one step selected from the first mixing step, the second mixing step, and the heating step.

(22) A process for producing inorganic compound particles as described in (21), wherein the first mixing step is a step of dissolving the zinc source in a mixed solvent of the carboxyl-containing compound and water.

(23) A process for producing inorganic compound particles as described in any of (19) to (22), wherein the lactic acid or a compound thereof is at least one compound selected from the group consisting of lactic acid, a lactic acid metal salt, and a lactic ester.

(24) A process for producing inorganic compound particles as described in any of (19) to (23), wherein the zinc source is selected from the group consisting of zinc oxide, zinc hydroxide, and zinc acetate.

(25) A process for producing inorganic compound particles as described in any of (19) to (24), wherein the carboxyl-containing compound comprises a saturated fatty acid having a boiling point of 200° C. or lower at atmospheric pressure.

(26) A process for producing inorganic compound particles as described in any of (20) to (25), wherein the lactic acid or a compound thereof is used at a lactic acid to zinc molar ratio of 0.001 to 0.4.

(27) A process for producing zinc oxide-based particles comprising heating a mixture comprising a zinc source, a carboxyl-containing compound, at least one element additive selected from the group consisting of the group IIIB metal elements and the group IVB metal elements, and an alcohol at a temperature of 100° C. or higher.

(28) A process for producing zinc oxide-based particles as described in (27), wherein the process comprises a first mixing step of preparing a first mixture comprising a zinc source and a carboxyl-containing compound and a second mixing step of mixing the first mixture with a heated alcohol-containing solution, and the element additive is added in at least one step selected from the first mixing step and the second mixing step.

(29) A process for producing zinc oxide-based particles as described in (27) or (28), wherein the process comprises a first mixing step of preparing a first mixture comprising a zinc source and a carboxyl-containing compound, a second mixing step of mixing the first mixture maintained at 60° C. or above with an alcohol-containing solution maintained at 100° C. or above to obtain a second mixture, and a heating step of heating the second mixture, and the element additive is added in at least one step selected from the first mixing step, the second mixing step, and the heating step.

(30) A process for producing zinc oxide-based particles as described in any of (27) to (29), wherein the group IIIB metal element is indium and/or aluminum.

(31) A process for producing zinc oxide-based particles as described in any of (27) to (30), wherein the zinc source is selected from the group consisting of zinc oxide, zinc hydroxide, and zinc acetate.

(32) A process for producing zinc oxide-based particles as described in any of (27) to (31), wherein the carboxyl-containing compound comprises a saturated fatty acid having a boiling point of 200° C. or lower at atmospheric pressure.

(33) A process for producing zinc oxide-based particles as described in any of (28) to (32), wherein any of the steps is conducted in the presence of lactic acid or a compound thereof.

(34) A process for producing zinc oxide-based particles as described in any of (28) to (32), wherein any of the steps is conducted in the presence of a polymer.

(35) A process for producing zinc oxide-based particles as described in any of (29) to (32), wherein the second mixing step and/or the heating step is/are carried out in the presence of a compound additive containing one or more than one atomic group of at least one kind selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group in the molecule thereof and having a molecular weight of less than 1,000.

(36) A process for producing zinc oxide-based particles as described in any of (29) to (32), wherein the second mixing step or the heating step is carried out in the presence of carbon dioxide and/or a carbonic acid source.

(37) Zinc oxide-polymer composite particles which comprise zinc oxide fine particles and a polymer, the proportion of the zinc oxide fine particles being 50 to 99% by weight based on the total weight of the zinc oxide fine particles and the polymer, and the composite particles having an outer shell composed of a mixture and/or a composite of the zinc oxide fine particles and the polymer with the inside of the outer shell being hollow.

(38) Zinc oxide-polymer composite particles as described in (37), wherein the composite particles have a number average particle size of 0.1 to 10 μm with a coefficient of particle size variation being not more than 30%.

(39) Zinc oxide-polymer composite particles as described in (38), wherein the zinc oxide fine particles have a number average particle size of 0.005 to 0.1 μm, the ratio of the number average particle size of the zinc oxide fine particles to the number average particle size of the zinc oxide-polymer composite particles being 1/10 to 1/1,000.

(40) Zinc oxide-polymer composite particles as described in any of (37) to (39), wherein the composite particles have a spherical shape and/or an ellipsoidal shape.

(41) Zinc oxide-polymer composite particles as described in any of (37) to (40), wherein the polymer contains at least one polar atomic group.

(42) Zinc oxide-polymer composite particles as described in (41), wherein the atomic group is at least one member selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group.

(43) Inorganic compound particles containing 60 to 100% by weight of zinc oxide and having on their surface a cluster of thin plate like zinc oxide crystals with their tip projecting outward.

(44) Inorganic compound particles as described in (43), wherein the particles have a major axis/minor axis ratio of 1.0 to 5.0.

(45) Inorganic compound particles as described in (43) or (44), wherein the particles have a number average particle size of 0.1 to 10 μm with a coefficient of particle size variation being not more than 30%.

(46) Inorganic compound particles as described in (43) to (45), wherein the particles are hollow.

(47) Inorganic compound particles as described in (43) to (45), wherein the particles are porous.

(48) Inorganic compound particles as described in any of (43) to (46), wherein the thin plate like zinc oxide crystals are thin plates having a flatness of 2 to 200.

(49) Inorganic compound particles as described in (48), wherein the thin plates have a major axis of 5 to 1,000 nm.

(50) Zinc oxide-based particles comprising a metal oxide co-precipitate containing, as a metallic component, at least one element additive selected from the group consisting of the group IIIB metal elements and the group IVB metal elements and zinc, having a zinc content of 80 to 99.9% in terms of the ratio of the number of zinc atoms to the total number of the atoms of the metallic components, and having X-ray crystallographically exhibiting zinc oxide crystalline properties.

(51) Zinc oxide-based particles as described in (50), wherein the element additive is indium and/or aluminum.

(52) Zinc oxide-based particles as described in (50) or (51), wherein the particles consist of single particles of the metal oxide co-precipitate.

(53) Zinc oxide-based particles in which the single particles described in (52) form composite particles with a polymer.

(54) Zinc oxide-based particles as described in (52) or (53), wherein the particles have an average shortest diameter of 0.001 to 0.1 μm.

(55) Zinc oxide-based particles which are secondary particles formed by agglomeration of primary particles, the primary particles being the single particles described in any of (52) to (54) which constitute the zinc oxide-based particles.
(56) Zinc oxide-based particles as described in (55), wherein the secondary particles are hollow particles made up solely of an outer shell.
(57) Zinc oxide-based particles as described in (55) or (56), wherein the particles are hollow particles made up solely of an outer shell composed of the single particles and the polymer.
(58) Zinc oxide-based particles as described in any of (55) to (57), wherein the particles have an average particle size ranging from 0.001 to 10 µm.
(59) A coating composition comprising zinc oxide fine particles produced by the process described in any of (1) to (9) and a binder component capable of forming a coating film binding the zinc oxide fine particles, the proportion of the zinc oxide fine particles being 0.1 to 99% by weight and the proportion of the binder component being 1 to 99.9% by weight each based on the total solids content of the zinc oxide fine particles and the binder component.
(60) A coated article comprising at least one substrate selected from the group consisting of a resin molded article, glass and paper and a coating film provided on the substrate which is formed of the coating composition described in (59).
(61) A resin composition comprising the zinc oxide fine particles produced by the process described in any of (1) to (9) and a resin capable of forming a continuous phase having dispersed therein the zinc oxide fine particles, the proportion of the zinc oxide fine particles being 0.1 to 99% by weight and the proportion of the resin being 1 to 99.9% by weight each based on the total solids content of the zinc oxide fine particles and the resin.
(62) A resin molded article obtained by molding the resin composition described in (61) into at least one shape selected from the group consisting of a plate, a sheet, a film, and fiber.
(63) Paper comprising pulp made into paper and having dispersed therein the zinc oxide fine particles produced by the process described in any of (1) to (9), the proportion of the zinc oxide fine particles being 0.01 to 50% by weight based on the pulp.
(64) A cosmetic containing 0.1% by weight or more of the zinc oxide fine particles produced by the process described in any of (1) to (9).
(65) A coating composition comprising the zinc oxide-polymer composite particles described in any of (37) to (42), a binder component capable of forming a transparent or semitransparent continuous phase, and a solvent capable of dispersing the composite particles and capable of dispersing and/or dissolving the binder component.
(66) A coating composition comprising zinc oxide-polymer composite particles produced by the process described in any of (10) to (18), a binder component capable of forming a transparent or semitransparent continuous phase, and a solvent capable of dispersing the composite particles and capable of dispersing and/or dissolving the binder component.
(67) A coated article comprising a transparent or semitransparent substrate and a coating film provided on the surface of the substrate which is formed of the coating composition described in (65) or (66).
(68) A resin composition comprising the zinc oxide-polymer composite particles described in any of (37) to (42) and a resin capable of forming a transparent or semitransparent continuous phase.
(69) A resin composition comprising the zinc oxide-polymer composite particles produced by the process described in any of (10) to (18) and a resin capable of forming a transparent or semitransparent continuous phase.
(70) A resin molded article obtained by molding the resin composition described in (68) or (69) into at least one shape selected from the group consisting of a plate, a sheet, a film, and fiber.
(71) Paper comprising pulp made into paper and having dispersed therein zinc oxide-polymer composite particles described in any of (37) to (42), the proportion of the composite particles being 0.01 to 50% by weight based on the pulp.
(72) Paper comprising pulp made into paper and having dispersed therein the zinc oxide-polymer composite particles produced by the process described in any of (10) to (18), the proportion of the composite particles being 0.01 to 50% by weight based on the pulp.
(73) A cosmetic containing 0.1% by weight or more of the zinc oxide-polymer composite particles described in any of (37) to (42).
(74) A cosmetic containing 0.1% by weight or more of the zinc oxide-polymer composite particles produced by the process described in any of (10) to (18).
(75) A diffuser for back-lighting a liquid crystal display, which has a resin layer containing the zinc oxide-polymer composite particles described in any of (37) to (42).
(76) A diffuser for back-lighting a liquid crystal display, which has a resin layer containing the zinc oxide-polymer composite particles produced by the process described in any of (10) to (18).
(77) A diffuser for back-lighting a liquid crystal display, which has a resin layer containing the zinc oxide-based particles produced by the process described in any of (27) to (36).
(78) A diffuser for back-lighting a liquid crystal display, which has a resin layer containing the zinc oxide-based particles described in any of (50) to (58).
(79) A coating composition comprising the zinc oxide-based particles described in any of (50) to (58) and a binder component capable of forming a coating film binding the zinc oxide-based particles, the proportion of the zinc oxide-based particles being 0.1 to 99% by weight and the proportion of the binder component being 1 to 99.9% by weight each based on the total solids content of the zinc oxide-based particles and the binder component.
(80) A coated article comprising at least one substrate selected from the group consisting of a resin molded article, glass and paper and a coating film provided on the substrate which is formed of the coating composition described in (79).
(81) A resin composition comprising the zinc oxide-based particles described in any of (50) to (58) and a resin capable of forming a continuous phase having dispersed therein the zinc oxide-based particles, the proportion of the zinc oxide-based particles being 0.1 to 99% by weight and the proportion of the resin being 1 to 99.9% by weight each based on the total solids content of the zinc oxide-based particles and the resin.
(82) A resin molded article obtained by molding the resin composition described in (81) into at least one shape selected from the group consisting of a plate, a sheet, a film, and fiber.
(83) Paper comprising pulp made into paper and having dispersed therein the zinc oxide-based particles described in any of (50) to (58), the proportion of the zinc oxide-based particles being 0.01 to 50% by weight based on the pulp.

(84) A cosmetic containing 0.1% by weight or more of the zinc oxide-based particles process described in any of (50) to (58).

(85) A coating composition comprising the inorganic compound particles described in any of (43) to (49) and a binder component capable of forming a coating film binding the inorganic compound particles, the proportion of the inorganic compound particles being 0.1 to 99% by weight and the proportion of the binder component being 1 to 99.9% by weight each based on the total solids content of the inorganic compound particles and the binder component.

(86) A coated article comprising at least one substrate selected from the group consisting of a resin molded article, glass and paper and a coating film provided on the substrate which is formed of the coating composition described in (85).

(87) A resin composition comprising the inorganic compound particles described in any of (43) to (49) and a resin capable of forming a continuous phase having dispersed therein the inorganic compound particles, the proportion of the inorganic compound particles being 0.1 to 99% by weight and the proportion of the resin being 1 to 99.9% by weight each based on the total solids content of the inorganic compound particles and the resin.

(88) A resin molded article obtained by molding the resin composition described in (87) into at least one shape selected from the group consisting of a plate, a sheet, a film, and fiber.

(89) Paper comprising pulp made into paper and having dispersed therein the inorganic compound particles described in any of (43) to (49), the proportion of the inorganic compound particles being 0.01 to 50% by weight based on the pulp.

(90) A cosmetic containing 0.1% by weight or more of the inorganic compound particles described in any of (43) to (49).

(91) An antimicrobial agent comprising the inorganic compound particles described in any of (43) to (49).

(92) A controlled releasing agent comprising the inorganic compound particles described in any of (43) to (49).

(93) An adsorbent comprising the inorganic compound particles described in any of (43) to (49).

(94) A coating composition comprising the zinc oxide-based particles produced by the process described in any of (27) to (36) and a binder component capable of forming a coating film binding the zinc oxide-based particles, the proportion of the zinc oxide-based particles being 0.1 to 99% by weight and the proportion of the binder component being 1 to 99.9% by weight each based on the total solids content of the zinc oxide-based particles and the binder component.

(95) A coated article comprising at least one substrate selected from the group consisting of a resin molded article, glass and paper and a coating film provided on the substrate which is formed of the coating composition described in (94).

(96) A resin composition comprising the zinc oxide-based particles produced by the process described in any of (27) to (36) and a resin capable of forming a continuous phase having dispersed therein the zinc oxide-based particles, the proportion of the zinc oxide-based particles being 0.1 to 99% by weight and the proportion of the resin being 1 to 99.9% by weight each based on the total solids content of the zinc oxide-based particles and the resin.

(97) A resin molded article obtained by molding the resin composition described in (96) into at least one shape selected from the group consisting of a plate, a sheet, a film, and fiber.

(98) Paper comprising pulp made into paper and having dispersed therein the zinc oxide-based particles produced by the process described in any of (27) to (36), the proportion of the zinc oxide-based particles being 0.01 to 50% by weight based on the pulp.

(99) A cosmetic containing 0.1% by weight or more of the zinc oxide-based particles produced by the process described in any of (27) to (36).

(100) A coating composition comprising the inorganic compound particles produced by the process described in any of (19) to (26) and a binder component capable of forming a coating film binding the inorganic compound particles, the proportion of the inorganic compound particles being 0.1 to 99% by weight and the proportion of the binder component being 1 to 99.9% by weight each based on the total solids content of the inorganic compound particles and the binder component.

(101) A coated article comprising at least one substrate selected from the group consisting of a resin molded article, glass and paper and a coating film provided on the substrate which is formed of the coating composition described in (100).

(102) A resin composition comprising the inorganic compound particles produced by the process described in any of (19) to (26) and a resin capable of forming a continuous phase having dispersed therein the inorganic compound particles, the proportion of the inorganic compound particles being 0.1 to 99% by weight and the proportion of the resin being 1 to 99.9% by weight each based on the total solids content of the inorganic compound particles and the resin.

(103) A resin molded article obtained by molding the resin composition described in (102) into at least one shape selected from the group consisting of a plate, a sheet, a film, and fiber.

(104) Paper comprising pulp made into paper and having dispersed therein the inorganic compound particles produced by the process described in any of (19) to (26), the proportion of the inorganic compound particles being 0.01 to 50% by weight based on the pulp.

(105) A cosmetic containing 0.1% by weight or more of the inorganic compound particles produced by the process described in any of (19) to (26).

(106) An antimicrobial agent comprising the inorganic compound particles produced by the process described in any of (19) to (26).

(107) A controlled releasing agent comprising the inorganic compound particles produced by the process described in any of (19) to (26).

(108) An adsorbent comprising the inorganic compound particles produced by the process described in any of (19) to (26).

(109) An adhesive comprising zinc oxide-polymer composite particles produced by the process described in any of (10) to (18).

(110) An adhesive comprising the zinc oxide-polymer composite particles described in any of (37) to (42).

The present invention will be described below in detail.

The process for producing zinc oxide fine particles described in (1) to (9) above is first explained.

The zinc oxide fine particles as referred to in the invention essentially comprise zinc atoms and oxygen atoms in a proportion of 60% by weight or more in the form of ZnO and exhibit an X-ray diffraction pattern of a hexagonal system (wurtzite structure), a cubic system (rock salt structure) or a face-centered-cubic structure. Therefore, as far as the amount of zinc and oxygen falls within the above range, the zinc oxide fine particles include composite fine particles of zinc oxide crystals and a metal element other than zinc, e.g., an alkali metal or an alkaline earth metal, in the form of an atom or an ion; fine particles of solid solutions of an inorganic compound of a metal element other than zinc, e.g., an oxide, a hydroxide, a sulfide, a nitride, a carbide or a carbonate, in zinc oxide crystals; fine particles in which an organometallic compound, such as a coupling agent (e.g., a silane coupling agent and an alumina coupling agent), an organosiloxane or a chelate compound, is bound to the surface of the zinc oxide crystals or forms a coating layer on the surface of the zinc oxide crystals; and fine particles containing a halogen element, an inorganic acid (e.g., a sulfuric acid radical and a nitric acid radical) or an organic compound (e.g., a fatty acid, an alcohol, and an amine) in the inside and/or on the surface thereof.

While the size of the zinc oxide fine particles obtained by the process of the invention is not particularly limited, zinc oxide fine particles having an average primary particle size controlled within a range of from 0.005 to 10 $\mu$m, particularly of from 0.005 to 0.1 $\mu$m, and exhibiting excellent dispersibility can be produced through a simple process not heretofore attempted.

The zinc oxide fine particles prepared by the process of the invention are obtained as a dispersion containing 1 to 80% by weight, in terms of zinc oxide, of finely divided zinc oxide particles. The zinc oxide fine particles can be in the following state in the dispersion.
(a) Primary particles are finely dispersed without undergoing secondary agglomeration.
(b) Primary particles are in a secondarily agglomerated state partly or totally.
(c) Particles of different kind in which zinc oxide primary particles are dispersed are dispersed.

All the states illustrated above are included in the concept represented by the term "dispersion" of zinc oxide fine particles.

The zinc source used as a raw material is by no means limited provided that it is zinc or a compound containing zinc. Preferred zinc sources include metallic zinc (zinc powder), zinc oxide (zinc white), zinc hydroxide, basic zinc carbonate, zinc acetate, zinc octylate, zinc stearate, zinc oxalate, zinc lactate, zinc tartrate, and zinc naphthenate; for they do not require a desalting step that has been essential in a conventional process starting with zinc chloride, zinc nitrate, zinc sulfate, etc. Still preferred of them are metallic zinc (zinc powder), zinc oxide (zinc white), zinc hydroxide, basic zinc carbonate, and zinc acetate for their inexpensiveness and ease in handling. Zinc oxide, zinc hydroxide, and zinc acetate are particularly preferred for ease in controlling the size and shape of the resulting zinc oxide fine particles.

The carboxyl-containing compound for use in the invention includes all the compounds containing at least one carboxyl group per molecule. Specific examples of such compounds include acyclic carboxylic acids, such as saturated fatty acids (or saturated monocarboxylic acids), e.g., formic acid, acetic acid, propionic acid, isobutyric acid, caproic acid, caprylic acid, lauric acid, myristic acid, palmitic acid, and stearic acid; unsaturated fatty acids (or unsaturated monocarboxylic acids), e.g., acrylic acid, methacrylic acid, crotonic acid, oleic acid, and linolenic acid; saturated polycarboxylic acids, e.g., oxalic acid, malonic acid, succinic acid, adipic acid, suberic acid, and $\beta,\beta$-dimethylglutaric acid; and unsaturated polycarboxylic acids, e.g., maleic acid and fumaric acid; cyclic saturated carboxylic acids, such as cyclohexanecarboxylic acid; aromatic carboxylic acids, such as aromatic monocarboxylic acids, e.g., benzoic acid, phenylacetic acid, and toluylic acid; and unsaturated polycarboxylic acids, e.g., phthalic acid, isophthalic acid, terephthalic acid, pyromellitic acid, and trimellitic acid; carboxylic acid anhydrides, such as acetic anhydride, maleic anhydride, and pyromellitic anhydride; compounds having a functional group or atomic group other than a carboxylic group (e.g., a hydroxyl group, an amino group, a nitro group, an alkoxy group, a sulfonic acid group, a cyano group, a halogen atom, etc.) in the molecule thereof, such as trifluoroacetic acid, monochloroacetic acid, o-chlorobenzoic acid, o-nitrobenzoic acid, anthranilic acid, p-aminobenzoic acid, anisic acid (i.e., p-methoxybenzoic acid), toluylic acid, lactic acid, and salicylic acid (i.e., o-hydroxybenzoic acid); and polymers comprising the above-described unsaturated carboxylic acid as at least one constituent unit, such as acrylic acid homopolymers and acrylic acid-methyl methacrylate copolymers. Preferred among them are saturated fatty acids having a boiling point of 200° C. or lower at atmospheric pressure.

The carboxyl-containing compound further include carboxyl-containing zinc compounds, such as zinc carboxylates, e.g., zinc acetate and zinc oxalate. When such zinc compounds are used as a zinc source, it is not always necessary to separately add the above-mentioned carboxyl-containing compound.

The alcohol which can be used as a raw material in the invention includes aliphatic monohydric alcohols, such as methanol, ethanol, isopropyl alcohol, n-butanol, t-butyl alcohol, and stearyl alcohol; aliphatic unsaturated monohydric alcohols, such as allyl alcohol, crotyl alcohol, and propargyl alcohol; alicyclic monohydric alcohols, such as cyclopentanol and cyclohexanol; aromatic monohydric alcohols, such as benzyl alcohol, cinnamyl alcohol, and methyl phenyl carbinol; heterocyclic monohydric alcohols, such as furfuryl alcohol; glycols, such as ethylene glycol, propylene glycol, trimethylene glycol, 1,4-butanediol, 1,5-pentanediol, 1,6-hexanediol, 1,8-octanediol, 1,10-decanediol, pinacol, diethylene glycol, and triethylene glycol; aliphatic glycols having an aromatic ring, such as hydrobenzoin, benzpinacol, and phthalyl alcohol; alicyclic glycols, such as cyclopentane-1,2-diol, cyclohexane-1,2-diol, and cyclohexane-1,4-diol; polyoxyalkylene glycols (e.g., polyethylene glycol and polypropylene glycol); and monoethers and monoesters of the above-described glycols, such as ethylene glycol monoethyl ether, ethylene glycol monobutyl ether, triethylene glycol monomethyl ether, and ethylene glycol monoacetate; aromatic diols, such as hydroquinone, resorcin, and 2,2-bis(4-hydroxyphenyl) propane, and monoethers and monoesters of these diols; and trihydric alcohols, such as glycerol, and alcoholic derivatives of the trihydric alcohols, such as monoethers, monoesters, diethers, and diesters. These compounds can be used either individually or as a combination of two or more thereof. In particular, alcohols having a boiling point of 120° C. or higher at atmospheric pressure are preferred; for fine particles of excellent crystalline properties can easily be obtained under atmospheric pressure and in a short time. For ease of obtaining fine particles having excellent dispersibility, monohydric alcohols having a boiling point of 120° C. or higher and a water solubility of not less than 1% by weight at 20° C., for example, monoethers or monoesters of glycols and n-butanol, are especially preferred.

The present invention is characterized in that a mixture comprising the aforementioned zinc source, carboxyl-containing compound and alcohol is heated. The zinc source is converted to zinc oxide which is X-ray crystallographically crystalline upon being heated in a mixture of the carboxyl-containing compound and the alcohol, and, at the same time, a dispersion containing zinc oxide fine particles is obtained. If any one of the three components, i.e., a zinc source, a carboxyl-containing compound, and an alcohol, is missing, precipitation of zinc oxide crystals does not take place, resulting in a failure of obtaining a dispersion of zinc oxide fine particles.

The step of conversion of a zinc source to X-ray crystallographically crystalline zinc oxide sometimes involves formation of one or more zinc oxide precursors. The case of using zinc oxide as a zinc source may be mentioned as an example. In this case, the term "zinc oxide precursors" means ions or compounds other than zinc oxide which contain at least a zinc atom. For example, the precursors include a zinc (hydrate) ion ($Zn^{2+}$), a polynuclear hydroxide ion of zinc, the above ions partly or totally chelated by a chelating compound, e.g., a β-dicarbonyl compound (e.g., acetylacetone), lactic acid, ethylene glycol or ethanolamine, and a (basic) carboxylic acid salt, such as (basic) zinc acetate, (basic) zinc salicylate, and (basic) zinc lactate. The precursor may be present with a part or the whole thereof forming a composite composition with the carboxyl-containing compound and/or the alcohol as, for example, a complex salt.

In the stage where a zinc source is converted to zinc oxide fine particles, the carboxyl-containing compound in the mixture does not change or partly or totally undergoes esterification with a part or the whole of the alcohol in the mixture to form an ester compound.

The mixture is not limited provided that it is a mixture obtained by mixing the above-described three essential components, i.e., a zinc source, a carboxyl-containing compound, and an alcohol. If desired, the mixture may contain components other than the three components, such as water; organic solvents, e.g., ketones, esters, (cyclo) paraffins, ethers, and aromatic compounds; additives hereinafter described; metallic components other than zinc, e.g., inorganic metal salts (e.g., an acetate, a nitrate or a chloride) and organometallic alkoxides (e.g., metal alkoxides). The water or organic solvents are usually used as a solvent component.

The state of the three components in the mixture, considered either mutually or individually, is not particularly limited. Taking the zinc source, for instance, it can be dissolved as such in a solvent component, such as the alcohol and/or water or an organic solvent; or the zinc source is changed to the above-described zinc oxide precursor and dissolved or dispersed in a colloidal, emulsified or suspended state.

Accordingly, the state of the mixture is not particularly limited. Whether the mixture is liquid, sol, an emulsion or a suspension is of no problem.

While the raw material composition for preparing the mixture is not particularly limited, it is desirable from the viewpoint of economy and ease of formation of zinc oxide fine particles that the amount of the zinc source to be used as a raw material of the mixture ranges from 0.1 to 95% by weight, in terms of ZnO, based on the total amount of the mixture and that the amount of the carboxyl-containing compound to be used as a raw material of the mixture ranges from 0.5 to 50 mol per mole of Zn atoms of the zinc source used as a raw material of the mixture. The above ranges are usually selected.

The mixture is prepared by mixing the components in the above ranges. The manner of preparation is not particularly restricted.

In order to obtain a dispersion of zinc oxide fine particles while controlling the average particle size of the primary particles within a range of from 0.005 to 10 μm, it is preferred for practical productivity to add the first mixture comprising a zinc source and a carboxyl-containing compound to a heated alcohol-containing solution to prepare the second mixture.

It is particularly preferred that a first mixture is obtained from a zinc source and a carboxyl-containing compound, and the first mixture is added to an alcohol-containing solution maintained at 60° C. or above, preferably at 100° C. or higher, to prepare a second mixture, and the resulting second mixture is heated.

The method of preparing the mixture according to the above-described preferred mode is further illustrated below.

Addition of the first mixture can be carried out by adding the whole amount of the first mixture all at once, or adding the first mixture dropwise on or into the alcohol-containing solution, or spraying the first mixture.

Addition of the first mixture may be conducted at atmospheric pressure, under pressure, or under reduced pressure. Addition at atmospheric pressure is preferred from the economical consideration. In this case, when a zinc oxide fine particle dispersion having uniformity in particle size and shape, etc. and a controlled dispersed or agglomerated state is desired, it is preferable to keep the alcohol-containing solution at 60° C. or higher, particularly 100° C. to 300° C., during addition and mixing. If the temperature of the alcohol-containing solution during addition and mixing is lower than 60° C., the viscosity of the second mixture tends to increase suddenly during or after addition and mixing, resulting in gelation. If this happens, there arise such problems that stirring is impossible and unsuccessfully achieves uniform mixing or heat conduction in the subsequent step, i.e., heating, is insufficient, resulting in creation of temperature distribution. It follows that zinc oxide fine particles uniform in crystalline properties, particle size and particle shape can hardly be obtained but agglomerated particles. This problem also concerns the concentration of zinc in the second mixture and is more liable to occur at a higher zinc concentration. The lowest suitable temperature varies according to the pressure of the system. When the first mixture is added under reduced pressure or under pressure, the temperature of the alcoholic solvent should be selected appropriately. This does not apply when a dispersion of agglomerated zinc oxide fine particles is desired. When the first mixture is added to the alcohol-containing solution under heating as described above, part of the carboxyl-containing compound and/or part of the alcohol of the second mixture are sometimes driven out of the system through evaporation. The mixture thus prepared is also included in the concept of "second mixture".

While the raw material composition for preparing the first mixture is not particularly limited, it is preferable that the amount of the zinc source to be used as a raw material of the first mixture ranges from 1 to 90% by weight, in terms of ZnO, based on the total amount of the first mixture and that the amount of the carboxyl-containing compound to be used as a raw material of the first mixture ranges from 0.5 to 50 mol per mole of Zn atoms of the zinc source.

The thus prepared first mixture is added and mixed with the alcohol-containing solution to obtain the second mixture.

The first mixture when added may be at room temperature or as heated. For obtaining a uniform mixture, the alcohol-containing solution is preferably stirred while the first mixture is being added thereto.

While not limiting, the amount of the alcohol in the alcohol-containing solution preferably ranges from 1 to 100 mol per mole of the Zn atom originated in the zinc source present in the second mixture so that the formation of zinc oxide fine particles under heating may be completed in a short time period. The alcohol concentration in the alcohol-containing solution is usually in a range of from 5 to 100% by weight based on the total weight of the solution.

Heating of the thus prepared second mixture results in production of a dispersion containing zinc oxide fine particles in good yield.

The heating temperature is not particularly limited. The heating must be, as a matter of course, at or above the temperature at which crystalline zinc oxide precipitates, but the temperature cannot be decided definitely because it is subject to variation in accordance with desired morphology of zinc oxide fine particles, such as the size, shape and state of dispersion or agglomeration. The heating temperature and heating time should be selected from a comprehensive point of view including the initial composition of the second mixture and the above-mentioned various parameters. In particular, when it is desired to obtain a dispersion of zinc oxide fine particles having the average primary particle size controlled within a range of 0.005 to 10 µm with a practical productivity, it is preferable to heat the second mixture at 100° C. or higher, still preferably 100 to 300° C., particularly preferably 120 to 200° C.

In the case when the first mixture is added to an alcohol-containing solution kept at 100° C. or higher, heating of the resulting second mixture can be achieved by maintaining the mixture at that temperature, or the mixture is heated or cooled to a prescribed temperature, followed by carrying out a heat treatment. In the case when the first mixture is added to an alcohol-containing solution below 100° C. the resulting second mixture is heated to 100° C. or higher, followed by carrying out a heat treatment. To set the second mixture heating temperature at 100° C. or higher brings about the advantage that strict control on the composition of the reaction system for obtaining zinc oxide fine particles, inclusive of control on the rate of evaporation of excessive or unnecessary components and the amount of evaporated components, can be taken easily. As a result, the particle size and the like of the resulting fine particles can be controlled easily.

In the heating step for obtaining the dispersion, the components other than the above-described ones, i.e., the alcohol, the aforesaid ester compound produced upon heating, or the solvent component which may, if desired, have been used in the mixture may be removed by evaporation partially or completely.

While not limiting, a preferred heating time for completion of the reaction is usually about 0.1 to 30 hours.

Where water is present in the second mixture, it is preferable for conversion to zinc oxide fine particles to evaporate the water during the heating step to reduce the free water content to 5% by weight or lower, particularly 1% by weight or lower. If the water content exceeds the above level, cases are sometimes met with that the zinc oxide fine particles have reduced crystalline properties, resulting in a failure of fulfilling the function of zinc oxide, while such depends on the kinds of the other components present in the dispersion, such as the alcohol.

It is preferable that the amount of the carboxyl-containing compound in a finally obtained zinc oxide fine particle dispersion be 0.5 mol or less per mole of the total zinc atoms present in the dispersion. If it exceeds 0.5 mol, cases are sometimes met with that the zinc oxide fine particles have reduced crystalline properties, failing to fulfill the function of zinc oxide. Accordingly, where the amount of the carboxyl-containing compound present in the second mixture is such that the amount of the carboxyl-containing compound in the finally obtained dispersion will exceed 0.5 mol per mole of the total zinc atoms in the resulting dispersion, at least the excess should be removed by evaporation during the heating step. Needless to say, the carboxyl-containing compound may be evaporated during heating even if the above molar ratio is 0.5 or lower.

It is also possible to add a specific additive to the system in the step of heating for the purpose of controlling the size, shape, dispersed state or higher-order state of the primary particles of the finally obtained zinc oxide fine particles and/or the polarity or composition of the surface of the fine particles. The stage of addition of the additive is not particularly restricted. The additive can be added in either of the step of preparing the second mixture or the first mixture or the step of heating. The stage of addition is selected appropriately according to the purpose and the kind of the additive. In many cases, the effects of the additive are fully exerted when added immediately before or after precipitation of zinc oxide crystals.

In particular, in order to obtain zinc oxide fine particles having high uniformity in size and shape of the primary particles, it is preferable that a compound containing in the molecule thereof one or more than one atomic group of at least one kind selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group and having a molecular weight of less than 1,000 be present as an additive in the system in the heating step.

Useful additives include the above-illustrated carboxyl-containing compounds, such as long-chain saturated fatty acids (e.g., caprylic acid, lauric acid, myristic acid, palmitic acid, and stearic acid) and esters thereof; amino-containing compounds, such as alcohols having a primary, secondary or tertiary amino group (e.g., monoethanolamine, diethanolamine, and N,N-dimethylethanolamine), quaternary ammonium salts (e.g., tetramethylammonium hydroxide and n-hexadecyltrimethylammonium hydroxide), amino acids, amino(di)carboxylic acids and esters or anhydrides thereof (e.g., 6-aminocaproic acid, N,N-bis (octylaminoethyl)glycine, p-aminobenzoic acid, aspartic acid, and glutamic acid), pyridine derivatives (e.g., 2-hydroxypyridine and pyridine-2,6-dicarboxylic acid), and aliphatic amines (e.g., octadecylamine and stearylamine); amides, such as dimethylformamide, dimethylacetamide, benzamide, oxamide, and oxamic acid; imino-containing compounds, such as acid imides (e.g., succinimide and phthalimide), imino(di)carboxylic acids (e.g., imino(di) acetic acid), and iminoethers; ureido-containing compounds and derivatives thereof, such as dicarboxylic acid ureides (e.g., parabanic acid, alloxan, barbituric acid, and dialuric acid), ureido-acids (e.g., oxaluric acid and malonuric acid), diureides (e.g., uric acid), β-aldehyde-acid ureides (e.g., uracil), and α-oxyacid ureides (e.g., 5-methylhydantoin); urethane compounds (e.g., ethyl carbamate) and derivatives thereof, such as N-nitroso compounds and N-chloroacetylated compounds; isocyanate-containing compounds (e.g., tolylene diisocyanate, diisocyanyl diphenylmethane, hexamethylene diisocyanate, isobutyl isocyanate, and phenyl isocyanate); epoxy-containing compounds, such as aliphatic diglycidyl ethers (e.g., 1,2-epoxycyclohexene, 1,8-cineole, ethylene glycol diglycidyl ether, and 1,6-hexanediol diglycidyl ether), polyglycidyl ethers (e.g., glycerol triglycidyl ether and pentaerythritol tetraglycidyl ether), aliphatic and aromatic diglycidyl esters (e.g., diglycidyl adipate), resorcin glycidyl ether, bisphenol A diglycidyl ether, and oligomers having an epoxy group as a functional group; various coupling agents including silane coupling agents (e.g., methyltrimethoxysilane, phenyltrimethoxysilane, benzyltriethoxysilane, γ-aminopropyltriethoxysilane, N-β(aminoethyl)γ-aminopropyltrimethoxysilane, γ-glycidoxypropyltrimethoxysilane, γ-methacryloxypropyltrimethoxysilane, γ-mercaptopropyltrimethoxysilane, γ-chloropropyltrimethoxysilane, and stearyltrimethoxysilane), titanate coupling agents (e.g., isopropyltriisostearoyl titanate, bis(dioctyl pyrophosphate) oxyacetate titanate, tetraoactylbis(ditridecyl phosphite) titanate, and isopropyltri(N-aminoethylaminoethyl) titanate), and aluminum coupling agents (e.g., ethylacetoacetatealuminum diisopropylate), and partial hydrolysis products thereof; organometallic compounds containing a metallic hydroxyl group and/or a metallic alkoxy group other than the above-described coupling agents, such as metal alkoxides (e.g., tetramethoxysilane, tetraethoxysilane, tetrabutoxysilane, diethoxydimethylsilane, trimethylethoxysilane, hydroxyethyltriethoxysilane, titanium tetraethoxide, titanium tetrabutoxide, titanium diethyldiethoxide, titanium tetrabutoxide, zirconium tetramethoxide, zirconium tetrabutoxide, aluminum trimethoxide, aluminum tri-n-butoxide, aluminum triisopropoxide, boron triethoxide, tri-n-butyl borate, gallium triethoxide, gallium tri-n-butoxide, strontium diethoxide, tungsten hexaethoxide, manganese di-n-butoxide, cobalt diisopropoxide, nickel diethoxide, nickel di-n-butoxide, lanthanum triethoxide, barium diethoxide, yttrium triethoxide, copper diethoxide, copper di-n-butoxide, niobium pentaethoxide, niobium penta-n-butoxide, tantalum pentaethoxide, tantalum penta-n-butoxide, indium triethoxide, indium tri-n-butoxide, tin tetraethoxide, tin tetra-n-butoxide, iron triethoxide, and iron tri-n-butoxide) and derivatives of these organometallic compounds, such as (partial) hydrolysis products or condensation products (e.g., oligomers or polymers) obtained by (partial) hydrolysis and/or condensation of the organometallic compounds either individually or as combined; organophosphorus compounds, such as phosphoric esters (e.g., trimethyl phosphate, triethyl phosphate, tributyl phosphate, tris(2-chloroethyl) phosphate, and (polyoxyethylene)bis[bis(2-chloroethyl)phosphate]), acid phosphoric esters (e.g., methyl acid phosphate, propyl acid phosphate, lauryl acid phosphate, stearyl acid phosphate, bis-2-ethylhexyl phosphate, and diisodecyl phosphate), phosphorous esters (e.g., trimethyl phosphite), and thiophosphoric esters (e.g., diisopropyl dithiophosphate); organopolysiloxanes containing in the molecule thereof at least one of the above-mentioned atomic groups, such as an amino group (a primary, secondary or tertiary amino group, a quaternary ammonio group, etc.), a carboxyl group, a sulfonic acid group, a phosphoric acid group, a hydroxyl group, and an epoxy group; various surface active agents containing the above-mentioned atomic group, such as anionic surface active agents (e.g., sodium lauryl sulfate, sodium dodecylbenzenesulfonate, sodium polyoxyethylene lauryl ether sulfate, a sodium dialkylsulfosuccinate, and calcium stearate), nonionic surface active agents (e.g., polyoxyethylene lauryl ether, a polyoxyethylene alkylamine, polyethylene glycol monolaurate, and glycerol monostearate), cationic surface active agents (e.g., lauryldimethylamine and stearyltrimethylammonium chloride), and amphoteric surface active agents (e.g., lauryl betaine and stearylamine acetate); and polymers containing at least one of the above-described atomic groups, such as (meth)acrylic polymers (e.g., an acrylic acid-methyl methacrylate copolymer and acrylamide-methyl methacrylate copolymer), polyurethanes, and polyesters.

Further, the shape or size of the crystals can be controlled by addition of a chelating agent (multidentate ligand) capable of multidentate coordination to a zinc ion to form a chelate compound.

Examples of the chelating agent (multidentate ligand) capable of forming a chelate compound through multidentate coordination to a zinc ion are β-diketones (e.g., acetylacetone, ethyl acetoacetate, and benzoylacetone), ethylenediamine, dimethyl glyoxime, benzyl dioxime, cyclohexane-1,2-dione dioxime, dithizone, oxine, glycine, glycolic acid, oxalic acid, catechol, dipyridine, 1,10-phenanthroline, α-hydroxypropionic acid, monoethanolamine, diethanolamine, and ethylene glycol.

As previously described, the resulting zinc oxide fine particles show wide variations in shape and size of the primary particles, the state of dispersion or higher-order structure of the primary particles, surface polarity, surface composition, and the like depending on the kind or amount of the additive. For example, there are cases in which composite fine particles comprising the additive and zinc oxide fine particles are obtained, or zinc oxide particles unique in shape and/or higher-order structure of the primary particles are obtained. Taking, for instance, addition of a compound having a hydrophilic main chain, such as methoxypoly(oxyethylene)monoglycolic acid, there are obtained zinc oxide fine particles which are regular in size and shape of the primary particles and also exhibit excellent dispersibility of the primary particles in a polar solvent, such as water. When in using a compound having a highly hydrophobic or lipophilic main chain, such as an alkyltrialkoxysilane or octadecylamine, there are obtained zinc oxide fine particles which are regular in size and shape of the primary particles and also exhibit excellent dispersibility of the primary particles in a low-polar or non-polar solvent, such as toluene.

While not limiting, a preferred amount of the additive to be added is usually 0.1 to 30% by weight based on the zinc oxide contained in the dispersion. If the amount is less than 0.1%, the effect of addition is insubstantial. If it exceeds 30%, the system tends to fail to produce zinc oxide.

The additives may be used either individually or as a mixture thereof. The manner of addition is not restricted and can appropriately be selected according to the kind of the additive or the time of addition. When an additive is added during heating, for example, it can be added to the system either as such or as dissolved in and/or diluted with an arbitrary solvent, such as an alcohol. The latter manner is advantageous in that the additive is diffused through the reaction system more easily to produce higher effects of addition.

If carbon dioxide and/or a carbonic acid source is/are present in the step of mixing the first mixture with an alcohol-containing solution (second mixing step) or in the step of heating the resulting second mixture, fine particles whose primary particles have regular shape and size, excellent dispersibility in water, and very small size (0.05 μm or smaller) can be obtained easily. Instead of using a carbonic acid source separately, (basic) zinc carbonate may be used as part of a zinc source to serve in substitution for a carbonic acid source. A suitable amount of a carbonic acid source is 0.1 to 20 mol % based on zinc. Too much carbonic acid sometimes interferes with crystallization of zinc oxide, and such being the case, the heating temperature must be increased. Carbonic acid sources include, in addition to zinc carbonate, compounds producing carbonate ions or carbon acid gas on, e.g., heating, such as ammonium carbonate, ammonium hydrogencarbonate, and urea; metal carbonates, such as yttrium carbonate, cadmium carbonate, silver carbonate, samarium carbonate, zirconium carbonate, cerium carbonate, thallium carbonate, lead carbonate, and bismuth carbonate; and basic metal carbonates, such as basic zinc carbonate, basic cobalt(II) carbonate, basic copper(II) carbonate, basic lead(II) carbonate, and basic nickel(II) carbonate. These carbonic acid sources can be used either individually or as a combination of two or more thereof.

As a preferred embodiment of the invention, zinc oxide fine particles having an average primary particle size controlled within a range of from 0.005 to 0.1 $\mu$m can be obtained when any one of the following conditions (I) to (IV), preferably 2 or 3 of (I) to (IV), still preferably all of (I) to (IV) are satisfied.

(I) Of the above-described zinc sources, a zinc source mainly comprising at least one compound selected from the group consisting of zinc oxide, zinc hydroxide, and zinc acetate, particularly a zinc source mainly comprising zinc oxide and/or zinc hydroxide is used.

Zinc oxide, zinc hydroxide, and zinc acetate contain substantially no impurity that might interfere with the reaction forming zinc oxide fine particles in the heating step, therefore making it easy to strictly control the particle size to such fineness of 0.005 to 0.1 $\mu$m. Above all, zinc oxide and zinc hydroxide are available at a low price, allow a free choice of the carboxyl-containing compound to be combined with, and make it particularly easy to obtain fine particles within the above particle size range.

(II) The carboxyl-containing compound is a saturated fatty acid having a boiling point of 200° C. or lower at atmospheric pressure.

Specifically, formic acid, acetic acid, propionic acid, butyric acid, and isobutyric acid are preferred. With these compounds, it is easy to control the carboxyl group content in the reaction system from mixing through heating, thus making it easy to strictly control the primary particle size to such fineness. It is still preferable to use the above saturated fatty acid in a proportion of 80 mol % or higher in the total carboxyl-containing compounds.

While the content of the carboxyl-containing compound falling within the above-described preferred range is not limited further, a particularly preferred content of the carboxyl-containing compound in the first mixture ranges from 2.2 to 10 mol per mole of Zn atoms of the zinc source for obtaining fine particles which are prevented from secondary agglomeration and exhibit excellent dispersibility.

(III) The second mixture is prepared by adding the first mixture, obtained by mixing zinc or a compound thereof and a carboxyl-containing compound, kept at 60° C. or above to an alcohol-containing solution kept at 100° C. or above, particularly 100° to 300° C., by continuous or intermittent dropwise addition.

The first mixture is preferably in a liquid state. It is still preferable that the zinc source and the carboxyl-containing compound are mutually dissolved or they are dissolved in a solvent having high compatibility with both of them. Water, alcohols, ketones, and esters are advantageous as such a solvent in that they easily dissolve the zinc source and the carboxyl-containing compound under heating at room temperature up to about 100° C. and that they are also highly compatible with the alcoholic solvent. The term "alcohols" as used above embraces all the alcohol species hereinabove described.

(IV) The heating of the second mixture is conducted at 100° to 300° C., particularly 120° C. or higher.

The zinc oxide fine particles having an average primary particle size ranging from 0.005 to 0.1 $\mu$m can be made into those having further controlled uniformity in size and shape of their primary particles, controlled surface conditions, such as hydrophilic/lipophilic properties, or a controlled state of dispersion or agglomeration. Effective methods for controlling these attributes are described below. In the preferred process for producing zinc oxide fine particles having an average primary particle size of 0.005 to 0.1 $\mu$m, addition of the above-described additive in the same manner as described above is effective in obtaining zinc oxide fine particles having a controlled primary particle shape, a controlled state of primary particle dispersion or higher-order structure, controlled surface polarity, and the like, and composite fine particles having dispersed therein such zinc oxide fine particles. When it is desired to produce zinc oxide fine particles having a regular primary particle size distribution, with the average particle size substantially falling within the above range, and having excellent dispersibility in various solvents, it is preferable to use a zinc source comprising at least one compound selected from the group consisting of zinc oxide, zinc hydroxide, and zinc acetate as a main component and, as a secondary component, basic zinc carbonate and/or a zinc salt of a carboxyl-containing compound having a boiling point higher than the heating temperature at atmospheric pressure. The ratio of the secondary component to the main component is 0.01 to 20% in terms of zinc atom ratio. If the ratio is less than 0.01%, the effect of the combined use of the secondary component is insufficient. If it exceeds 20%, the system sometimes fails to produce zinc oxide.

When the above-described conditions are satisfied in the process of the invention, there is obtained a dispersion of zinc oxide fine particles containing 1 to 80% by weight of zinc oxide in an alcohol and/or the above-described ester compound and/or an organic solvent, in which the primary particles have an average particle size of 0.005 to 0.1 $\mu$m, and the shape, the surface condition, the state of dispersion or agglomeration, and the like of the particles are controlled.

The dispersion of the zinc oxide fine particles obtained in the invention can be used as such. If desired, the dispersion can easily be powdered or transformed to a coating composition containing the zinc oxide fine particles or a dispersion of the zinc oxide fine particles in a different medium by solvent substitution.

Powder of zinc oxide can be obtained by separating the zinc oxide fine particles from the dispersion in a conventional manner, such as filtration, centrifugation or solvent evaporation, followed by drying or, if desired, calcination. In particular, a powdering method in which the dispersion (or a concentrated dispersion) is evaporated to remove the solvent by means of a vacuum flash evaporator suppresses secondary agglomeration of fine particles, which often occurs during drying, and is therefore preferred for obtaining zinc oxide powder having excellent dispersibility.

A dispersion of zinc oxide fine particles in a solvent different from that of the dispersion as obtained in the invention can be prepared by a known method comprising mixing zinc oxide powder obtained by the above-described powdering method with a desired solvent such as water and dispersing the mixture with mechanical energy by means of a ball mill, a sand mill, an ultrasonic homogenizer, etc. A dispersion in a different solvent can also be prepared by mixing the dispersion as obtained in the invention with a desired solvent while heating the dispersion to evaporate part or the whole of the solvent to be replaced (solvent substitution under heating). The solvent to be substituted for the initial one is not particularly limited and includes organic solvents, such as alcohols, aliphatic or aromatic carboxylic acid esters, ketones, ethers, ether esters, aliphatic or aromatic hydrocarbons, and halogenated hydrocarbons; water, mineral oil, vegetable oil, wax oil, silicone oil, and the like. A suitable solvent can be selected appropriately according to the end use.

In what follows, the process for producing zinc oxide-polymer composite particles described in (10) to (18) above and the zinc oxide-polymer composite particles described in (37) to (42) are explained.

The zinc oxide-polymer composite particles according to the invention comprise zinc oxide fine particles and a polymer, the proportion of the zinc oxide fine particles being 50 to 99% by weight based on the total weight of the composite fine particles and the polymer, and the zinc oxide particles having an outer shell comprised of a mixture and/or a composite of the zinc oxide fine particles and a polymer with the inside of the outer shell being hollow.

The composite particles of the invention preferably have a number average particle size of 0.1 to 10 µm with a coefficient of particle size variation being not more than 30%, particularly not more than 15%.

When the composite particles of the invention have a number average particle size of 0.1 to 10 µm with a coefficient of particle size variation being not more than 30%, it is preferable that the zinc oxide fine particles have a number average particle size of 0.005 to 0.1 µm and the ratio of the number average particle size of the zinc oxide fine particles to that of the zinc oxide-polymer composite particles is 1/10 to 1/1,000.

The composite particles of the invention have, for example, a spherical shape and/or an ellipsoidal shape.

In order for the composite particles of the invention to have high light diffusing properties, the composite particles preferably have an outer shell comprised of an aggregate of zinc oxide fine particles. Those composite particles in which the inside of the outer shell is hollow exhibit further improved light diffusing properties.

The polymer contained in the composite particles have, for example, at least one polar atomic group. The polar atomic group is selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group.

The zinc oxide-polymer composite particles of the invention are produced by a process comprising heating a mixture of a zinc source, a carboxyl-containing compound, a polymer, and an alcohol to a temperature of 100° C. or higher.

The above process preferably comprises a first mixing step and a second mixing step. The first mixing step is a step in which the zinc source and the carboxyl-containing compound are mixed to prepare a first mixture containing zinc and the carboxyl-containing compound. The second mixing step is a step in which the first mixture and an alcohol are mixed to prepare a second mixture containing zinc and the carboxyl-containing compound in the alcohol.

The first mixing step may be a step in which the zinc source is dissolved in a mixed solvent of the carboxyl-containing compound and water.

The second mixing step may be a step in which the first mixture is added to the medium maintained at 100° C. or higher.

The polymer which can be used in the process of the invention contains, for example, at least one polar atomic group. The polar atomic group is, for example, at least one atomic group selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group.

The zinc source for use in the process is preferably at least one zinc compound selected from the group consisting of zinc oxide, zinc hydroxide, and zinc acetate.

The carboxyl-containing compound for use in the process is preferably a saturated fatty acid having a boiling point of 200° C. or lower at atmospheric pressure.

The polymer is used at a weight ratio of 0.01 to 1.0 to the zinc atoms, in terms of zinc oxide, present in the zinc source.

The zinc oxide-polymer composite particles according to the invention are described below in greater detail.

The zinc oxide-polymer composite particles of the invention contain 50 to 99% by weight, in terms of ZnO, of zinc oxide fine particles and 1 to 50% by weight of a polymer, preferably 70 to 90% by weight, in terms of ZnO, of the zinc oxide fine particles and 5 to 30% by weight of the polymer, each based on the total weight of the zinc oxide fine particles and the polymer. If the proportion of the zinc oxide fine particles is less than the above range, there is a tendency that the UV screening power per composite fine particle reduces. If the proportion exceeds the upper range, the composite particles tend to have insufficient mechanical strength for practical use.

Zinc oxide that constitutes the composite particles is preferably crystals; for crystalline zinc oxide has excellent visible light transmitting properties, is free from coloration, shows a wide range of UV absorption wavelengths thereby efficiently cutting UV light, and has low toxicity. Zinc oxide crystals generally exhibit an X-ray diffraction pattern of a hexagonal system (wurtzite structure), a cubic system (rock salt structure) or a face-centered-cubic structure.

As far as the proportion of zinc oxide fine particles falls within the above range, the composite particles of the invention include those in which a metal element other than zinc, e.g., an alkali metal or an alkaline earth metal, forms, in the form of its atom or ion, a composite with zinc oxide crystals; those in which an inorganic compound of a metal element other than zinc, e.g., an oxide, a hydroxide, a sulfide, a nitride, a carbide or a carbonate, forms a solid solution in zinc oxide crystals; those in which an organometallic compound, such as a silane, aluminum, zirconium or titanium coupling agent, an organosiloxane or a chelate compound, is bound to the surface of the zinc oxide crystals or forms a coating layer on the surface of the zinc oxide crystals; and those containing a halogen element, an inorganic acid radical (e.g., a sulfuric acid radical and a nitric acid radical) or an organic compound residue (e.g., a fatty acid residue, an alcohol residue or an amine residue) in the inside and/or on the surface thereof. The total weight of the zinc oxide fine particles and a polymer is preferably 75 to 100% by weight, still preferably 85 to 100% by weight. If the total weight is lower than 75%, there is a tendency that the UV screening power per composite fine particle reduces and the composite particles have insufficient mechanical strength for practical use.

The composite particles of the invention are not particularly limited in shape and size.

Of the composite particles of the invention, those having a number average particle size of 0.1 to 10 µm, the particle size being based on the major axis (L), with a coefficient of size variation of not more than 30%, particularly a number average particle size of 0.1 to 2 µm with a coefficient or size variation of not more than 15%, are practically useful. If the number average particle size is smaller than 0.1 µm, the composite particles tend to have poor dispersibility. If it exceeds 10 µm, the composite particles, when formulated into coating compositions, tend to have poor dispersion stability. If the coefficient of particle size distribution is more than 30%, there is a tendency that the composite particles have reduced dispersibility and/or dispersion stability or, when coated or molded, a coating film or the surface of a molded article becomes non-uniform.

The composite particles of the invention can have, for example, a spherical shape, an ellipsoidal shape, a cylindrical shape, a column shape, a hexagonal prism shape, a spindle shape, a pyramidal shape or a cubic shape. Spherical and/or ellipsoidal composite particles are hardly broken by mechanical shear and are easily dispersed in coating compositions or resins. The term "spherical" as used herein means that the composite particle assumes a round shape as a whole with its L/B ratio (major axis (L)/minor axis (B)) being 1.0 or greater and smaller than 1.2. The term "ellipsoidal" as used herein means that the composite particle assumes a round shape as a whole with its L/B ratio being 1.2 to 5.0. Composite particles having an L/B ratio greater than 5.0 tend to have poor dispersibility in resins or be broken by mechanical shear. The major axis (L) is the longest of measured three axes of the composite particle, and the minor axis (B) is the smaller of the width and the height out of the three axes.

The zinc oxide fine particles may be dispersed uniformly throughout the composite particles or may aggregate partly and/or totally. When the zinc oxide fine particles aggregate to form an outer shell, the composite particles have a double layer structure in which the zinc oxide fine particles are localized in the outer shell. In this case, the composite particles exhibit high light scattering properties because, in addition to light scatter on the surface of the composite particles (corresponding to light scatter on conventional inorganic transparent fine particles), light are scattered on the surface of the zinc oxide fine particles within the composite particles and also on the interface between the outer shell and the inner shell. In particular, when the zinc oxide fine particles constituting the composite particles have an average particle size of 0.005 to 0.1 µm, especially 0.005 to 0.05 µm, and the composite particles have an average particle size of 0.1 to 5 µm, the composite particles exhibit high diffusing properties while having high light transmitting properties. The thickness of the outer shell formed by aggregation of zinc oxide fine particles is not particularly limited but is preferably at a ratio of 0.1 to 0.4 to the number average particle size of the composite particles. If the thickness ratio is smaller than the above range, the composite particles tend to have reduced mechanical strength. If it exceeds the above range, the expected effects of the double layer structure may not be fully manifested.

The zinc oxide fine particles are not particularly limited in shape and size but must be smaller than the composite particles. For example, when the composite particles have a number average particle size of 0.1 to 10 µm (preferably 0.1 to 2 µm), the number average particle size of the zinc oxide fine particles is 0.005 to 0.1 µm, corresponding to $\frac{1}{10}$ to $\frac{1}{1000}$ of that of the composite particles. If the number average particle size of the zinc oxide fine particles is smaller than that range, the ultraviolet screening power of the zinc oxide fine particles tends to be reduced. If it exceeds the above range, light transmitting properties tend to be reduced. If the ratio of the number average particle size of the zinc oxide fine particles to that of the composite particles is less than the above range, the UV screening power of the zinc oxide fine particles tend to be reduced. If the ratio exceeds the above range, the composite particles tend to have insufficient mechanical strength for practical use, or the composite effects tend to be exerted unsuccessfully.

Where the zinc oxide fine particles aggregate to form an outer shell, the polymer can be present only in the outer shell or the inner shell or both of them. It is preferable that the polymer be present only in the outer shell so that the composite particles are hollow. Hollow composite particles have an improved light diffusing function. In particular, hollow composite particles having an average particle size of 0.1 to 5 µm in which the zinc oxide fine particles have an average particle size of 0.005 to 0.1 µm, particularly 0.005 to 0.05 µm, have high light transmitting properties and extremely high light diffusing properties and are therefore useful as particles of a diffuser for back-lighting liquid crystal displays as hereinafter described. Where the polymer is present in the outer shell, covering the surface of the composite particles, such composite particles have excellent dispersibility and, when formulated into a resin composition, exhibit increased adhesion to a matrix polymer. Where the composite particles have many interstices among zinc oxide fine particles, and also where the composite particles are hollow, such composite particles perform functions as porous particles or microcapsules. That is, they have functions of adsorption, separation, removal, and collection, such as oil absorptivity, hygroscopicity, harmful metal ion adsorptivity, harmful gas and bad order absorptivity; heat and sound insulating functions (e.g., heat insulating fillers or sound insulating fillers); a function of immobilizing metal ions, enzymes or bacteria (e.g., catalytic carriers and fillers for chromatography); light weight properties; and a function of slowly releasing a liquid or perfume held therein.

The polymer to be used in the composite particles of the invention is not particularly limited and can be, for example, polymers having a weight average molecular weight of 1000 to 1,000,000, including those generally called oligomers or prepolymers. Since such polymers are easily dissolved or easily emulsified or suspended as finely as possible in the first or second mixture or in the heating system for precipitating the composite particles, composite particles regular in size (a coefficient of particle size variation of not more than 30%) and shape can be obtained easily. The polymer to be used in the composite particles can be at least one resin selected from the following groups (a) to (n). When these resins are used, composite particles having an average particle size of 0.1 to 10 µm are obtained easily.

(a) Acrylic Resin Polymers (1) Thermoplastic acrylic resins, for example, homo- or copolymers of (meth)acrylic monomers, such as acrylic esters and methacrylic esters; copolymers of the above-described (meth)acrylic monomers and other polymerizable monomers having no functional group, such as maleic esters, itaconic esters, vinyl monomers (e.g., styrene, p-chlorostyrene, vinyltoluene, vinyl acetate, vinyl chloride, vinyl methyl ether, and vinyl butyral), olefins (e.g., ethylene and propylene), dienes (e.g., butadiene), and trienes; and modified resins or derivatives (e.g., with substituents introduced) of these acrylic resins and (2) thermosetting acrylic resins, such as copolymers of the above-described (meth)acrylic monomers and other polymerizable monomers having a functional group, such as acrylic acid, methacrylic acid, acrylamide, methacrylamide, acrylonitrile, methacrylonitrile, hydroxyalkyl esters of (meth)acrylic acid, glycidyl (meth)acrylate, and aminoalkyl esters of (meth) acrylic acid; copolymers of the above-described polymerizable monomers having a functional group, the above-described (meth)acrylic monomers, and the above-described polymerizable monomers having no functional group, and modified resins or derivatives (e.g., with substituents introduced, or with the functional group neutralized) of these acrylic resins.

(b) Alkyl Resin Polymers

Polycondensates (oil-free alkyl resins) obtained from polybasic acids (e.g., phthalic anhydride, isophthalic acid, terephthalic acid, benzoic acid, rosin, adipic acid, maleic anhydride, succinic acid, sebacic acid, fumaric anhydride, trimellitic acid, and pyromellitic acid) and polyhydric alcohols (e.g., ethylene glycol, propylene glycol, neopentyl glycol, 1,6-hexanediol, glycerol, trimethylolethane, pentaerythritol, diethylene glycol, dipropylene glycol, triethylene glycol, polyethylene glycol, polypropylene glycol, and hydrogenated bisphenol A); modified alkyd resins obtained by modifying the above-described polycondensates with fats and oils (e.g., fatty acids); modified alkyd resins obtained by modifying the above-described polycondensates or modified alkyd resins with natural resins (e.g., rosin), synthetic resins (e.g., phenolic resins, epoxy resins, urethane resins, silicone resins, and amino resins) or the monomers described in (a) above, such as rosin-modified alkyd resins, phenol-modified alkyd resins, epoxy-modified alkyd resins, styrenated alkyl resins, acryl-modified alkyl resins, urethane-modified alkyd resins, silicone-modified alkyd resins, and amino resin-modified alkyd resins; and derivatives of the above-described polycondensates, alkyd resins or modified alkyd resins, such as those having part or the whole of the functional group thereof (e.g., a carboxyl group) neutralized, or with a substituent introduced.

(c) Amino Resin Polymers

Melamine resins, such as melamine-formaldehyde resins, butylated melamine resins, methylated melamine resins, and benzoguanamine resins; urea resins, such as urea-formaldehyde resins, butylated urea resins, and butylated urea-melamine resins; amino resin-modified alkyd resins obtained by modifying the alkyd resins described in (b) above with melamine resins or urea resins through co-condensation reaction; and modified resins of the above-described melamine resins, urea resins or amino resin-modified alkyd resins, such as methylated methylolmelamine, an adduct of an initial condensate of methylolmelamine and a polyhydric alcohol, condensates between melamine or urea and a polyamine, butylated melamine having introduced therein a hydrophilic group, and amino resins using benzoguanamine having introduced therein a hydrophilic group.

(d) Vinyl Resin Polymers

Homo- and copolymers of vinyl monomers (e.g., vinyl chloride, vinyl acetate, vinyl propionate, vinylidene chloride, vinyl butyral, styrene, p-chlorostyrene, and vinyltoluene), such as polyvinyl chloride, vinyl chloride-vinyl acetate copolymers, polyvinyl acetate, ethylene-vinyl acetate copolymers, modified ethylene-vinyl acetate copolymers, polyvinyl butyral, polyvinyl alcohol, and polystyrene; copolymers of the vinyl monomers and other unsaturated monomers, such as olefins (e.g., ethylene and propylene), dienes (e.g., butadiene), and trienes; copolymers of the vinyl monomers and the above-described (meth) acrylic monomers and/or other unsaturated monomers; and derivatives of these copolymers.

(e) Epoxy Resin Polymers

Glycidyl ether epoxy resins, such as bisphenol A epoxy resins, phenoxy resins (high-molecular weight ($\geq$30,000) bisphenol A epoxy resins), phenol novolak epoxy resins, o-cresol novolak epoxy resins, bisphenol A novolak epoxy resins, brominated phenol novolak epoxy resins, and tetraphenylolethane epoxy resins; glycidyl ester epoxy resins; glycidylamine epoxy resins; epoxidized polybutadiene; and polymers obtained by reacting these epoxy resins with compounds having active hydrogen capable of crosslinking with an epoxy group (e.g., an amino group, a carboxyl group, an amido group or a thiol group) and/or (pre) polymers thereof (e.g., aliphatic (poly)amines, aromatic (poly)amines, diethylaminopropylamine, alicyclic amines, and polymercaptan).

(f) Polyamide Resin Polymers

Nylon resins obtained by polycondensation of diamines and dicarboxylic acids (e.g., nylon 66), nylon resins obtained by ring-opening polymerization of lactams (e.g., nylon 6), polypeptides obtained by polycondensation of amino acids (e.g., polyglycine and poly($\alpha$-L-alanine)), and amide derivatives of polyamines, which may retain an amino group, obtained by dehydrating condensation of polycarboxylic acids (typified by polymerized fatty acids (dimer acids) which are polymers of vegetable fat and oil fatty acids) and polyamines (e.g., ethylenediamine and diethylenepolyamine).

(g) Polyimide Resin Polymers

Polyimide polymers obtained by polycondensation of tetracarboxylic acid dianhydrides (e.g., pyromellitic anhydride) and aromatic diamines, Diels-Alder polymerization of bismaleimides (e.g., bishexamethylenemaleimide) and biscyclopentadienyl compounds or 2,5-dimethyl-3,4-diphenylcyclopentadienone, etc., or the like reaction.

(h) p-Polyurethane Resin Polymers

Resins having a urethane bond in the molecule thereof, such as alkyd resins with the dibasic acid thereof being substituted with a diisocyanate; polymers obtained by reacting an acrylic polymer comprising a monomer containing a hydroxyl-containing (meth)acrylic monomer (e.g., methacrylic acid hydroxy-ester) and an isocyanate compound; polymers obtained by reacting a polyester polymer comprising a dibasic acid and an excess polyvalent alcohol and an isocyanate compound; polymers obtained by reacting a polyalkylene glycol (obtained by addition polymerization of a polyhydric alcohol and propylene oxide or ethylene oxide) with an isocyanate compound; polymers obtained by reacting a hydroxyl-containing epoxy resin with an isocyanate compound; polyurethane resins conventionally used in coatings, such as moisture-curing polyurethane reins, heat-curing polyurethane resins, and catalytic curing polyurethane resins; prepolymers having a urethane bond and a polymerizable double bond, such as phenyl glycidyl ether acrylate-hexamethylene diisocyanate urethane prepolymer, phenyl glycidyl ether acrylate-isophorone diisocyanate urethane prepolymer, phenyl glycidyl ether acrylate-tolylene diisocyanate urethane prepolymer, glycerol dimethacrylate-hexamethylene diisocyanate urethane prepolymer, glycerol dimethacrylate-isophorone diisocyanate urethane prepolymer, pentaerythritol triacrylate-hexamethylene diisocyanate urethane prepolymer, pentaerythritol triacrylate-isophorone diisocyanate urethane prepolymer, and pentaerythritol triacrylate-tolylene diisocyanate urethane prepolymer; homo- or copolymers of these prepolymers; copolymers of these prepolymers and other polymerizable monomers, such as (meth)acrylic monomers (e.g., (meth)acrylic acid, (meth)acrylic esters, (meth)acrylonitrile, and (meth)acrylamide), maleic acid, maleic esters, styrene monomers (styrene, p-chlorostyrene, and vinyltoluene), olefins (e.g., ethylene and propylene), dienes (e.g., butadiene), trienes, and vinyl monomers (e.g., vinyl acetate, vinyl chloride, vinyl methyl ether, vinyl alcohol, and vinyl butyral); and urethane acrylate polymers obtained by reacting polyisocyanate (e.g., hexamethylene diisocyanate and toluylene diisocyanate) and (meth)acrylic acid or (meth) acrylic acid oligomers.

(i) Polyester resin polymers

Saturated or unsaturated polyester polymers obtained by polycondensation between at least one glycol selected from the group consisting of aliphatic glycols (e.g., ethylene glycol, diethylene glycol, propylene glycol, dipropylene glycol, 1,3-butanediol, 1,6-hexanediol, and neopentyl glycol), aromatic diols (e.g., hydroquinone and resorcin), and polyalkylene glycols (e.g., polyethylene glycol and polypropylene glycol), etc. and at least one dicarboxylic acid selected from the group consisting of aromatic dicarboxylic acids (e.g., phthalic acid (anhydride), isophthalic acid, terephthalic acid, and naphthalenedicarboxylic acid), aliphatic dicarboxylic acids (e.g., adipic acid and sebacic acid), alicyclic dicarboxylic acids (e.g., cyclohexane-1,4-dicarboxylic acid), and unsaturated dicarboxylic acids (e.g., maleic acid (anhydride) and fumaric acid), etc.; and polymers obtained by polymerization of an unsaturated polyester with a polymerizable monomer (e.g., styrene and (meth) acrylic esters).

(j) Phenolic Resin Polymers

Phenolic resins generally termed novolak type or resol type, which are obtained by polycondensation between phenols (e.g., phenol, an alkyl-substituted phenol, an allyl-substituted phenol, and bisphenol A) and formaldehyde; and derivatives thereof obtained by modification or substitution.

(k) Organopolysiloxane Polymers

Polymers comprising a siloxane skeleton and containing a carbon-containing organic group (e.g., an alkyl group) directly bonded to the silicon atom of the siloxane bond, such as polyalkylsiloxanes (e.g., dimethylpolysiloxane and methylphenylpolysiloxane); and the above-described polymers with part of the organic group bonded to the silicon atom via an oxygen atom or part of the organic group modified (modified silicone) (e.g., alkyd-modified silicone, epoxy-modified silicone, polyester-modified silicone, acryl-modified silicone, and urethane-modified silicon).

(l) Acrylic Silicone Resin Polymers

Polymers obtained by copolymerizing organosilicon compounds having a polymerizable double bond (e.g., methacryloxypropyltrimethoxysilane and vinyltrimethoxysilane) and unsaturated monomers (e.g., acrylic monomers), such as acrylic copolymers containing an alkoxysilyl group.

(m) Fluorine Resin Polymers

Homo- or copolymers of fluorine-containing polymerizable monomers, such as ethylene fluoride, vinylidene fluoride, and vinyl fluoride; and copolymers comprising the fluorine-containing polymerizable monomers and other polymerizable monomers, such as vinyl monomers, olefins, and acrylic monomers.

(n) Other Resin Polymers

Conventional resins, such as xylene resins, petroleum resins, ketone resins, liquid polybutadiene, rosin-modified maleic acid resins, and coumarone resins; and derivatives of these resins.

Preferred polymers are those having at least one polar atomic group for the reason that the composite fine particles containing such polymers are excellent in chemical stability (solvent resistance and chemical resistance) and mechanical characteristics. Preferred polar atomic groups can be at least one group selected from the group consisting of a carboxyl group, an amino group (inclusive of a primary amino group, a secondary amino group, a tertiary amino group, an imino group, and an imino bond), a quaternary ammonio group, an amido group, an imido bond, a hydroxyl group (alcoholic or phenolic), a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group. Use of the polymers containing these polar groups brings about the following advantages: the resulting composite particles have further improved chemical stability and excellent mechanical strength, such as crush strength; fine zinc oxide particles having an average particle size of 0.005 to 0.1 $\mu$m can easily be obtained; and the composite particles having uniform particle size (coefficient of particle size distribution of not more than 30%) and uniform shape can easily be obtained.

Polymers having one or more carboxyl groups include homo- or copolymers of carboxyl-containing polymerizable monomers, such as (meth)acrylic acid, 2-(meth) acryloyloxyethylsuccinic acid, 2-(meth) acryloyloxyethylphthalic acid, 2-acryloyloxyethylhexahydrophthalic acid, and maleic acid; copolymers of the above-described carboxyl-containing polymerizable monomers and other polymerizable monomers, such as (meth)acrylic monomers (e.g., (meth) acrylic esters, (meth)acrylamide, and (meth)acrylonitrile), substituted (meth)acrylic monomers (e.g., methyl α-chloromethacrylate), maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, vinyl butyral, and vinyl alcohol), and polymerizable organosilicon compounds (e.g., vinyltrimethoxysilane and methacryloxytrimethoxysilane); polymers having a carboxyl group at the terminal or side chain thereof, selected from the above-described alkyd resin polymers and polyester resin polymers; and carboxyl-modified organopolysiloxane polymers containing a carboxyl group at the terminal and/or side chain thereof, such as dimethylpolysiloxane having a carboxypropyl group at the terminal or side chain thereof.

The polymers having one or more amino groups and/or quaternary ammonio groups are polymers having at least one group selected from the group consisting of a primary amino group, a secondary amino group, a tertiary amino group, an imino group, an imino bond, and a quaternary ammonio group. Examples of such polymers include homo- or copolymers of amino-, imino- or ammonio-containing polymerizable monomers, such as dimethylaminoethyl methacrylate, diethylaminoethyl methacrylate, 4-vinylpyridine, p-aminostyrene, 3-vinylaniline, 4-vinylimidazole, vinylpyrrole, and dimethyldiallylammonium chloride; copolymers of the above-described monomers and other polymerizable monomers, such as (meth) acrylic monomers (e.g., (meth)acrylic acid, (meth)acrylic esters, (meth)acrylamide, and (meth)acrylonitrile), substituted (meth)acrylic monomers (e.g., methyl α-chloromethacrylate), maleic acid, maleic esters, styrene monomers (e.g., styrene, p-chlorostyrene, arLd vinyltoluene), olefins (e.g., ethylene and propylene), dienes (e.g., butadiene), trienes, vinyl monomers (e.g., vinyl acetate, vinyl chloride, vinyl methyl ether, vinyl butyral, and vinyl alcohol), and polymerizable organosilicon compounds (e.g., vinyltrimethoxysilane and methacryloxytrimethoxysilane); amino-containing polymers selected from the above-described polyamide resin polymers; the above-described amino resin polymers; amino-modified organopolysilane polymers having an amino group at the terminal and/or side chain thereof, such as dimethylpolysiloxane having a dimethylamino group or an aminopropyl group at the terminal or side chain thereof; alkyleneimine polymers, such as polyethyleneimine and polypropyleneimine; polymers of pyrrolidine, piperidine, etc.; halogenated polydiallylammonium; ionene compounds; chitosan; and porphines, such as tetramethylporphine and tetraphenylporphine.

The polymers having one or more amido groups include homo- or copolymers of amido-containing polymerizable monomers, such as (meth)acrylamide and 2-acrylamido-2-methylpropanesulfonic acid; copolymers of these monomers and other polymerizable monomers, such as (meth)acrylic monomers (e.g., (meth)acrylic acid, (meth)acrylic esters, and (meth)acrylonitrile), substituted (meth)acrylic monomers (e.g., methyl α-chloromethacrylate), maleic acid, maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, vinyl butyral, and vinyl alcohol), and polymerizable organosilicon compounds (e.g., vinyltrimethoxysilane and methacryloxytrimethoxyhsilane); the above-described polyamide resin polymers; and amido-modified organopolysiloxane polymers having an amido group at the terminal and/or side chain thereof.

The polymers having one or more imido bonds include the above-described polyimide resin polymers.

The polymers having one or more alcoholic hydroxyl groups include homo- or copolymers of hydroxyl-containing polymerizable monomers, such as 2-hydroxyethyl (meth) acrylate, 2-hydroxypropyl (meth)acrylate, 2-hydroxybutyl (meth)acrylate, glycerol dimethacrylate, glycerol monomethacrylate, 3-chloro-2-hydroxypropyl methacrylate, 2-acryloyloxyethyl-2-hydroxyethylphthalic acid, pentaerythritol triacrylate, 2-hydroxy-3-phenoxypropyl acrylate, bisphenol A-diepoxy-(meth)acrylic acid adducts, and vinyl alcohol; copolymers of these monomers and other polymerizable monomers, such as (meth)acrylic monomers (e.g., (meth)acrylic acid, (meth)acrylic esters, (meth) acrylonitrile, and (meth)acrylamide), substituted (meth) acrylic monomers (e.g., methyl α-chloromethacrylate), maleic acid, maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, and vinyl butyral), and polymerizable organosilicon compounds (e.g., vinyltrimethoxysilane and methacryloxytrimethoxysilane); cellulose polymers, such as hydroxypropyl cellulose, methyl cellulose, and hydroxyethylmethyl cellulose; polyamide resin polymers obtained by condensation of polybasic acids, such as aliphatic dicarboxylic acids, and polyamines; and organopolysiloxane polymers containing an alcoholic hydroxyl group at the terminal and/or side chain thereof, such as dimethylpolysiloxane or polydimethyl-hydroxyalkylene oxide methylsiloxane having carbinol or hydroxypropyl at the terminal thereof.

The polymers having one or more phenolic hydroxyl groups include the above-described phenolic resin polymers.

The polymers having one or more carboxylic acid ester bonds include homo- or copolymers of carboxylic acid ester-containing polymerizable monomers, such as (meth) acrylic esters (e.g., methyl methacrylate, ethyl methacrylate, butyl methacrylate, isobutyl methacrylate, isoamyl acrylate, 2-ethylhexyl methacrylate, isodecyl methacrylate, n-lauryl (meth)acrylate, benzyl acrylate, tridecyl methacrylate, n-stearyl (meth)acrylate, isooctyl acrylate, isostearyl methacrylate, behenyl methacrylate, butoxyethyl acrylate, methoxydiethylene glycol methacrylate, n-butoxyethyl methacrylate, 2-phenoxyethyl (meth)acrylate, methoxydiethylene glycol acrylate, methoxypolyethylene glycol methacrylate, cyclohexyl methacrylate, tetrahydrofurfuryl (meth)acrylate, isobornyl (meth)acrylate, benzyl methacrylate, ethylene glycol dimethacrylate, diethylene glycol dimethacrylate, 1,4-butanediol dimethacrylate, 1,6-hexanediol dimethacrylate, trimethylolpropane tri(meth) acrylate, glycerol dimethacrylate, trifluoroethyl methacrylate, pentaerythritol triacrylate, pentaerythritol tetraacrylate, dipentaerythritol hexaacrylate, neopentyl glycol acrylbenzoate, 3-acryloyloxyglycerol monomethacrylate propylene oxide-modified bisphenol A diacrylate, hydrogenated dicyclopentadienyl diacrylate, and perfluorooctylethyl acrylate), maleic esters (e.g., methyl maleate and butyl maleate), vinyl acetate, and methacryloxypropyltrimethoxysilane; copolymers of these monomers and other polymerizable monomers, such as (meth)acrylic monomers (e.g., (meth)acrylic acid, (meth)acrylonitrile, and (meth) acrylamide), maleic acid, styrene monomers (e.g., styrene, p-chlorostyrene, and vinyltoluene), olefins (e.g., ethylene and propylene), dienes (e.g., butadiene), trienes, vinyl monomers (e.g., vinyl chloride, vinyl methyl ether, vinyl alcohol, and vinyl butyral), and polymerizable organosilicon compounds (e.g., vinyltrimethoxysilane); the above-described polyester resin polymers; and organopolysiloxane polymers containing an ester bond at the terminal and/or side chain thereof, such as dimethylpolysiloxane having an acetoxy group, a stearyloxy group, etc. at the terminal thereof.

The polymers having one or more urethane groups and/or urethane bonds include the above-described polyurethane resin polymers.

The polymers having one or more ureido groups and/or ureylene bonds include polyurea obtained by polycondensation of nonamethylenediamine and urea.

The polymers having one or more isocyanate groups include polymethylenepolyphenyl polyisocyanate; polyol-modified isocyanates; and polymers obtained by reacting a polyfunctional aromatic or aliphatic isocyanate compound (e.g., hexamethylene diisocyanate or toluylene diisocyanate) with a (pre)polymer containing a functional group having active hydrogen (e.g., a amino group, a carboxyl group or a hydroxyl group) (reaction between part of the isocyanate groups contained in the isocyanate compound with the functional group having active hydrogen).

The polymers having one or more epoxy groups include homo- or copolymers of epoxy-containing polymerizable monomers, such as epoxy-containing (meth)acrylic monomers (e.g., glycidyl methacrylate, N-[4-(2,3-epoxypropoxy)-3,5-dimethylbenzyl]acrylamide); copolymers of these monomers and other polymerizable monomers which are inert to the epoxy group during polymerization, such as (meth)acrylic monomers (e.g., (meth)acrylic esters), substituted (meth)acrylic monomers (e.g., methyl α-chloromethacrylate), maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, vinyl butyral, and vinyl alcohol), and polymerizable organosilicon compounds (e.g., vinyltrimethoxysilane and methacryloxytrimethoxysilane); the above-described epoxy resin polymers; and organopolysiloxane polymers containing a glycidoxy group at the terminal and/or side chain thereof, such as polydimethylsiloxane, polyglycidoxypropylmethylsiloxane, and polyglycidoxypropylmethyl-dimethylsiloxane copolymer having a glycidoxypropyl group at the terminal thereof.

The polymers having one or more phosphoric acid groups include homo- or copolymers of phospho-containing polymerizable monomers, such as mono(2-methacryloyloxyethyl) acid phosphate, mono(2-acryloyloxyethyl) acid phosphate, and 2-acryloyloxyethyl acid phosphate; and copolymers of these monomers and other polymerizable monomers, such as (meth)acrylic monomers (e.g., (meth)acrylic acid, (meth)acrylic esters, (meth)acrylonitrile, and (meth)acrylamide), substituted (meth)acrylic monomers (e.g., methyl α-chloromethacrylate), maleic acid, maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, vinyl alcohol, and vinyl butyral), and polymerizable organosilicon compounds (e.g., vinyltrimethoxysilane and methacryloxytrimethoxysi lane).

The polymers having one or more metallic hydroxyl groups and/or metallic alkoxy groups include copolymers of a silicon compound having a polymerizable double bond, such as methacryloxypropyltrimethoxysilane, and other polymerizable monomers, such as (meth)acrylic monomers (e.g., (meth)acrylic acid, (meth)acrylic esters, (meth)acrylonitrile, and (meth)acrylamide), substituted (meth) acrylic monomers (e.g., methyl α-chloromethacrylate), maleic acid, maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, and vinyl methyl ether), and polymerizable organosilicon compounds (e.g., vinyltrimethoxysilane and methacryloxytrimethoxysilane); polymers obtained by (partially) hydrolyzing the alkoxysilyl group of the above-described copolymers; silanol-containing organopolysiloxanes, such as silanol-terminated polydimethylsiloxane, silanol-terminated polydiphenylsiloxane, and silanol-terminated polydimethyl-diphenylsiloxane or polytetramethyl-p-silphenylenesiloxane; (N-trimethoxysilylpropyl) polyethyleneimine, (N-trimethoxysilylpropyl)-o-polyethylene oxide urethane, triethoxysilyl-modified poly(1, 2-butadiene), and these polymers with the alkoxysilyl group thereof being partially hydrolyzed; and the above-described acrylic silicone resin polymers.

The polymers having one or more sulfonic acid groups include homo- or copolymers of sulfo-containing polymerizable monomers, such as acrylamidomethanesulfonic acid, 2-acrylamido-2-methylpropanesulfonic acid, and a sodium salt thereof; copolymers of these monomers and other polymerizable monomers, such as (meth)acrylic monomers (e.g., (meth)acrylic acid, (meth)acrylic esters, (meth)acrylonitrile, and (meth)acrylamide), substituted (meth)acrylic monomers (e.g., methyl α-chloromethacrylate), maleic acid, maleic esters, styrene monomers (e.g., styrene, p-chlorostyrene, and vinyltoluene), olefins (e.g., ethylene and propylene), dienes (e.g., butadiene), trienes, vinyl monomers (e.g., vinyl acetate, vinyl chloride, vinyl methyl ether, vinyl butyral), and polymerizable organosilicon compounds (e.g., vinyltrimethoxysilane and methacryloxytrimethoxysilane); and sulfo-containing polymers obtained by reacting styrene polymers with a sulfonating agent, e.g., concentrated sulfuric acid, chlorosulfonic acid or sulfuric anhydride.

The polymers having other polar atomic groups include ring-opened compounds of cyclic iminoethers (e.g., (2-) substituted oxazoline and/or (2-substituted)oxazine), such as poly-N-formylethyleneimine or poly-N-acetylethyleneimine which is obtained by ring-opening polymerization of oxazoline or 2-methyloxazoline; polymers obtained by adsorptive coordination of metallic ions to part or all of the ligands (functional groups) of polymers having such a structure as is used in chelate resins, i.e., polymers (amongst polymers having at least one functional group) having a ligand (functional group) to which a metallic ion can coordinate (e.g., polyvinyl alcohol, polyvinyltriacrylmethane, polyvinylmethacryloylacetone, poly(4-hydroxystyrene), pyrogallolphenol-formaldehyde resin, salicylic acid-formaldehyde resin, polyvinylsalicylic acid, polyacrylic acid, polymethacrylic acid, polyitaconic acid, aminophenol-formaldehyde resin, poly(8-hydroxy-5-vinylquinoline), polyvinylamine, polyethyleneimine, poly(4-aminostyrene), poly(3-vinylaniline), poly(4-vinylpyridine), poly(4-vinylbipyridine), poly(4-vinylimidazole), polyvinylpyrrole, polyglycine, and poly(α-L-alanine)), for example, ring-opening copolymers obtained from cyclic iminoethers and lactones, such as an oxazoline-β-propiolactone alternating copolymer); and polymers having a carboxyl group, a sulfonic acid group, etc. in the form of its salt with a metal, e.g., an alkali metal (e.g., sodium or potassium) or an alkaline earth metal (e.g., magnesium or calcium).

Of the polymers illustrated in (a) through (n), those having at least one main chain selected from the group consisting of a (meth)acrylic unit, a styrene unit, a vinyl unit or combinations of these units, an alkyd chain, a polyester chain, and a polyamide chain and at least one polar atomic group selected from the group consisting of a carboxyl group, an amino group, an amido group, a silanol group, and an alkoxysilyl group are preferred for ease of obtaining double-layered, hollow, and spherical composite fine particles. The amount of the polymer to be used, the equivalent amount of the polar atomic group, and the composition of the reaction system for the formation of the composite fine particles (e.g., the composition of the solvent) should be selected appropriately in accordance with the kind of the polymer.

The composite particles of the invention are not limited in manner of use as long as the temperature of use is below the thermal decomposition point of the polymer constituting the composite particles. For example, the composite particles can not only be compounded into those resins which are molded at high temperatures, such as polyesters and polycarbonates, but can be applied to the surface of glass with the aid of an inorganic binder to form a coating film, which can then be heated at a high temperature.

The process for producing the zinc oxide-polymer composite particles of the invention will further be illustrated in more detail.

While the process for producing the composite particles of the invention is not particularly restricted, the process hereinafter described (i.e., the process of the invention) achieves high productivity.

According to the process of the invention, a mixture comprising a zinc source, a carboxyl-containing compound, a polymer, and an alcohol-containing solution is kept at a temperature of 100° C. or higher to thereby precipitate zinc oxide-polymer composite particles containing zinc oxide fine particles and the polymer.

Useful zinc sources and preferred examples thereof can be those previously described with respect to the process for producing zinc oxide fine particles as described in (1) to (9) above. Particularly preferred amongst them are zinc oxide and/or zinc hydroxide because of their availability at low prices and freedom of choice of the carboxyl-containing compound to be combined with.

The amount of the zinc source to be used is usually 0.1 to 95% by weight, preferably 0.5 to 50% by weight, still preferably 1 to 30% by weight, in terms of ZnO, based on the total charged amount of the zinc source, the carboxyl-containing compound, and the alcohol. If the zinc source is less than the above range, the productivity tends to decrease. If it is more than the above range, the composite particles tend to undergo secondary agglomeration, hardly providing finely dispersed composite particles with a regular particle size distribution.

Useful carboxyl-containing compounds and preferred examples thereof can be those previously described with respect to the process for producing zinc oxide fine particles as described in (1) to (9) above. Monocarboxylic acids are particularly preferred.

The monocarboxylic acids for use in the invention are compounds containing one carboxyl group per molecule. Specific examples of such compounds include saturated fatty acids (or saturated monocarboxylic acids), e.g., formic acid, acetic acid, propionic acid, isobutyric acid, caproic acid, caprylic acid, lauric acid, myristic acid, palmitic acid, and stearic acid; unsaturated fatty acids (or unsaturated monocarboxylic acids), e.g., acrylic acid, methacrylic acid, crotonic acid, oleic acid, and linolenic acid; cyclic saturated monocarboxylic acids, such as cyclohexanecarboxylic acid; aromatic monocarboxylic acids, e.g., benzoic acid, phenylacetic acid, and toluylic acid; anhydrides of these monocarboxylic acids, such as acetic anhydride; and halogen-containing monocarboxylic acids, such as trifluoroacetic acid, monochloroacetic acid, and o-chlorobenzoic acid. These compounds can be used either individually or as a combination of two or more thereof.

Preferred of the above monocarboxylic acids are saturated fatty acids having a boiling point of 200° C. or lower at atmospheric pressure. Preferred examples are formic acid, acetic acid, propionic acid, butyric acid, and isobutyric acid. With such compounds, it is easy to control the monocarboxylic acid content in the reaction system from mixing through heating, thus making it easy to strictly control the zinc oxide crystal precipitation reaction. It is preferable to use the above saturated fatty acid in a proportion of 60 to 100 mol %, particularly 80 to 100 mol %, in the total monocarboxylic acids. If the proportion is lower than the above range, the zinc oxide particles in the composite particles tend to have reduced crystalline properties.

The monocarboxylic acid to be used further includes monocarboxylic acid zinc salts, e.g., zinc acetate. When such a zinc salt is used as a zinc source, it is not always necessary to separately add the above-mentioned monocarboxylic acid.

The amount of the monocarboxylic acid to be used (or to be charged) for obtaining the first mixture is usually in a range of from 0.5 to 50 mol, preferably 2.2 to 10 mol, per mole of Zn atoms of the zinc source. This range is advantageous for the economy, ease of composite particle formation, ease of obtaining composite particles which hardly agglomerate and have excellent dispersibility. At a lower molar ratio to Zn, zinc oxide fine particles having satisfactory crystalline properties and composite particles having uniformity in shape and size tend to be hardly obtained. A higher molar ratio to Zn not only results in bad economy but shows tendency to a failure of obtaining composite particles having satisfactory dispersibility.

The alcohols to be used can be those previously described with respect to the process for producing zinc oxide fine particles as described in (1) to (9) above. Those having a boiling point of 120° C. or higher at atmospheric pressure are preferred of them; for fine particles of excellent crystalline properties can be obtained with ease under atmospheric pressure and in a short time. For ease of obtaining particles having excellent dispersibility, monohydric alcohols having a boiling point of 120° C. or higher and a water solubility of not less than 1% by weight at 20° C., for example, monoethers or monoesters of glycols and n-butanol, are especially preferred.

While the amount of the alcohol is not limited, a preferred molar ratio of the alcohol to Zn atoms originated in the zinc source is 1 to 100, particularly 5 to 80, so that the formation of zinc oxide fine particles may be completed in a short time period. At a lower molar ratio, zinc oxide fine particles with satisfactory crystalline properties are hardly obtained, or composite particles excellent in dispersibility and uniformity in particle shape and size are hardly obtained. At a higher molar ratio, an economical disadvantage may result.

The alcohol may be used as a mixed solvent with water or organic solvents other than alcohols, such as ketones, esters, aromatic hydrocarbons, and ethers. The amount of the alcohol in the alcohol-containing solution used for preparation of the second mixture is usually in a range of from 5 to 100% by weight, preferably 40 to 100% by weight, still preferably 60 to 100% by weight. If the proportion of the alcohol is lower than that range, composite particles satisfactory in crystalline properties, uniformity in shape and size, and dispersibility tend to be hardly obtained.

The polymers which can be used in the process of the invention are the same as those described with respect to the polymers constituting the composite particles of the invention.

While not limiting, the polymer is usually used in a weight ratio of 0.01 to 1.0 to the zinc atoms, in terms of zinc oxide, contained in the zinc source (i.e., Zn atoms contained in the second mixture). At a lower ratio, composite particles tend to be hardly obtained. At a higher ratio, precipitation of zinc oxide crystals tends to hardly occur, failing to obtain desired composite particles. While depending on the kind of the polymer or other reaction conditions, a preferred weight ratio of the polymer to zinc, in terms of zinc oxide, is 0.05 to 0.8 for obtaining composite particles having a double layer structure, uniform particle shape and size, and satisfactory dispersibility.

The process of the invention preferably comprises a first mixing step and a second mixing step. The first mixing step is a step in which the zinc source and the carboxyl-containing compound are mixed to prepare a first mixture containing zinc and the carboxyl-containing compound. The second mixing step is a step in which the first mixture and the alcohol are mixed to prepare a second mixture having zinc and the carboxyl-containing compound dissolved or dispersed in the medium.

According to the process of the invention, the polymer is added to any one or more of the first mixing step, the second mixing step, and a step of heating the second mixture to a temperature of 100° C. or higher. The polymer addition is conducted in any arbitrary stage before composite particles precipitate. For example, the polymer can be added to the first mixture during the first mixing step, to the second mixture during the second mixing step, or to the second mixture during the heating step.

The first mixing step is preferably a step in which the zinc source is dissolved in a mixed solvent of the carboxyl-containing compound and water to provide a first mixture in a solution state.

The second mixing step is preferably a step in which the first mixture is added to the alcohol maintained at 100° C. or higher to provide a second mixture.

When the first mixture comprising the zinc source and the carboxyl-containing compound is added to the alcohol, the first mixture is preferably a solution. It is still preferable that the zinc source and the carboxyl-containing compound are mutually dissolved or they are dissolved in a solvent having high compatibility with both of them. Water, alcohols, ketones, and esters are advantageous as such a solvent in that they easily dissolve the zinc source and the carboxyl-containing compound at a temperature of from room temperature up to about 100° C. and that they are also highly compatible with the alcohol. The term "alcohols" as used above embraces all the alcohol species hereinabove described.

Addition of the first mixture may be conducted at atmospheric pressure, under pressure, or under reduced pressure. Addition at atmospheric pressure is preferred from the economical viewpoint. In this case, when a dispersion of composite particles having uniformity in particle size and shape and excellent dispersibility is desired, it is preferable to keep the alcohol at 60° C. or higher, particularly 100° C. or higher, especially 100° C. to 300° C., during addition and mixing. If the temperature of the medium during addition and mixing is lower than 60° C., the viscosity of the second mixture tends to increase suddenly during or after addition and mixing, resulting in gelation. If this happens, there arise such problems that stirring is impossible and unsuccessfully achieves uniform mixing or heat conduction in the subsequent step, i.e., heating, is insufficient, resulting in temperature distribution. It follows that composite particles uniform in crystalline properties, particle size and particle shape can hardly be obtained. This problem also concerns the concentration of zinc in the second mixture and is more liable to occur at a higher zinc concentration. The lowest suitable temperature varies according to the pressure of the system. When the mixture is prepared under reduced pressure or under pressure, the temperature of the medium should be selected appropriately according to the pressure. When the first mixture is added to the medium while keeping the medium at a temperature within the above range, part of the carboxyl-containing compound and/or part of the alcohol may be driven out of the system through evaporation.

Addition of the first mixture to the alcohol can be carried out by adding the whole amount of the first mixture to the alcohol all at once, or adding the first mixture dropwise to the alcohol, or spraying the first mixture onto the alcohol. In particular, continuous or intermittent dropwise addition of the first mixture on or into the alcohol is preferred for obtaining highly dispersible composite particles at high productivity.

The thus prepared first mixture is added to the alcohol kept at, e.g., 60° C. or higher, preferably 100° C. or higher, still preferably 100 to 300° C., and mixed therewith to obtain the second mixture. In the preparation of the second mixture by addition of the first mixture to the medium, the first mixture is preferably added (by, for example, dropwise addition) while evaporating part of the volatile matter of the second mixture (e.g., the carboxyl-containing compound, the alcohol or water).

For obtaining a uniform mixture, the alcohol is preferably stirred while the first mixture is being added thereto.

The polymer can be added in any of the above-described steps but before formation of composite particles.

For smooth spread of the polymer throughout the reaction system, it is preferable for the polymer to be previously dissolved in the alcohol or be added to the reaction system as dissolved in an arbitrary solvent. The solvent for dissolving the polymer is not particularly limited as far as it is capable of dissolving the polymer, and can be selected from organic solvents, such as alcohols (the above-described ones), aliphatic or aromatic carboxylic acids, aliphatic or aromatic carboxylic acid esters, ketones, ethers, ether esters, aliphatic or aromatic hydrocarbons, and halogenated hydrocarbons; water, mineral oil, vegetable oil, wax oil, silicone oil, and the like.

The second mixture is not limited provided that it is a mixture obtained by mixing the above-described three essential components, i.e., a zinc source, a carboxyl-containing compound, and an alcohol, and the polymer is added thereto in any stage before formation of zinc oxide-polymer composite particles. If desired, the mixture may contain components other than the three components, such as water; organic solvents, e.g., ketones, esters, (cyclo)paraffins, ethers, and aromatic compounds; additives hereinafter described; metallic components other than zinc, e.g., inorganic metal salts (e.g., an acetate, a nitrate or a chloride) and organometallic alkoxides (e.g., metal alkoxides). The water or organic solvents are usually used as a solvent component.

The state of the second mixture is not particularly limited and may be a solution, sol, an emulsion, a suspension, etc.

On heating the thus obtained second mixture at 100° C. or higher, preferably 100 to 300° C., still preferably 150 to 200° C., for a period of 0.1 to 30 hours, preferably 0.5 to 10 hours, there are obtained composite particles of the present invention in accordance with practical productivity with the kinds and ratio of the raw materials. That is, on maintaining the second mixture at a temperature within the above range for a period within the above range, the zinc dissolved or dispersed in the medium is converted to X-ray crystallographically crystalline zinc oxide. Because the medium also has dissolved or dispersed therein the polymer, the polymer forms a composite while the nuclei of zinc oxide crystals precipitate and grow, thereby forming a dispersion containing zinc oxide-polymer composite particles. The internal structure, shape and size of the composite particles formed, and the particle size of the zinc oxide fine particles present therein can be controlled by selecting the kinds of the raw materials (e.g., the polymer and the alcohol) and by controlling the composition and temperature of the reaction system at the time when composite particles are formed through control of the composition of raw materials charged and the thermal history applied till composite particles are formed.

The existing state of the individual components in the second mixture is not particularly limited. In the reaction step wherein zinc dissolved or dispersed in the medium is converted to zinc oxide crystals, there are cases in which the reaction sometimes involves formation of one or more zinc oxide precursors. The case of using zinc oxide as a zinc source may be mentioned as an example. The term "zinc oxide precursors" means ions or compounds other than zinc oxide which contain at least a zinc atom. For example, the precursors include a zinc (hydrate) ion ($Zn^{2+}$), a polynuclear zinc hydroxide ion, and (basic) carboxylic acid salts, such as (basic) zinc acetate, (basic) zinc salicylate, and (basic) zinc lactate. The precursor may be present with a part or the whole thereof forming a composite with the carboxyl-containing compound and/or the alcohol as, for example, a complex salt.

To set the heating temperature of the second mixture within the above range brings about the advantage that strict control on the composition of the reaction system for obtaining zinc oxide fine particles, inclusive of control on the rate of evaporation of excessive or unnecessary components and the amount of evaporated components, can be taken easily. As a result, the particle size and the like of the resulting fine particles can be controlled easily. In the case when the first mixture is added to the above medium kept at 100° C. or higher to obtain the second mixture at 100° C. or higher, the resulting second mixture is maintaining at that temperature, or the mixture is heated or cooled to a prescribed temperature, followed by heating. In the case when the first mixture is added to the above medium below 100° C., the resulting second mixture is heated to 100° C. or higher.

In the stage when zinc in the second mixture is converted to zinc oxide fine particles, the carboxyl-containing compound in the second mixture does not change or partly or totally undergoes esterification with a part or the whole of the alcohol in the second mixture to form an ester compound.

In the step for obtaining the dispersion, the alcohol, the aforesaid ester compound produced on heating, or the solvent which may, if desired, have been added in the mixture may be removed by evaporation partially.

Where the second mixture contains water, it is preferable to evaporate the water to reduce the free water content of the resulting dispersion to 5% by weight or lower, particularly 1% by weight or lower. If the water content exceeds the above level, cases are sometimes met with that the zinc oxide crystals in the composite fine particles have reduced crystalline properties, resulting in a failure of fulfilling the function of zinc oxide, while such depends on the kinds of the other components present in the dispersion, such as the alcohol.

It is preferable that the amount of the carboxyl-containing compound in a finally obtained composite particle dispersion be 0.5 mol or less per mole of the total zinc atoms present in the dispersion. If it exceeds 0.5 mol, cases are sometimes met with that the zinc oxide fine particles have reduced crystalline properties, failing to fulfill the function of zinc oxide. Accordingly, where the amount of the carboxyl-containing compound present in the second mixture is such that the amount of the carboxyl-containing compound in the finally obtained dispersion will exceed 0.5 mol per mole of the total zinc atoms in the resulting dispersion, at least the excess should be removed by evaporation during the heating step Needless to say, the carboxyl-containing compound may be evaporated during heating even if the above molar ratio is 0.5 or lower.

Thus, the process of the invention provides a dispersion comprising 1 to 80% by weight of zinc oxide-polymer composite particles which contain zinc oxide fine particles and a polymer and have a number average particle size of 0.1 to 10 $\mu$m and a coefficient of particle size variation of not more than 30% (preferably a number average particle size of 0.1 to 5 $\mu$m and a coefficient of size variation of not more than 15%) in an alcohol and/or an ester compound and/or an organic solvent.

The dispersion of the composite particles obtained by the process of the invention can be used as such. If desired, the dispersion can easily be powdered or transformed to a dispersion of the composite particles in a different medium by solvent substitution.

Powder of zinc oxide can be obtained by separating the composite particles from the dispersion in a conventional manner, such as filtration, centrifugation or solvent evaporation, followed by drying or, if desired, calcination. A powdering method in which the dispersion (or a concentrated dispersion) is evaporated to remove the solvent by means of a vacuum flash evaporator is preferred for obtaining powdered composite particles having excellent dispersibility; for secondary agglomeration of the composite particles, which often occurs during drying, can be suppressed in this method.

A dispersion of the composite particles in a solvent different from that of the dispersion as produced by the process of the invention can be obtained by a known method comprising mixing the powder prepared by the above-described powdering method with a desired solvent such as water and dispersing the mixture with mechanical energy by means of a ball mill, a sand mill, an ultrasonic homogenizer, etc. A dispersion in a different solvent can also be prepared by mixing the dispersion as produced with a desired solvent while heating the dispersion to evaporate part or the whole of the solvent to be replaced (solvent substitution under heating). The solvent to be substituted for the initial one is not particularly limited and includes organic solvents, such as alcohols, aliphatic or aromatic carboxylic acid esters, ketones, ethers, ether esters, aliphatic or aromatic hydrocarbons, and halogenated hydrocarbons; water, mineral oil, vegetable oil, wax oil, silicone oil, and the like. A suitable solvent can be selected appropriately according to the end use.

In what follows, the process for producing inorganic compound particles having, on their surface, a cluster of thin plate like zinc oxide crystals with their tip projecting outward as described in (19) to (26) above and the inorganic compound particles as described in (43) to (49) above are explained.

The inorganic compound particles according to the invention contain 60 to 100% by weight of zinc oxide and have on their surface a cluster of thin plates whose tips projecting outward.

The process of the invention for producing the inorganic compound particles comprises maintaining a mixture of a zinc source and a carboxyl-containing compound dissolved or dispersed in a medium comprising at least an alcohol at a temperature of 100° C. or higher in the presence of lactic acid or a compound thereof thereby to precipitate inorganic compound fine particles containing 60 to 100% by weight of zinc oxide and having on the surface thereof a cluster of thin plate like zinc oxide crystals with their tips projecting outward.

The inorganic compound particles of the invention are not particularly limited in shape and size.

The shape of the inorganic compound particles is not particularly limited and can be, for example, a spherical or nearly spherical shape, a cylindrical shape, a column shape, a hexagonal prism shape, a spindle shape, a pyramidal shape or a cubic shape. Inorganic compound particles having at least one shape selected from a spherical shape and a nearly spherical shape are easily dispersed and hardly broken by mechanical shear when compounded into coating compositions or resins. The term "spherical" as used herein means that the particle assumes a round shape as a whole with its L/B ratio (major axis (L)/minor axis (B)) being 1.0 or greater and smaller than 1.2. The term "nearly spherical" as used herein means that the particle assumes a round shape as a whole with its L/B ratio being 1.2 to 5.0. Particles having an L/B ratio greater than 5.0 tend to be hardly dispersed in resins or be easily broken by mechanical shear. The major axis (L) is the longest of measured three axes of the inorganic compound particle, and the minor axis (B) is the smaller of the width and the height out of the three axes.

Of the inorganic compound particles of the invention, those having a number average particle size of 0.1 to 10 $\mu$m, the particle size being based on the major axis (L), with a coefficient of size variation of not more than 30%, particularly a number average particle size of 0.1 to 10 $\mu$m with a coefficient or size variation of not more than 15% are practically useful. If the number average particle size is smaller than 0.1 $\mu$m, the above-described effects of design and beautiful appearance may not be exerted. If it exceeds 10 $\mu$m, the particles, when formulated into coating compositions, tend to have poor dispersion stability. If the coefficient of particle size distribution is more than 30%, there is a tendency that the particles have reduced dispersibility.

The inorganic compound particles of the invention may be hollow. When the particles are hollow, the abnormal light scattering and transmitting characteristics become remarkable to provide an improved light filtering function. When the inorganic compound particles are hollow and/or have interstices among the thin plates, they exhibit improved adhesion to a matrix component or a matrix resin when formulated into a composition and perform functions as porous particles or microcapsules. That is, they have functions of adsorption, separation, removal, and collection, such as oil absorptivity, hygroscopicity, harmful metal ion adsorptivity, harmful gas and bad order absorptivity; heat and sound insulating functions (e.g., heat insulating fillers or sound insulating fillers); a function of immobilizing metal ions, enzymes or bacteria (e.g., catalytic carriers and fillers for chromatography); light weight properties; and a function of slowly releasing a liquid or perfume held therein.

The inorganic compound particles contain 60 to 100% by weight, preferably 80 to 100% by weight, of zinc oxide. If the proportion of zinc oxide is lower than 60%, the mechanical strength of the particles are reduced. The zinc oxide generally exhibits an X-ray diffraction pattern of any of a hexagonal system (wurtzite structure), a cubic system (rock salt structure), and a face-centered-cubic structure. Accordingly, as long as the amount of zinc atoms and oxygen atoms falls within the above range, the inorganic compound particles of the invention include those in which a metal element other than zinc, e.g., an alkali metal or an alkaline earth metal, forms, in the form of its atom or ion, a composite with zinc oxide crystals; those in which an inorganic compound of a metal element other than zinc, e.g., an oxide, a hydroxide, a sulfide, a nitride, a carbide or a carbonate, forms a solid solution in zinc oxide crystals; those in which an organometallic compound, such as a silane, aluminum, zirconium or titanium coupling agent, an organosiloxane or a chelate compound, is bound to the surface of the zinc oxide crystals or forms a coating layer on the surface of the zinc oxide crystals; and those containing a halogen element, an inorganic acid radical (e.g., a sulfuric acid radical and a nitric acid radical) or an organic compound residue (e.g., a fatty acid residue, an alcohol residue or an amine residue) in the inside and/or on the surface thereof.

The inorganic compound particles of the invention have a cluster of thin plates with their tips facing outward. As far as the thin plates constituting the cluster mainly comprise the inorganic compound as described above and have their tips facing outward, the structure of the cluster is not particularly limited. For example, the other end of the individual thin plates may be either separated from each other or be intimately close by cohesion, or the thin plates may be linked together at the portion mainly comprising the inorganic compound. It is preferable, however, that the thin plates mainly comprising the inorganic compound are stacked and/or gathered radially. In this case, the above-mentioned abnormal light transmission characteristics become appreciable to bring about enhanced effects of design and improved appearance.

The thin plates constituting the cluster are flat, having a flatness (major axis (l)/thickness (t)) of 2 to 200, preferably 4 to 100. If the flatness (l/t) is smaller than 2, the light filtering function, which is one of the characteristics based on the thin shape, tends to be reduced. If the flatness is greater than 200, the thin plates tend to have reduced mechanical strength. From the standpoint of industrial utility of the particles, the thin plates constituting the cluster preferably have a major axis (l) ranging from 5 to 1000 nm, particularly from 50 to 400 nm. If the major axis is shorter than 5 nm, the light filtering function, which is one of the characteristics based on the thin shape, tends to be reduced. If it exceeds 1000 nm, the thin plates tend to have reduced mechanical strength. The thin plates preferably have a thickness (t) ranging from 1 to 100 nm, particularly 2 to 50 nm. If the thickness is smaller than the above range, the thin plates tend to be broken mechanically. It if exceeds the above range, the visible light transmission tends to be reduced. The major axis (l) and the thickness (t) as referred to herein denote the length and the height of the three axes measured on the thin plate.

Since the inorganic compound particles of the invention contain 60 to 100% by weight of zinc oxide and have on their surface a cluster of thin plates having their tips outward, they have the following characteristics which were not possessed by conventional inorganic compound particles or zinc oxide fine particles.

(a) They have abnormal light scattering and transmitting properties (a transmitted light filtering function). They are therefore useful as an artistic filler with beautiful color.

(b) They scatter electromagnetic waves in the near infrared region without reducing the diffused transmission in the visible region. Therefore, they are useful as an infrared light-cutting filler having transparency.

(c) They are rich in surface unevenness.

It is desirable that all the inorganic compound particles of the invention have the same shape and the above-mentioned coefficient of particle size variation. A film having such particles dispersed therein has fine surface unevenness owing to the individual fine particles projecting on the surface of the film. In addition, because the particles are relatively regular in size and shape, the particles are well dispersed in the film without aggregating. As a result, the projections comprising the particles on the surface of the film are relatively regular in size to give uniform surface unevenness and also provide the surface with slip properties or anti-blocking properties without impairing surface flatness. When the inorganic compound fine particles of the invention are used like this, they exhibit excellent adhesion to a matrix resin (of a film) or a binder component (of a coating film) through the anchor effect of their surface unevenness. Thus, the particles can get rid of the problem of fall-off which has been accompanied by conventional spherical particles having a smooth surface.

The inorganic compound particles of the invention additionally have the following characteristics (d) to (f) as well as the characteristics (a) to (c).

(d) They have high UV screening power.
(e) They are light semi-conductors.
(f) They have antimicrobial activity and antifungal activity.

When the inorganic compound particles are porous, especially when they are porous and hollow, they have the following characteristics (g) and (h) in addition to (a) to (f).

(g) They have excellent adsorptivity for, for example, acidic or basic compounds, such as fatty acids, amines and sulfur oxide, which cause smell and are therefore useful as a deodorant.

(h) They have controlled release properties. For example, the inorganic compound particles having adsorbed an aromatic component can release the aromatic component at a controlled rate of release. The rate of slow release and the amount of adsorption can be controlled by adjusting the pore size or the porosity of the particles.

The particles of the invention are excellent in heat resistance and can not only be compounded into those resins which are molded at high temperatures, such as polyesters and polycarbonates, but can be applied to the surface of glass, etc. with the aid of an inorganic binder to form a coating film, which can then be heated at a high temperature. Thus, the applicability of the particles is not restricted thermally.

The process for producing the inorganic compound particles of the invention is not particularly limited.

The inorganic compound particles of the invention can be produced by the process of the present invention with good productivity.

According to the process of the invention, a mixture of zinc and a carboxyl-containing compound dissolved or dispersed in a medium comprising at least an alcohol is heated to a temperature of 100° C. or higher in the presence of lactic acid or a compound thereof to thereby precipitating inorganic compound particles containing 60 to 100% by weight of zinc oxide and having on their surface a cluster of thin plate like zinc oxide crystals having tips projecting outward.

Useful zinc sources and preferred examples thereof can be those previously described with respect to the process for producing zinc oxide fine particles as described in (1) to (9) above. Particularly preferred among them are zinc oxide and/or zinc hydroxide because of their availability at low prices and freedom of choice of the carboxyl-containing compound to be combined with. Starting with these zinc sources, it is easy to obtain particles having a controlled particle size and in which the thin crystals have controlled three axes.

The amount of the zinc source to be used is, for example, 0.1 to 95% by weight, preferably 0.5 to 50% by weight, still preferably 1 to 30% by weight, in terms of ZnO, based on the total amount of the zinc source, the carboxyl-containing compound, and the alcohol. If the zinc source is less than the above range, the productivity tends to decrease. If it is more than the above range, fine particles having satisfactory dispersibility and a narrow particle size distribution tend to be hardly obtained.

Useful carboxyl-containing compounds and preferred examples thereof can be those previously described with respect to the process for producing zinc oxide fine particles as described in (1) to (9) above. Monocarboxylic acids are particularly preferred.

Useful monocarboxylic acids and preferred examples thereof can be those previously described with respect to the process for producing the composite particles as described in (10) to (18) above.

Preferred of the monocarboxylic acids are saturated fatty acids having a boiling point of 200° C. or lower at atmospheric pressure. Preferred examples are formic acid, acetic acid, propionic acid, butyric acid, and isobutyric acid. With such compounds, it is easy to control the monocarboxylic acid content in the reaction system from mixing through heating, thus making it easy to strictly control the precipitation reaction of zinc oxide crystals. It is preferable to use the saturated fatty acid in a proportion of 60 to 100 mol %, particularly 80 to 100 mol %, in the total monocarboxylic acids. If the proportion is lower than 60 mol %, the crystalline properties of zinc oxide in the fine particles tends to be reduced.

The monocarboxylic acid to be used further includes monocarboxylic acid zinc salts, e.g., zinc acetate. When such a zinc salt is used as a zinc source, it is not always necessary to separately add the above-mentioned monocarboxylic acid.

The amount of the monocarboxylic acid to be used (or to be charged) for obtaining the mixture is in a range of, for example, from 0.5 to 50 mol, preferably 2.2 to 10 mol, per mole of Zn atoms of the zinc source used. This range is advantageous for the economy, ease of formation of fine particles, and ease of obtaining fine particles having excellent dispersibility. At a lower molar ratio to Zn, zinc oxide fine particles with satisfactory crystalline properties and fine particles having uniformity in shape and size tend to be hardly obtained. A higher molar ratio to Zn not only results in bad economy but shows tendency to a failure of obtaining fine particles having satisfactory dispersibility.

The alcohols to be used can be those previously described with respect to the process for producing zinc oxide fine particles as described in (1) to (9) above. Those having a boiling point of 120° C. or higher at atmospheric pressure are preferred of them; for fine particles of excellent crystalline properties can be obtained with ease under atmospheric pressure and in a short time. For ease of obtaining particles having excellent dispersibility, monohydric alcohols having a boiling point of 120° C. or higher and a water solubility of not less than 1% by weight at 20° C., for example, monoethers or monoesters of glycols and n-butanol, are especially preferred.

While the amount of the alcohol is not particularly limited, a preferred molar ratio of the alcohol to Zn atoms originated in the zinc source is 1 to 100, particularly 5 to 80, especially 10 to 50, so that the formation of zinc oxide fine particles may be completed in a short time period. At a lower molar ratio, zinc oxide fine particles with satisfactory crystalline properties are hardly obtained, or particles excellent in dispersibility and uniformity in particle shape and size are hardly obtained. At a higher molar ratio, an economical disadvantage may result.

The alcohol may be used as a mixed solvent with water or organic solvents other than alcohols, such as ketones, esters, aromatic hydrocarbons, and ethers. The proportion of the alcohol in the mixed solvent is usually in a range of from 5 to 100% by weight, preferably 40 to 100% by weight, still preferably 60 to 100% by weight, in terms of proportion in the total mixed solvent charged (or used) for preparation of the mixture. If the proportion of the alcohol is lower than that range, particles satisfactory in crystalline properties, uniformity in shape and size, and dispersibility tend to be hardly obtained.

Lactic acid or a compound thereof which can be used in the invention includes lactic acid; lactic acid metal salts, such as ammonium lactate, sodium lactate, lithium lactate, calcium lactate, magnesium lactate, zinc lactate, aluminum lactate, manganese lactate, iron lactate, nickel lactate, and silver lactate; and lactic ester compounds capable of generating lactic acid on hydrolysis, etc., such as methyl lactate, ethyl lactate, and n-butyl lactate. These compounds may be used either individually or as a combination of two or more thereof.

While not limiting, lactic acid or a compound thereof is preferably used at a molar ratio of 0.001 to 0.4 to zinc in the mixture. If the lactic acid to Zn molar ratio is lower than 0.001, the effect of the presence of lactic acid tends to be insufficient for obtaining thin plate like zinc oxide crystals. At a higher molar ratio, precipitation reaction of zinc oxide crystals tends to hardly take place, failing to obtain desired particles. In order to obtain particles regular in shape, the molar ratio of lactic acid (or a compound thereof) to zinc is preferably in the range of from 0.001 to 0.2. In order to obtain particles regular in size and having satisfactory dispersibility, the molar ratio of lactic acid (or a compound thereof) to zinc is preferably in the range of from 0.001 to 0.1.

It is preferable that the process of the invention preferably comprises a first mixing step of preparing a first mixture comprising a zinc source and a carboxyl-containing compound and a second mixing step in which the first mixture is added and mixed with a heated alcohol-containing solution, and that lactic acid or a compound thereof be added in at least one step selected from the first mixing step and the second mixing step.

It is particularly preferable that the process of the invention comprises the following steps (I) through (III), and lactic acid or a compound thereof is added in at least one step selected from the group consisting of steps (I), (II), and (III).
(I) A step of preparing a first mixture comprising a zinc source and a carboxyl-containing compound.
(II) A step of mixing the first mixture with an alcohol to prepare a second mixture comprising the alcohol having dissolved or dispersed therein zinc and the carboxyl-containing compound.
(III) A step of maintaining the second mixture at a temperature of 100° C. or higher thereby to precipitate inorganic compound particles containing 60 to 100% by weight of zinc oxide and having on their surface a cluster of thin plate like zinc oxide crystals with their tips projecting outward.

Step (I) is preferably a step of dissolving the zinc source in a mixed solvent of the carboxyl-containing compound and water to obtain the first mixture in a solution state.

Step (II) is preferably a step of adding the first mixture to a medium comprising at least the alcohol and kept at a temperature of 100° C. or higher to obtain the second mixture.

When the first mixture comprising the zinc source and the carboxyl-containing compound is added to the alcohol, it is preferable that the first mixture be a solution. In this case, it is desirable for the zinc source and the carboxyl-containing compound to be dissolved mutually or to be dissolved in a solvent having high compatibility to both of them. Water, alcohols, ketones, and esters are advantageous as such a solvent in that they easily dissolve the zinc source and the carboxyl-containing compound at a temperature of from room temperature up to about 100° C. and that they are also highly compatible with the above-mentioned solvent. The term "alcohols" as used above embraces all the alcohol species hereinabove described.

Addition of the first mixture may be conducted at atmospheric pressure, under pressure, or under reduced pressure. Addition at atmospheric pressure is preferred from the economical viewpoint. In this case, when a dispersion of fine particles having uniformity in particle size and shape and excellent dispersibility is desired, it is preferable to keep the alcohol at 60° C. or higher, particularly 100° C. to 300° C., during addition and mixing. If the temperature of the alcohol during addition and mixing is lower than 60° C., cases are sometimes met with, in which the viscosity of the second mixture increases suddenly during or after addition and mixing, resulting in gelation. If this happens, there arise such problems that stirring is impossible and unsuccessfully achieves uniform mixing or heat conduction in the subsequent step, i.e., heating, is insufficient, resulting in temperature distribution. It follows that fine particles uniform in crystalline properties, particle size and particle shape can hardly be obtained. This problem also concerns the concentration of zinc in the second mixture and is more liable to occur at a higher zinc concentration. The lowest suitable temperature varies according to the pressure of the system. When the mixture is prepared under reduced pressure or under pressure, the temperature of the alcohol should be selected appropriately according to the pressure. When the first mixture is added to the alcohol while keeping the alcohol at a temperature within the above range, part of the carboxyl-containing compound and/or part of the alcohol may be driven out of the system through evaporation.

Addition of the first mixture to the alcohol can be carried out by adding the whole amount of the first mixture to the alcohol all at once, or adding the first mixture dropwise to the alcohol, or spraying the first mixture onto the alcohol. In particular, continuous or intermittent dropwise addition of the first mixture on or into the alcohol is preferred for obtaining highly dispersible composite particles with high productivity.

The thus prepared first mixture is added to the alcohol kept at, e.g., 60° C. or higher, preferably 100 to 300° C., and mixed therewith to obtain the second mixture. In the preparation of the second mixture by addition of the first mixture to the alcohol, the first mixture is preferably added (by, for example, dropwise addition) while evaporating part of the volatile matter of the first mixture and/or the second mixture (e.g., the carboxyl-containing compound, the alcohol or water).

For obtaining a uniform mixture, the alcohol is preferably stirred while the first mixture is being added thereto.

Lactic acid or a compound thereof can be added in any of the above-described steps but before formation of particles containing a cluster of thin plate like zinc oxide crystals. In using a metal lactate as lactic acid or a compound thereof, it is preferably added to the first mixture and dissolved therein in step (I), either together with a zinc source separately added or as a zinc source (in the case of using zinc lactate). This manner of addition is advantageous for obtaining particles uniform in shape and size.

Addition of lactic acid or a compound thereof can be carried acid, for example, as follows. In using lactic acid (CH$_3$CH(OH)COOH) and/or a lactic ester, it can be added at any stage from step (I) through step (III) either directly or as dissolved in a solvent (e.g., an alcohol). The latter manner of addition is preferred for smooth spread of the lactic acid particularly when lactic acid or a compound thereof is added in step (III). In using a metal lactate, it can be added at any stage from step (I) through step (III), and preferably it is dissolved in the first mixture together with the zinc source or as a zinc source. For example, a zinc source powder and a metal lactate powder are added to a solution containing the carboxyl-containing compound, followed by stirring to form a uniform solution. In this preparation, stirring while heating is preferred for increasing the rate of dissolution and solubility of each powder thereby to provide a high concentration solution in a short time.

The second mixture is not limited provided that it is a mixture obtained by mixing the above-described three essential components, i.e., the zinc source, the carboxyl-containing compound, and the alcohol, and lactic acid or a compound thereof is added thereto at a stage before formation of particles containing a cluster of thin plate like zinc oxide crystals. If desired, the mixture may contain components other than the three components, such as water; organic solvents, e.g., ketones, esters, (cyclo)paraffins, ethers, and aromatic compounds; additives hereinafter described; metallic components other than zinc components, e.g., inorganic metal salts (e.g., an acetate, a nitrate or a chloride) and organometallic alkoxides (e.g., metal alkoxides). Of these components, water and organic solvents are usually used as a solvent component.

The state of the second mixture is not particularly limited and may be a solution, sol, an emulsion, a suspension, etc.

On maintaining the thus obtained second mixture at 100° C. or higher, preferably 100 to 300° C., still preferably 150 to 200° C., for a period of 0.1 to 30 hours, preferably 0.5 to 10 hours, still preferably 0.5 to 5 hours, there is obtained inorganic compound particles of the present invention with practical productivity in accordance with the kinds and ratios of the raw materials. That is, on maintaining the second mixture at a temperature within the above range for a period within the above range, the zinc dissolved or dispersed in the medium is converted to X-ray crystallographically crystalline zinc oxide. Because the medium also has dissolved or dispersed therein lactic acid, the zinc oxide crystals grow anisotropically to form thin plate like zinc oxide crystals, thereby to obtain a dispersion containing inorganic compound particles whose surface is composed of the thin plate like zinc oxide crystals that gather into a cluster with their tips facing outward. With the lactic acid to zinc molar ratio falling within the range of from 0.001 to 0.4, the thin plate like zinc oxide crystals form a cluster of thin plates having a flatness of 2 to 200 and a major axis of 5 to 1000 nm.

The existing state of the individual components in the second mixture is not particularly limited. In the reaction step wherein zinc dissolved or dispersed in the alcohol is converted to thin plate like zinc oxide crystals, there are sometimes cases in which the reaction involves formation of one or more zinc oxide precursors. The case of using zinc oxide as a zinc source may be mentioned as an example. The term "zinc oxide precursors" means ions or compounds other than zinc oxide which contain at least a zinc atom. For example, the precursors include a zinc (hydrate) ion ($Zn^{2+}$), a polynuclear zinc hydroxide ion, and (basic) carboxylic acid salts, such as (basic) zinc acetate, (basic) zinc salicylate, and (basic) zinc lactate. The precursor may be present with a part or the whole thereof forming a composite with the carboxyl-containing compound and/or the alcohol as, for example, a complex salt.

To set the heating temperature of the second mixture within the above-described range brings about the advantage that strict control on the composition of the reaction system for obtaining zinc oxide fine particles, inclusive of control on the rate of evaporation of excessive or unnecessary components and the amount of evaporated components, can be taken easily. As a result, the particle size and the like of the resulting fine particles can be controlled easily. In the case when the first mixture is added to the alcohol kept at 100° C. or higher to obtain the second mixture of 100° C. or higher, heating of the resulting second mixture can be achieved by maintaining the mixture at that temperature, or the mixture is heated or cooled to a prescribed temperature, followed by heating. In the case when the first mixture is added to the alcohol below 100° C., the resulting second mixture is heated to 100° C. or higher.

In the stage of conversion of zinc in the second mixture into fine particles, the carboxyl-containing compound in the second mixture does not change or partly or totally undergoes esterification with a part or the whole of the alcohol in the second mixture to form an ester compound.

In the step for obtaining the dispersion, the alcohol, the aforesaid ester compound produced on heating, or the solvent which may, if desired, have been added in the mixture may be removed by evaporation partially or totally.

Where the second mixture contains water, it is preferable to evaporate the water to reduce the free water content of the resulting dispersion to 5% by weight or lower, particularly 1% by weight or lower. If the water content exceeds the above level, cases are sometimes met with in which the zinc oxide crystals in the fine particles have reduced crystalline properties, resulting in a failure of fulfilling the function as zinc oxide, while such depends on the kinds of the other components present in the dispersion, such as the alcohol.

It is preferable that the amount of the carboxyl-containing compound in a finally obtained dispersion be 0.5 mol or less per mole of the total zinc atoms present in the dispersion. If it exceeds 0.5 mol, cases are sometimes met with that the zinc oxide fine particles have reduced crystalline properties, failing to fulfill the function as zinc oxide. Accordingly, where the amount of the carboxyl-containing compound present in the second mixture is such that the amount of the carboxyl-containing compound in the finally obtained dispersion will exceed 0.5 mol per mole of the total zinc atoms in the resulting dispersion, at least the excess should be removed by evaporation during the heating step. Needless to say, the carboxyl-containing compound may be evaporated during heating even if the above molar ratio is 0.5 or lower.

For the purpose of controlling the particle size, shape, and surface polarity of finally obtained particles, it is possible to conduct the heating step in the presence of a long-chain saturated fatty acid, such as those having 6 to 20 carbon atoms (e.g., caprylic acid, lauric acid, myristic acid, palmitic acid, and stearic acid) (of the carboxyl-containing compounds) and/or a specific additive. The time of addition of the additive is not particularly limited and is selected appropriately according to the purpose and the kind of the additive. That is, the additive may be added in the step of preparing the second mixture or the first mixture or the step of heat treatment. When a surface treatment is aimed, the additive is preferably added after the formation of the particles.

Examples of the above-mentioned specific additive include (1) aliphatic amines, such as octadecylamine and stearylamine, (2) various coupling agents including silane coupling agents, such as methyltrimethoxysilane, phenyltrimethoxysilane, benzyltriethoxysilane, γ-aminopropyltriethoxysilane, N-β(aminoethyl)γ-aminopropyltrimethoxysilane, γ-glycidoxypropyltrimethoxysilane, γ-methacryloxypropyltrimethoxysilane, γ-mercaptopropyltrimethoxysilane, γ-chloropropyltrimethoxysilane, and stearyltrimethoxysilane; titanate coupling agents, such as isopropyltriisostearoyl titanate, bis(dioctyl pyrophosphate)oxyacetate titanate, tetraoactylbis(ditridecyl phosphite) titanate, and isopropyltri(N-aminoethylaminoethyl) titanate; and aluminum coupling agents, such as ethylacetacetatealuminum diisopropylate; and partial hydrolysis products thereof, (3) organophosphorus compounds including phosphoric esters, such as trimethyl phosphate, triethyl phosphate, tributyl phosphate, tris(2-chloroethyl) phosphate, and (polyoxyethylene)bis[bis(2-chloroethyl)phosphate]; acid phosphoric esters, such as methyl acid phosphate, propyl acid phosphate, lauryl acid phosphate, stearyl acid phosphate, bis-2-ethylhexyl phosphate, and diisodecyl phosphate; phosphorous esters, such as trimethyl phosphite; and thiophosphoric esters, such as dimethyldithiophosphate and diisopropyl dithiophosphate, (4) organopolysiloxanes containing in the molecule thereof at least one of the above-mentioned atomic groups, such as an amino group (e.g., a primary amino group, a secondary amino group, a tertiary amino group, a quaternary ammonio group, etc.), a carboxyl group, a sulfonic acid group, a phosphoric acid group, a hydroxyl group, and an epoxy group, (5) anionic surface active agents, such as sodium lauryl sulfate, sodium dodecylbenzenesulfonate, sodium polyoxyethylene lauryl ether sulfate, a sodium dialkylsulfosuccinate, and calcium stearate, (6) nonionic surface active agents, such as polyoxyethylene lauryl ether, a polyoxyethylene alkylamine, polyethylene glycol monolaurate, and glycerol monostearate, (7) cationic surface active agents, such as lauryldimethylamine and stearyltrimethylammonium chloride, (8) amphoteric surface active agents, such as lauryl betaine and stearylamine acetate, and (9) metallic soaps, such as calcium stearate. These additives may be used either individually or as a combination of two or more thereof.

According to the process of the invention, there is obtained a dispersion containing 1 to 80% by weight of fine particles in a solvent comprising an alcohol and/or the above-described ester compound and/or an organic solvent, the fine particles having a number average particle size of 0.1 to 10 $\mu$m with a coefficient of size variation of not more than 30% and a uniform shape and the individual fine particles comprising a stacked and/or radially gathered thin plate like zinc oxide crystals with their tips facing outward.

The particle dispersion as produced by the process of the invention can be used as such. If desired, the dispersion can easily be powdered or transformed to a dispersion of the particles in a different medium by solvent substitution.

Powder of the particles can be obtained by separating the particles from the dispersion medium in a conventional manner, such as filtration, centrifugation or solvent evaporation, followed by drying or, if desired, calcination. A powdering method in which the dispersion (or a concentrated dispersion) is evaporated to remove the solvent by means of a vacuum flash evaporator suppresses secondary agglomeration of fine particles, which often occurs during drying, and is therefore preferred for obtaining zinc oxide powder having excellent dispersibility.

If necessary, the resulting powder can be calcined. Calcination is usually carried out at 100° C. to 800° C. The calcining temperature should be decided appropriately so that the geometrical structure of the particles and various physical and chemical properties attributed to the structure may not be impaired. The calcining atmosphere is arbitrarily selected according to the purpose. For example, calcination can be performed in air or an inert gas atmosphere, such as nitrogen, helium or argon.

A dispersion of the particles in a solvent different from that of the dispersion as produced by the process of the invention can be obtained by a known method comprising mixing the powder prepared by the above-described powdering method with a desired solvent such as water and dispersing the mixture with mechanical energy by means of a ball mill, a sand mill, an ultrasonic homogenizer, etc. A dispersion in a different solvent can also be prepared by mixing the dispersion as produced with a desired solvent while heating the dispersion to evaporate part or the whole of the solvent to be replaced (solvent substitution under heating). The solvent to be substituted for the initial one is not particularly limited and includes organic solvents, such as alcohols, aliphatic or aromatic carboxylic acid esters, ketones, ethers, ether esters, aliphatic or aromatic hydrocarbons, and halogenated hydrocarbons; water, mineral oil, vegetable oil, wax oil, silicone oil, and the like. A suitable solvent can be selected appropriately according to the end use.

The process for producing zinc oxide-based particles described in (27) to (36) above and zinc oxide-based particles described in (50) to (58) will now be explained.

The zinc oxide-based particles according to the invention mainly comprise a metal oxide co-precipitate which contains, as a metallic component, zinc and at least one element additive selected from the group consisting of the group IIIB metal element and the group IVB metal element, has a zinc content being 80 to 99.9% in terms of the ratio of the number of zinc atoms to the total number of the atoms of the metallic components, and exhibits zinc oxide (ZnO) crystalline properties when X-ray crystallographically observed. The crystal form of zinc oxide is not particularly limited and may have an X-ray diffraction pattern of any known structures, such as a hexagonal system (wurtzite structure), a cubic system (rock salt structure), and a face-centered-cubic structure. The zinc content of the metal oxide co-precipitate ranges form 80 to 99.9%, preferably 90 to 99.5%, in terms of the ratio of the number of zinc atoms to the total number of the atoms of the metallic components. If the zinc atomic ratio is lower than the above range, the particles hardly have controlled uniformity in shape, size, higher-order structure, and the like. If the ratio is higher than the above range, the functions as a co-precipitate, that is, infrared screening properties (inclusive of heat ray screening properties) become insufficient.

Therefore, as far as the above-described conditions are fulfilled, also included in the zinc oxide-based particles as referred to in the invention are those in which an organometallic compound, such as a coupling agent (e.g., a silane coupling agent and an aluminum coupling agent), an organosiloxane or a chelate compound, is bound to the surface of the zinc oxide crystals or forms a coating layer on the surface of the zinc oxide crystals and those containing a halogen element, an inorganic acid radical (e.g., a sulfuric acid radical and a nitric acid radical) or an organic compound residue (e.g., a fatty acid residue, an alcohol residue or an amine residue) in the inside and/or on the surface thereof. It is not favorable that an alkali metal or an alkaline earth metal (as a metallic element other than the element additive selected from the group consisting of the group IIIB metal elements and the group IVB metal elements and zinc) is present in the form of a solid solution in ZnO crystals. The amount of these other metallic elements present in the particles is preferably not more than 1/10, particularly not more than 1/100, of the total number of atoms of the element additive selected from the group consisting of the group IIIB metal elements and the group IVB metal elements. This does not apply where the particles are surface-treated with an alkali metal-containing surface active agent, etc.

The element additive which constitutes the metal oxide co-precipitate is at least one member selected from the group consisting of the group IIIB metallic elements, e.g., boron, aluminum (Al), gallium (Ga), indium (In), and thallium (Tl), and the group IVB metallic elements, e.g., silicon (Si), germanium (Ge), tin (Sn), and lead (Pb). Of these metallic elements, indium and/or aluminum is/are particularly preferred.

The zinc oxide-based particles of the invention embrace three embodiments; in the first embodiment the individual particle exists in the form of a single particle comprising the metal oxide co-precipitate; in the second embodiment a plurality of the single particles gather to form the individual particle; and in the third embodiment the single particles form a composite with a polymer. These three embodiments will further be explained below.

In the first embodiment, each zinc oxide-based particle is made up solely of a single particle of the metal oxide co-precipitate. The single particle preferably has an average particle size of 0.001 to 0.1 µm, particularly 0.001 to 0.05 µm, in its shortest dimension.

Unless otherwise specified, the term "particle size", inclusive of average particle size, a number average particle size, and the like as used with respect to the zinc oxide-based particles is intended to denote the diameter in the shortest dimension. The term "diameter in the shortest dimension" as used above means the shortest of the diameters passing the center of the particle. In other words, the "particle size" means the diameter of a spherical fine particle; the minor axis of an ellipsoidal fine particle; the shortest of the axes passing the center of a cubic particle, a rectangular parallelepiped particle or a pyramidal particle; the length of the axis which passes the center and is perpendicular to the longitudinal axis of an acicular, column, rod or cylindrical particle; or the shortest axis passing the center in the direction perpendicular to the main surface, i.e., the thickness direction, (=thickness) of a flaky or (hexagonal) tabular particle.

The longest diameter of granular or spherical particles preferably falls within the same range as the shortest diameter, and that of odd-shaped particles (e.g., thin plates and needles or acicular particles) is preferably 0.002 µm or longer and smaller than 0.5 µm. The shape of the metal oxide co-precipitate or zinc oxide-based particles is arbitrary and may be, for example, a thin plate, e.g., a flaky shape or a (hexagonal) tabular shape; an acicular shape, a column shape, a rod shape, a cylindrical shape; a granular shape, e.g., a cubic shape or a pyramidal shape; and a spherical shape.

In the second embodiment, the zinc oxide-based particles are secondary particles made by gathering of the above-mentioned single particles as a primary particle. In this embodiment, the secondary particles may constitute only an outer shell to provide hollow particles. When the particles are hollow and also when the primary particles have a size of from 0.005 to 0.1 µm, particularly 0.005 to 0.05 µm, excellent diffused transmission properties are exerted. In this case, the ratio of the shortest particle size of the single particle to the shortest particle size of the zinc oxide-based particles (i.e., an agglomerate of the single particles) is preferably not more than 1/10.

In the third embodiment, the zinc oxide-based particles are composite particles comprising the above-mentioned single particles and a polymer. The structure of the composite is arbitrary. For example, (A) a polymer covers the surface of a single particle and/or the surface of an agglomerate of a plurality of the single particles, (B) a polymer binds the single particles together, and (C) a polymer constitutes a matrix in which the single particles are dispersed without being agglomerated and/or agglomerates of a plurality of the single particles are dispersed. The composite particles having structure (B) or (C) may also be hollow particles, the outer shell of which is composed of the single particles and the polymer. When the composite particles are hollow and have a primary particle size of 0.005 to 0.1 µm, particularly 0.005 to 0.05 µm, they have excellent diffused transmission properties in the same manner as in the second embodiment. In this embodiment, the amount of the polymer, while not limiting, usually ranges from 1 to 90% by weight based on the total amount of the single particle(s) and the polymer.

The polymer to be used in the composite particles of the third embodiment can be those described with reference to the zinc oxide-polymer composite particles described in (10) to (19) above.

In the second embodiment and the structures (B) and (C) of the third embodiment, the zinc oxide-based particles preferably have a spherical or ellipsoidal shape. It is preferable for the surface of these particles to have fine surface unevenness irrespective of the contour of the particles because the surface unevenness synergistically contributes to light scatter on the surface to provide improved light scattering power. In the second and third embodiments, the average particle size of the zinc oxide-based particles is not particularly limited but usually ranges from 0.001 to 10 µm. In the structure (A) of the third embodiment, an average particle size of 0.001 to 0.1 µm is preferred for high transparency. Hollow particles preferably have an average particle size of 0.1 to 5 µm for high diffuse transmission power.

The zinc oxide-based particles of the invention are sometimes used as a dispersion in a solvent. Useful media include water, alcohols, ketones, aliphatic or aromatic carboxylic acid esters, ethers, ether esters, aliphatic or aromatic hydrocarbons, halogenated hydrocarbons, mineral oil, vegetable oil, wax oil, silicone oil, and the like. In addition to these solvents, the dispersion may contain other components, for example, organic binders or inorganic binders used as a binder for coating compositions. Useful organic binders include thermoplastic or thermosetting resins, such as (meth)acrylic resins, vinyl chloride resins, silicone resins, melamine resins, urethane resins, styrene resins, alkyd resins, phenolic resins, epoxy reins, and polyester resins; and synthetic rubbers, such as ethylene-propylene copolymer rubber, polybutadiene rubber, and acrylonitrile-butadiene rubber or natural rubber. Useful inorganic binders include silica sol, alkali silicates, silicon alkoxides, and phosphates.

The process for producing the zinc oxide-based particles is explained below.

The process for producing the zinc oxide-based particles according to the present invention comprises heating a zinc source and a carboxyl-containing compound to a temperature of 100° C. or higher in an alcohol in the presence of a compound containing at least one element additive selected from the group consisting of the group IIIB metallic elements and the group IVB metallic elements to thereby form particles. The group IIB metallic elements can be those described above, with indium and/or aluminum being preferred as described above.

The process of the invention preferably comprises a first mixing step of preparing a first mixture comprising a zinc source and a carboxyl-containing compound and a second mixing step of mixing the first mixture with a heated alcohol-containing solution, and the element additive is preferably added in at least one step selected from the first mixing step and the second mixing step.

Still preferably, the process comprises a first mixing step of preparing a first mixture comprising a zinc source and a monocarboxylic acid, a second mixing step of mixing the first mixture with an alcohol to prepare a second mixture, and a heating step of heating the second mixture at a temperature of 100° C. or higher, and a compound containing at least one element additive selected from the group consisting of the group IIIB metallic elements and the group IVB metallic elements is added to the first mixture and/or the second mixture in any of these steps. The compound containing the element additive may be added either alone or as dissolved in an alcohol. The first mixing step is preferably carried out by dissolving the zinc source in a mixed solvent of the carboxyl-containing compound and water.

The process preferably includes a step in which a mixture of the zinc source and the carboxyl-containing compound in water is added to the alcohol heated to 100° C. or higher thereby to remove at least part of the water and/or the carboxyl-containing compound by evaporation. While the zinc source and the carboxyl-containing compound are preferably used as dissolved in water, it is desirable to drive water or the carboxyl-containing compound out of the system as much as possible so as to prevent reduction of the crystalline properties of the fine particles and also to prevent secondary agglomeration thereby to secure uniformity in size and shape of the fine particles. Formation of fine particles may occur during addition of the first mixture to the heated medium but is usually induced by maintaining the reaction system after the addition at a temperature of 100° C. or higher. Meanwhile, evaporation of water and the carboxyl-containing compound is usually observed.

The zinc source to be used in the process of the invention is, for example, at least one member selected from the group consisting of zinc oxide, zinc hydroxide, and zinc acetate. The carboxyl-containing compound is preferably a saturated fatty acid having a boiling point of 200° C. or lower at atmospheric pressure.

When the zinc source and the carboxyl-containing compound are maintained at a temperature of 100° C. or higher in an alcohol in the presence of a compound containing at least one element additive selected from the group consisting of the group IIIB metallic elements and the group IVB metallic elements, the system may contain (1) a polymer, (2) a compound additive containing, in the molecule thereof, one or more than one atomic groups selected from the group consisting of a carboxyl group, an amino group, a quaternary ammonio group, an amido group, an imido bond, an alcoholic and/or phenolic hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group and having a molecular weight of smaller than 1000, (3) carbon dioxide and/or a carbonic acid source, or (4) lactic acid or a compound thereof.

Where a polymer is present in the system maintained at 100° C. or higher, zinc oxide-based composite particles comprising the above-described single particles and a polymer are obtained. Suitable polymers to be used can be those described with respect to the composite particles according to (10) to (18) above.

Where a compound having the above-described specific functional group is present in the system maintained at 100° C. or higher, it is possible to conduct surface treatment of the particles, and the particle size is controllable.

Where carbon dioxide and/or a carbonic acid source is present in the system maintained at 100° C. or higher, fine particles having excellent water dispersibility and high fineness (0.05 $\mu$m or smaller) can be obtained with ease. (Basic) zinc carbonate when used as part of a zinc source will serve in substitution for a carbonic acid source. A suitable amount of a carbonic acid source is 0.1 to 20 mol % based on zinc.

Too much carbonic acid sometimes interferes with crystallization of zinc oxide, and such being the case, the heating temperature must be increased. Carbonic acid sources include compounds producing carbonate ions or carbon acid gas on, e.g., heating, such as ammonium carbonate, ammonium hydrogencarbonate, and urea; metal carbonates, such as yttrium carbonate, cadmium carbonate, silver carbonate, samarium carbonate, zirconium carbonate, cerium carbonate, thallium carbonate, lead carbonate, and bismuth carbonate; and basic metal carbonates, such as basic zinc carbonate, basic cobalt(II) carbonate, basic copper(II) carbonate, basic lead(II) carbonate, and basic nickel(II) carbonate. These carbonic acid sources can be used either individually or as a combination of two or more thereof.

The process of maintaining the system at 100° C. or higher in the presence of lactic acid or a compound thereof is effective in obtaining secondary particles that are agglomerates of the single particles comprising the metal oxide co-precipitate as a primary particle.

Lactic acid or a compound thereof to be used can be those described with respect to the process for producing inorganic compound particles described in (43) to (49) above.

The zinc oxide-based particles according to the invention will further be illustrated in detail. here the zinc oxide-based particles of the invention are single particles of the metal oxide co-precipitate (embodiment (1)), the single particles may be dispersed uniformly or may be partly agglomerated. In this case, where the single particles have an average particle size of 0.001 to 0.05 $\mu$m, particularly 0.02 $\mu$m or smaller, they are useful as a material of transparent films that screen ultraviolet rays or heat rays. Where the single particles as primary particles are agglomerated to form an outer shell composed of the secondary particles (embodiment (2)), the secondary particles have a double layer structure. In this case, the particles exhibit high light diffusing properties as well as high light transmitting properties because, in addition to light scatter on the surface of the secondary particles (corresponding to light scatter on conventional inorganic transparent fine particles), light is also scattered on the surface of the primary particles in the secondary particles and on the interface between the outer shell and the inner shell in the secondary particles. While not limiting, the ratio of the thickness of the outer shell made of agglomerated single particles to the number average particle size of the secondary particles is preferably 0.1 to 0.4. At a lower thickness ratio, the zinc oxide-based particles tend to have reduced mechanical strength. At a higher thickness ratio, the effects expected from the double layer structure may not be fully produced.

The primary particles are not particularly limited in shape and size but must be smaller than the secondary particles. For example, when the secondary particles have a number average particle size of 0.1 to 10 $\mu$m (preferably 0.1 to 2 $\mu$m), the number average particle size of the primary particles is 0.001 to 0.1 $\mu$m, which corresponds to $\frac{1}{10}$ to $\frac{1}{10000}$ of that of the secondary particles. If the number average particle size of the primary particles is smaller than that range, the ultraviolet screening power of the zinc oxide-based particles tends to be reduced. If it exceeds the above range, light transmitting properties tend to be reduced. If the ratio of the number average particle size of the primary particles to that of the secondary particles is less than the above range, the UV screening power of the secondary particles tend to be reduced. If the ratio exceeds the above range, the secondary particles tend to have insufficient mechanical strength for practical use, or the effects of agglomeration tends to be exerted unsuccessfully.

Where the secondary particles have a number of interstices among the primary particles, and also where the secondary particles are hollow, such particles perform functions as porous fine particles or microcapsules. That is, they have functions of adsorption, separation, removal, and collection, such as oil absorptivity, hygroscopicity, harmful metal ion adsorptivity, harmful gas and bad order absorptivity; heat and sound insulating functions (e.g., heat insulating fillers or sound insulating fillers); a function of immobilizing metal ions, enzymes or bacteria (e.g., catalytic carriers and fillers for chromatography); light weight properties; and a function of slowly releasing a liquid or perfume held therein.

The zinc oxide-based particles according to embodiment (3), which are composite particles composed of single particles and a polymer, include the following structures.

(3)-1: The surface of single particles is covered with a polymer. The single particles do not form secondary particles or they gather only loosely. Those particles having an average particle size of 0.001 to 0.05 $\mu$m, particularly 0.02 $\mu$m or smaller, are excellent in transparency to the visible light and useful as a material of films screening ultraviolet rays and heat rays.

(3)-2: The single particles are agglomerated and localized to form an outer shell. In this case, the polymer can be present only in the outer shell or the inner shell or both of them. It is preferable that the polymer be present only in the outer shell and the zinc oxide-based particles have a hollow structure. Hollow zinc oxide-based particles have an improved light diffusion function. While the primary particles are not particularly limited in shape and size, they must be smaller than the composite particles. For example, when the composite particles have a number average particle size of 0.1 to 10 $\mu$m (preferably 0.1 to 2 $\mu$m), the number average particle size of the primary particles is 0.001 to 0.1 $\mu$m, which corresponds to $\frac{1}{10}$ to $\frac{1}{10000}$ of that of the composite particles. If the number average particle size of the primary particles is smaller than the above range, the ultraviolet screening power of the zinc oxide-based particles tends to be reduced. If it exceeds the above range, light transmitting properties tend to be reduced. If the ratio of the number average particle size of the primary particles to that of the composite particles is less than the above range, the UV screening power of the composite particles tend to be reduced. If the ratio exceeds the above range, the composite particles tend to have insufficient mechanical strength for practical use, or the effects of combination tends to be exerted unsuccessfully. Where the polymer exists in the outer shell, covering the primary particles (single particles) or the surface of the secondary particles, the zinc oxide-based particles have excellent dispersibility and improved adhesion to a matrix polymer when formulated into a composition.

The polymer to be used in the zinc oxide-based particles of the invention is not particularly limited and can be, for example, polymers having a weight average molecular weight of 1000 to 1,000,000, including those generally called oligomers or prepolymers. Since such polymers are easily dissolved or easily emulsified or suspended as finely as possible in the first or second mixture or in the heating system for precipitating the zinc oxide-based particles, zinc oxide-based file particles regular in size (a coefficient of particle size variation of not more than 30%) and shape can be obtained easily. The Polymer to be used in the zinc oxide-based fine particles can be, for example, at least one resin selected from the groups (a) to (n) listed above with reference to the zinc oxide-polymer composite particles described in (10) to (19) above. When these resins are used, zinc oxide-based fine particles having an average particle size of, e.g., 0.001 to 10 $\mu$m are obtained easily.

The process for producing the zinc oxide-based particles of the invention is illustrated below in greater detail.

According to the process of the invention, a mixture comprising the above-described zinc source and carboxyl-containing compound dissolved or dispersed in an alcohol is heated at a temperature of 100° C. or higher in the presence of a compound containing at least one element additive selected from the group consisting of the group IIIB metallic elements and the group IVB metallic elements (hereinafter sometimes referred to as a metal (M)) to precipitate zinc oxide-based particles comprising a crystalline co-precipitate of metal oxides containing 80 to 99.9% of zinc and 0.1 to 20% of the metal (M) in terms of the ratio of the number of atoms to the total number of metallic atoms. The language "compound containing at least one element additive (M)" as used herein is intended to mean a concept inclusive of a simple metallic body and an alloy. The language will be sometimes referred to as a metal (M) compound.

The zinc source is converted to zinc oxide which is X-ray crystallographically crystalline upon being heated in a mixture of the carboxyl-containing compound and the alcohol. The existence of the metal (M) compound in this system provides a dispersion containing the zinc oxide-based particles of the invention. If any one of the three components, i.e., a zinc source, a carboxyl-containing compound, and an alcohol, is missing, precipitation of zinc oxide crystals does not take place. If the metal (M) is absent, the zinc oxide-based particles of the invention are not obtained.

Useful zinc sources and the amount to be used and preferred examples thereof can be those previously described with respect to the process for producing the composite particles as described in (10) to (18) above.

Useful carboxyl-containing compounds and the amount to be used can be those previously described with respect to the process for producing zinc oxide fine particles described in (1) to (9) above. Monocarboxylic acids described with respect to the process for producing the composite particles described in (10) to (18) are particularly preferred.

Useful alcohols and the amount to be used and preferred examples thereof can be those previously described with respect to the process for producing the composite particles as described in (10) to (18) above. In particular, those having a boiling point of 120° C. or higher at atmospheric pressure are preferred of them for ease of obtaining particles of excellent crystalline properties under atmospheric pressure and in a short time. For ease of obtaining particles having excellent dispersibility, monohydric alcohols having a boiling point of 120° C. or higher and a water solubility of not less than 1% by weight at 20° C., for example, monoethers or monoesters of glycols and n-butanol, are especially preferred.

The metal (M) compound which can be used in the process of the invention is at least one compound (inclusive of a metal, such as a simple metal and an alloy) selected from, for example, metals (simple metal (M) or alloys of metal (M)); oxides; hydroxides; inorganic salts, such as (basic) carbonates, nitrates, sulfates, and halides (e.g., chlorides or fluorides); carboxylic acid salts, such as acetates, propionates, butyrates, and laurates; metal alkoxides; all the compounds containing a trivalent or tetravalent metal (M), such as metal chelate compounds formed with a β-diketone, a hydroxycarboxylic acid, a keto ester, a keto alcohol, an amino-alcohol, a glycol, a quinoline, etc.; and compounds containing a metal exhibiting a few valences, e.g., In or Tl, in the lower valent state, the metal being capable of finally changing to the trivalent or tetravalent state in the course of fine particle formation.

In using aluminum as the group IIIB metallic element, examples of compounds containing aluminum are aluminum, aluminum hydroxide, aluminum oxide, aluminum chloride, aluminum fluoride, aluminum nitrate, aluminum sulfate, basic aluminum acetate, trisacetylacetonatoaluminum, aluminum trimethoxide, aluminum triethoxide, aluminum triisopropoxide, aluminum tri-n-butoxide, an acetoalkoxyaluminum diisopropylate, aluminum laurate, aluminum stearate, diisopropoxyaluminum stearate, and ethylacetoacetatoaluminum diisopropylate.

In using boron as the group IIIB metallic element, examples of compounds containing boron are boron trioxide, boric acid, boron bromide, boron trifluoride diethyl ether complex, boron trifluoride monoethylamine complex, trimethyl borate, triethyl borate, triethoxyborane, and tri-n-butyl borate.

In using gallium as the group IIIB metallic element, examples of compounds containing gallium are gallium, gallium hydroxide, gallium oxide, gallium(III) chloride, gallium(III) bromide, gallium(III) nitrate, gallium(III) sulfate, ammonium gallium sulfate, gallium triethoxide, and gallium tri-n-butoxide.

In using indium as the group IIIB metallic element, examples of compounds containing indium are indium, indium(III) oxide, indium(III) hydroxide, indium(III) sulfate, indium(III) chloride, indium(III) fluoride, indium (III) iodide, indium isopropoxide, indium(III) acetate, indium triethoxide, and indium tri-n-butoxide.

In using thallium as the group IIIB metallic element, examples of compounds containing thallium are thallium, thallium(I) oxide, thallium(III) oxide, basic thallium(I) hydroxide, thallium(I) chloride, thallium(I) iodide, thallium (I) nitrate, thallium(I) sulfate, thallium(I) hydrogensulfate, basic thallium(I) sulfate, thallium(I) acetate, thallium(I) formate, thallium(I) malonate, thallium(III) chloride, thallium(III) nitrate, thallium(III) carbonate, thallium(III) sulfate, and thallium(III) hydrogensulfate.

In using silicon as the group IVB metallic element, examples of compounds containing silicon include silicon; silicon oxide; silicon alkoxide compounds, such as tetraalkoxysilanes (e.g., tetramethoxysilane, tetraethoxysilane, and tetrabutoxysilane), alkylalkoxysilanes (e.g., methyltrimethoxysilane, trimethoxysilane, 3-chloropropyltrimethoxysilane, 3-mercaptopropyltrimethoxysilane, III-glycidoxypropyltrimethoxysilane, III-(II-aminoethylaminopropyl)trimethoxysilane, diethoxydimethylsilane, trimethylethoxysilane, and hydroxyethyltriethoxysilane), and other silane coupling agents (e.g., phenyltrimethoxysilane, benzyltriethoxysilane, γ-aminopropyltriethoxysilane, N-β(aminoethyl)γ-aminopropyltrimethoxysilane, γ-glycidoxypropyltrimethoxysilane, γ-methacryloxypropyltrimethoxysilane, γ-mercaptopropyltrimethoxysilane, γ-chloropropyltrimethoxysilane, and stearyltrimethoxysilane; chlorosilanes, such as silicon tetrachloride, trichlorosilane, and methyltrichlorosilane; and acetoxysilanes, such as triacetoxysilane.

In using germanium as the group IVB metallic element, examples of compounds containing germanium are germanium, germanium(IV) oxide, germanium(IV) chloride, germanium(IV) iodide, germanium(IV) acetate, germanium(IV) chloride bipyridyl complex, β-carboxyethylgermanium sesquioxide, and germanium(IV) ethoxide.

In using tin as the group IVB metallic element, examples of compounds containing tin are tin, tin(IV) oxide, tin(IV) chloride, tin(IV) acetate, di-n-butyltin(IV) dichloride, di-n-butyltin(IV) dilaurate, di-n-butyltin(IV) maleate (polymer), di-n-butyltin(IV) oxide, di-n-methyltin(IV) dichloride, di-n-octyltin(IV) maleate (polymer), di-n-octyltin(IV) oxide, diphenyltin(IV) dichloride, mono-n-butyltin(IV) oxide, tetra-n-butyltin(IV), tin(II) oxalate, tri-n-butyltin(IV) acetate, tributyltin ethoxide, trimethyltin chloride, triphenyltin acetate, triphenyltin(IV) hydroxide, tin tetraethoxide, and tin tetra-n-butoxide.

In using lead as the group IVB metallic element, examples of compounds containing lead are lead, lead(IV) acetate, lead(IV) chloride, lead(IV) fluoride, lead(IV) oxide, lead(II+IV) oxide, and lead(II) oxalate.

The oxide or hydroxide of metal (M) can be used either as powdered or in the form of an aqueous or alcoholic sol of a metal oxide and/or hydroxide of colloidal level, such as alumina sol or silica sol.

The process of the invention comprises, for example, the following steps (I) to (III), and the metal (M) compound is added in one or more than one of steps (I), (II), and (III).

(I) A first step of preparing a first mixture comprising a zinc source and a carboxyl-containing compound.

(II) A second step of mixing the first mixture with an alcohol to prepare a second mixture comprising the alcohol having dissolved or dispersed therein zinc and the carboxyl-containing compound.

(III) A third step of heating the second mixture at a temperature of 100° C. or higher thereby to precipitate zinc oxide-based particles comprising a crystalline co-precipitate of metal oxides containing 80 to 99.9% of zinc and 0.1 to 20% of metal (M) in terms of the ratio of the number of atoms to the total number of atoms of metallic elements.

Step (I) is preferably a step of preparing a first mixture which further contains water. In this case, a first mixture in a solution state can easily be obtained. The order of addition of the zinc source, the carboxyl-containing compound, and water is arbitrary. For example, the zinc source can be dissolved in a mixed solvent of the carboxyl-containing compound and water to prepare the first mixture.

It is preferable to carry out steps (II) and (III) by an embodiment in which the first mixture is added to and mixed with the alcohol maintained at a temperature of 100° C. or higher to obtain the second mixture with ease.

When the first mixture comprising the zinc source and the carboxyl-containing compound, which may further comprises the metal (M) compound, is added to the alcohol, it is preferable that the first mixture be a solution. In this case, it is desirable for the zinc source and the carboxyl-containing compound to be dissolved mutually or to be dissolved in a solvent having high compatibility to both of them. Water, alcohols, ketones, and esters are advantageous as such a solvent in that they easily dissolve the zinc source and the carboxyl-containing compound and, if any, the metal(M) compound at a temperature of from room temperature up to about 100° C. and that they are also highly compatible with the above-mentioned medium. The term "alcohols" as used above embraces all the alcohol species hereinabove described.

In the stage where the zinc source is converted to X-ray crystallographically crystalline zinc oxide, there are cases in which the reaction sometimes involves formation of one or more zinc oxide precursors (which may or may not contain metal (M)). The case of using zinc oxide as a zinc source may be mentioned as an example. The term "zinc oxide precursor" means ions or compounds other than zinc oxide which contain at least a zinc atom. For example, the precursors include a zinc (hydrate) ion ($Zn^{2+}$), a polynuclear hydroxide ion of zinc, the above ions partly or totally chelated by a chelating compound, e.g., a β-dicarbonyl compound (e.g., acetylacetone), lactic acid, ethylene glycol or ethanolamine, and (basic) carboxylic acid salts, such as (basic) zinc acetate, (basic) zinc salicylate, and (basic) zinc lactate. The precursor may be present with a part or the whole thereof forming a composite with the carboxyl-containing compound and/or the alcohol as, for example, a complex salt.

In the stage where the zinc source and the metal (M) compound used as a raw material are converted to zinc oxide-based fine particles in the second mixture, the carboxyl-containing compound in the second mixture does not change or partly or totally undergoes esterification with a part or the whole of the alcohol in the second mixture to form an ester compound.

The second mixture is not limited provided that it is a mixture obtained by mixing the above-described four essential components, i.e., the zinc source, the carboxyl-containing compound, the alcohol, and the metal (M) compound. If desired, the mixture may contain components other than the four components, such as water; organic solvents, e.g., ketones, esters, (cyclo)paraffins, ethers, and aromatic compounds; additives hereinafter described; metallic components other than zinc and metal (M), e.g., acetates, inorganic metal salts (e.g., a nitrate or a chloride) and organometallic alkoxides (e.g., metal alkoxides). However, because an alkali metal or alkaline earth metal sometimes causes reduction in heat ray cutting function and electrical conductivity of the fine particles, its content in the mixture is preferably not more than $1/10$, particularly not more than $1/100$, in terms of the ratio to the total number of atoms of metal (M) in the mixture. Of these components, water and organic solvents are usually used as a solvent component.

The mutual state of the four components and the state of each component in the second mixture are not particularly limited. Taking the zinc source, for instance, the zinc source and/or the metal (M) compound can be dissolved as such in a solvent component, such as the alcohol and/or water or an organic solvent; or the zinc source is changed to the above-described zinc oxide precursor and dissolved or dispersed in a colloidal, emulsified or suspended state in the solvent component.

Accordingly, the state of the second mixture is not particularly limited. Whether the mixture is liquid, sol, an emulsion or a suspension will not cause be a problem.

The second mixture is prepared by mixing the components within the above-described ranges. The preparation method is not particularly limited.

In order to obtain a dispersion of zinc oxide-based particles while controlling the average particle size of the single particles within a range of from 0.001 to 10 μm, it is preferred for practical productivity to add the first mixture comprising a zinc source and a carboxyl-containing compound to a heated alcohol-containing solution to prepare the second mixture.

The method of preparing the mixture according to the above-described preferred mode is further illustrated below.

Addition of the first mixture can be carried out by adding the whole amount of the first mixture all at once, or adding the first mixture dropwise on or into the alcohol-containing solution, or spraying the first mixture.

Addition of the first mixture may be conducted at atmospheric pressure, under pressure, or under reduced pressure. Addition at atmospheric pressure is preferred from the economical consideration. In this case, when a zinc oxide-based fine particle dispersion having uniformity in particle size and shape, etc. and a controlled state of dispersion or agglomeration is desired, it is preferable to keep the alcohol-containing solution at 60° C. or higher, particularly 60° C. to 300° C., during addition and mixing. If the temperature of the alcohol-containing solution during addition and mixing is lower than 60° C., the viscosity of the second mixture tends to increase suddenly during or after addition and mixing, resulting in gelation. If this happens, there arise such problems that stirring is impossible and unsuccessfully achieves uniform mixing or heat conduction in the subsequent step, i.e., heating, is insufficient, resulting in temperature distribution. It follows that zinc oxide fine particles uniform in crystalline properties, particle size and particle shape can hardly be obtained but agglomerated particles. This problem also concerns the concentration of zinc in the second mixture and is more liable to occur at a higher zinc concentration. The lowest suitable temperature varies according to the pressure of the system. When the mixture is prepared under reduced pressure or under pressure, the temperature of the alcoholic solvent should be selected appropriately. When the first mixture is added to the alcohol-containing solution under heating as described above, part of the carboxyl-containing compound and/or part of the alcohol of the second mixture are sometimes driven out of the system through evaporation. The mixture thus prepared is also included in the second mixture.

While the raw material composition for preparing the first mixture is not particularly limited, it is preferable that the amount of the zinc source to be used as a raw material of the first mixture ranges from 1 to 90% by weight, in terms of ZnO, based on the total amount of the first mixture and that the amount of the carboxyl-containing compound to be used as a raw material of the first mixture ranges from 0.5 to 50 mol per mole of Zn atoms of the zinc source.

The thus prepared first mixture is added and mixed with the alcohol-containing solution to obtain the second mixture.

The first mixture when added may be at room temperature or as heated. For obtaining a uniform mixture, the alcohol-containing solution is preferably stirred while the first mixture is being added thereto.

While not limiting, the amount of the alcohol in the alcohol-containing solution preferably ranges from 1 to 100 mol per mole of the Zn atoms originated in the zinc source present in the second mixture so that the formation of zinc oxide-based fine particles under heating may be completed in a short time period. The alcohol concentration in the alcohol-containing solution is usually in a range of from 5 to 100% by weight based on the total weight of the solution.

Heating of the thus prepared second mixture results in production of a dispersion containing zinc oxide-based particles in good yield.

The heating temperature is not particularly limited. The heating must be, as a matter of course, at or above the temperature at which crystalline zinc oxide precipitates, but the temperature cannot be decided definitely because it is subject to variation in accordance with desired morphology of zinc oxide-based fine particles, such as the size, shape and state of dispersion or agglomeration. The heating temperature and heating time should be selected from a comprehensive point of view including the initial composition of the second mixture and the above-mentioned various parameters. In particular, when it is desired to obtain a dispersion of zinc oxide-based fine particles having the average single particle size controlled within a range of from 0.001 to 10 μm with practical productivity, it is preferable to heat the second mixture at 100° C. or higher, still preferably 100 to 300° C., particularly preferably 120° C. or higher.

In the case when the first mixture is added to an alcohol-containing solution kept at 100° C. or higher to obtain the second mixture, heating of the resulting second mixture can be achieved by maintaining the mixture at that temperature, or the mixture is heated or cooled to a prescribed temperature, followed by heat treatment. In the case when the first mixture is added to an alcohol-containing solution below 100° C. to obtain the second mixture, the resulting second mixture is heated to 100° C. or higher, followed by heat treatment. To set the second mixture heating temperature at 100° C. or higher brings about the advantage that strict control on the composition of the reaction system, inclusive of control on the rate of evaporation of excessive or unnecessary components and the amount of the evaporated components, can be taken easily for obtaining zinc oxide-based fine particles. As a result, the particle size and the like of the resulting particles can be controlled easily.

In the heating step for obtaining the dispersion, the components other than the above-described ones, i.e., the alcohol, the aforesaid ester compound produced upon heating, or the solvent component which may, if desired, have been used in the mixture may be removed by evaporation partially or completely.

While not limiting, a preferred heating time for completion of the reaction is usually about 0.1 to 30 hours.

Where water is present in the second mixture, it is preferable for conversion to zinc oxide-based fine particles to evaporate the water to reduce the free water content of the dispersion to 5% by weight or lower, particularly 1% by weight or lower, during the heating step. If the water content exceeds the above level, cases are sometimes met with that the zinc oxide-based fine particles have reduced crystalline properties, resulting in a failure of fulfilling the function of zinc oxide, while such depends on the kinds of the other components present in the dispersion, such as the alcohol.

It is preferable that the amount of the carboxyl-containing compound in a finally obtained zinc oxide-based particle dispersion be 0.5 mol or less per mole of the total zinc atoms present in the dispersion. If it exceeds 0.5 mol, there are sometimes cases in which the zinc oxide-based fine particles have reduced crystalline properties, failing to fulfill the function of zinc oxide. Accordingly, where the amount of the carboxyl-containing compound present in the second mixture is such that the amount of the carboxyl-containing compound in the finally obtained dispersion will exceed 0.5 mol per mole of the total zinc atoms in the resulting dispersion, at least the excess should be removed by evaporation during the heating step. Needless to say, the carboxyl-containing compound may be evaporated during heating even if the above molar ratio is 0.5 or lower.

The process of maintaining the system at 100° C. or higher in the presence of lactic acid or a compound thereof is effective in obtaining secondary particles that are agglomerates of the above-identified single particles as primary particles. Lactic acid or a compound thereof to be used includes lactic acid; lactic acid metal salts, such as ammonium lactate, sodium lactate, lithium lactate, calcium lactate, magnesium lactate, zinc lactate, aluminum lactate, manganese lactate, iron lactate, nickel lactate, and silver lactate; and lactic ester compounds capable of generating lactic acid on hydrolysis, etc., such as methyl lactate, ethyl lactate, and n-butyl lactate. These compounds may be used either individually or as a combination of two or more thereof.

While not limiting, the amount of lactic acid or a compound thereof is usually 0.001 to 0.4 in terms of molar ratio to zinc in the second mixture. At a lower molar ratio, the effect of the presence of lactic acid tends to be insufficient for obtaining zinc oxide crystals. At a higher molar ratio, precipitation reaction of zinc oxide crystals tends to hardly take place, failing to obtain desired fine particles. In order to obtain fine particles regular in shape, the molar ratio of lactic acid to zinc is preferably in the range of from 0.001 to 0.2. In order to obtain fine particles regular in size and having satisfactory dispersibility, the molar ratio of lactic acid to zinc is preferably in the range of from 0.001 to 0.1.

Addition of lactic acid or a compound thereof can be carried out, for example, as follows. In using lactic acid ($CH_3CH(OH)COOH$) and/or a lactic ester, it can be added at any stage from step (I) through step (III) either directly or as dissolved in a solvent (e.g., an alcohol). The latter manner of addition is preferred for smooth spread of the lactic acid particularly when a lactic acid source is added in step (III). In using a metal lactate, it can be added at any stage from step (I) through step (III), and preferably it is dissolved in the first mixture together with the zinc source or in the form of a zinc source in step (I). For example, a zinc source powder and a metal lactate powder are mixed with a solution containing a monocarboxylic acid and stirred to form a uniform solution. In this preparation, stirring while heating is preferred for increasing the rate of dissolution and solubility of each powder thereby to provide a high concentration solution in a short time.

Where lactic acid is dissolved or dispersed in the medium, cases sometimes occur in which zinc oxide crystals grow anisotropically into thin plate like zinc oxide crystals to provide a dispersion containing zinc oxide-based fine particles whose surface comprises a cluster of such thin plate like zinc oxide crystals with their tips projecting outward. In such cases and when the lactic acid to zinc molar ratio falls within a range of from 0.001 to 0.4, there are formed favorable single particles having a thin plate shape (anisotropic shape) which have, for example, an L/B ratio (major axis/minor axis) of 1.0 to 5.0, a flatness (major axis/thickness) of 2 to 200, and a major axis of 5 to 1000 nm, and exhibit excellent diffused transmission properties. The major axis is the longest of measured three axes of the particle, and the thickness is the smaller of the width and the height out of the three axes.

The polymer which can be used in the process of the invention are the same as those explained with regard to the zinc oxide-based particles of the invention.

While not limiting, the polymer is used at a weight ratio of, for example, 0.01 to 2.0, to the zinc atoms, as converted to zinc oxide, in the zinc source (of the second mixture). If the amount of the polymer is lower than that ratio, composite particles tend to be hardly obtained. If the amount of the polymer is higher than that ratio, the precipitation of zinc oxide crystals tends to hardly occur. In order to obtain zinc oxide-based particles having the above-mentioned double layer structure, uniformity in particle shape and size, and satisfactory dispersibility, the polymer is preferably used at a weight ratio of 0.05 to 0.5 to the zinc oxide content, while somewhat varying according to the kind of the polymer and other reaction conditions.

According to the process of the invention, the polymer is added to any one or more than one steps of the above-described steps. Addition of the polymer is conducted at an arbitrary stage before precipitation of zinc oxide-based particles. For example, the polymer can be added to the first mixture or the second mixture.

According to the process of the invention, the polymer can be added in any of the above-described steps but before formation of zinc oxide-based particles.

For smooth spread of the polymer throughout the reaction system, it is preferable for the polymer to be previously dissolved in the same alcohol as used as a medium or an arbitrary solvent. The solvent for dissolving the polymer is not particularly limited as far as it is capable of dissolving the polymer, and is usually at least one member selected from organic solvents, such as alcohols (the above-described ones), aliphatic or aromatic carboxylic acids, aliphatic or aromatic carboxylic acid esters, ketones, ethers, ether esters, aliphatic or aromatic hydrocarbons, and halogenated hydrocarbons; water; mineral oil; vegetable oil; wax oil; and silicone oil.

The second mixture is not limited provided that it is a mixture obtained by mixing the above-described four essential components, i.e., a zinc source, a carboxyl-containing compound, an alcohol, and metal (M). In order to obtain hollow particles the outer shell of which is formed of co-precipitated single particles or particles comprising a polymer having dispersed therein a number of single particles, the polymer is added in a stage before formation of zinc oxide-based particles.

On maintaining the second mixture containing the polymer at 100° C. or higher, preferably 100 to 300° C., still preferably 150 to 200° C., for a period of 0.1 to 30 hours, preferably 0.5 to 10 hours, there are obtained the zinc oxide-based particles of the invention as zinc oxide-based crystals-polymer composite particles with practical productivity in accordance with the kinds and ratios of the raw materials. That is, on maintaining the second mixture at a temperature within the above range for a period within the above range, the zinc dissolved or dispersed in the medium is converted to X-ray crystallographically crystalline zinc oxide. Because the medium also has dissolved or dispersed therein the polymer, the polymer forms a composite while the nuclei of zinc oxide crystals precipitate and grow, thereby providing a dispersion containing zinc oxide-polymer composite particles. The internal structure, shape and size of the composite particles formed, and the particle size of the single particles (co-precipitated metal oxide) present therein can be controlled by selection of the kinds and ratios of the raw materials (e.g., the polymer and the alcohol), the composition and temperature of the reaction system at the time when composite particles are formed that are based on the thermal history, etc. applied till composite particles are formed.

According to the process of the invention, there is obtained a dispersion containing 1 to 80% by weight of zinc oxide-based particles in an alcohol and/or the above-described ester compound and/or an organic solvent, in which the zinc oxide-based particles contain a metal oxide co-precipitate and a polymer and have a number average particle size of 0.001 to 10 μm and a coefficient of size variation of not more than 30%.

It is also possible to add a specific additive to the system in the step of heating for the purpose of controlling the size, shape, state of dispersion or higher-order and/or the polarity or composition of the surface of the finally obtained zinc oxide-based single particles. The stage of addition of the additive is not particularly restricted. The additive can be added in either of the step of preparing the second mixture or the first mixture or the step of heating. The stage of addition is selected appropriately according to the purpose and the kind of the additive. In many cases, the effects of the additive are fully exerted when added immediately before or after precipitation of zinc oxide crystals.

In particular, in order to obtain zinc oxide-based particles having high uniformity in size and shape of the single particles, it is preferable that a compound containing in the molecule thereof a carboxyl group, an amino group, a quaternary ammonio group, an amido group, an imido bond, a hydroxyl group, an ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group and having a molecular weight of less than 1,000 be present as an additive in the system in the heating step.

Useful additives and their amount can be those described with reference to the process for producing the zinc oxide fine particles described in (1) to (9) above.

A preferred embodiment of the invention for obtaining zinc oxide-based particles having an average single particle size controlled within a range of from 0.001 to 0.1 μm can be achieved when any one of the following conditions (I) to (IV), preferably 2 or 3 of the conditions, still preferably all of them are satisfied.

(I) Of the above-described zinc sources, a zinc source mainly comprising at least one compound selected form the group consisting of zinc oxide, zinc hydroxide, and zinc acetate, particularly a zinc source mainly comprising zinc oxide and/or zinc hydroxide is used.

Zinc oxide, zinc hydroxide, and zinc acetate contain substantially no impurity that might interfere with the reaction forming zinc oxide-based fine particles in the heating step, therefore making it easy to strictly control the particle size to such fineness of 0.001 to 0.1 μm. Above all, zinc oxide and zinc hydroxide are available at a low price, allow a free choice of the carboxyl-containing compound to be combined with, and make it particularly easy to obtain fine particles within the above particle size range.

(II) The carboxyl-containing compound is a saturated fatty acid having a boiling point of 200° C. or lower at atmospheric pressure.

Specifically, formic acid, acetic acid, propionic acid, butyric acid, and isobutyric acid are preferred. Acetic acid is particularly preferred. With these compounds, it is easy to control the carboxyl group content in the reaction system from mixing through heating, thus making it easy to strictly control the particle size to such fineness. It is still preferable to use the above saturated fatty acid in a proportion of 80 mol % or higher in the total carboxyl-containing compounds.

While the content of the carboxyl-containing compound falling within the above-described preferred range is not limited further, a particularly preferred content of the carboxyl-containing compound in the first mixture ranges from 2.2 to 10 mol per mole of Zn atoms of the zinc oxide for obtaining fine particles which have excellent dispersibility and prevented from secondary agglomeration.

(III) The second mixture is prepared by adding the first mixture, obtained by mixing a zinc source, a carboxyl-containing compound, and a metal (M) compound, to an alcohol-containing solution kept at 100° C. or above, particularly 1000 to 300° C., by continuous or intermittent dropwise addition.

The first mixture is preferably in a liquid state. It is still preferable that the zinc source, the carboxyl-containing compound, and the metal (M) compound are mutually dissolved or they are dissolved in a solvent having high compatibility with them. Water, alcohols, ketones, and esters are advantageous as such a solvent in that they easily dissolve the zinc source and the carboxyl-containing compound under heating at room temperature up to about 100° C. and that they are also highly compatible with the alcoholic solvent. The term "alcohols" as used above embraces all the alcohol species described above.

(IV) The heating of the second mixture is conducted at 1000 to 300° C., particularly 1500 to 300° C.

At the time when ZnO crystals precipitate to form the particles of the invention on heating the second mixture, the Zn concentration in terms of ZnO in the second mixture is preferably 0.5 to 20 wt %, still preferably 2.0 wt % or higher and lower than 10 wt %, for obtaining particles which have an average primary particle size of 0.001 to 0.1 μm and are prevented from secondary agglomeration.

The zinc oxide-based particles having an average particle size ranging from 0.001 to 0.1 μm can be made those with further controlled uniformity in size and shape, controlled surface conditions, such as hydrophilic/lipophilic properties, or a controlled state of dispersion or agglomeration. Effective methods for controlling these attributes are set forth below. In the preferred process for producing zinc oxide-based particles having an average particle size of 0.001 to 0.1 μm, addition of the above-described additive in the same manner as described above is also effective in obtaining zinc oxide-based particles with a controlled shape, a controlled state of dispersion or higher-order structure, and controlled surface polarity. When it is desired to produce zinc oxide-based particles which have a regular primary particle size distribution with the average particle size substantially falling within the above range, and are inhibited from secondary agglomeration, it is preferable to use a zinc source comprising, as a main component, at least one compound selected from the group consisting of zinc oxide, zinc hydroxide, and zinc acetate and, as a secondary component, basic zinc carbonate and/or a zinc salt of a carboxyl-containing compound having a boiling point higher than the heating temperature at atmospheric pressure. The ratio of the secondary component to the main component is 0.01 to 20% in terms of atomic ratio of zinc. If the ratio is less than 0.01%, the effect of the combined use of the secondary component is insufficient. If it exceeds 20%, the system sometimes fails to produce zinc oxide having high crystalline properties.

As an alternative process for obtaining zinc oxide-based particles regular in shape and size and excellent in dispersibility, it is effective to perform the heat treatment in the presence of carbonate ions and/or $CO_2$. This can be achieved by, for example, supplying carbon dioxide gas intermittently or continuously or adding a compound capable of generating carbon dioxide or carbonate ions under heating, such as urea, ammonium (hydrogen) carbonate, and basic zinc carbonate, to the heating system before and/or during the zinc oxide forming reaction.

When the above-described conditions are satisfied in the process of the invention, there is obtained a dispersion containing zinc oxide-based particles in a zinc oxide concentration of 1 to 80% by weight in an alcohol and/or the above-described ester compound and/or an organic solvent, in which the particles have an average particle size of 0.001 to 0.1 μm, a controlled shape, a controlled surface condition, and a controlled state of dispersion or agglomeration.

The dispersion of the zinc oxide-based particles obtained in the invention can be used as such. If desired, the dispersion can easily be powdered or transformed to a coating composition containing the zinc oxide-based particles or a dispersion of the zinc oxide-based particles in a different medium (by solvent substitution).

Powdering or solvent substitution can be carried out in the same manner as described with reference to the process for producing the composite particles as described in (10) to Use of the zinc oxide fine particles obtained by the process described in (1) to (9), the zinc oxide-polymer composite particles obtained by the process described in (10) to (18), the inorganic compound particles obtained by the process described in (19) to (26), the zinc oxide-based particles obtained by the process described in (27) to (36), the zinc oxide-polymer composite particles described in (37) to (42), the inorganic compound particles described in (43) to (49), and the zinc oxide-based particles described in (50) to (58) (hereinafter inclusively referred to as "zinc oxide-based fine particles") will be described below.

The zinc oxide-based fine particles according to the invention can be used in the form of a composition containing at least one of them in various industries. For the purpose of adding value to films, sheets, fiber, plastic plates, glass, paper, cosmetics, and so on, at least one kind of the zinc oxide-based fine particles of the invention is added to resin compositions providing films, sheets, fiber, plastic plates, paper, cosmetics, etc.; coating compositions to be applied to films, sheets, fiber, plastic plates, etc.; paper; cosmetics; and the like.

[1] Coating Composition and Coated Articles of the Invention

The coating composition of the invention contains at least one kind of particles selected from the zinc oxide-based fine particles of the invention and a binder component capable of forming a coating film binding the zinc oxide-based fine particles. The zinc oxide-based fine particles and the binder component are used in an amount of 0.1 to 99% by weight and 1 to 99.9% by weight, respectively, based on the total solids content of them.

The coated article according to the invention comprises at least one substrate selected from the group consisting of a resin molded article, glass, and paper and a coating film provided on either one or both sides of the surface of the substrate. The coating film comprises at least one kind of the zinc oxide-based fine particles of the invention and a binder component binding the zinc oxide-based fine particles. The amount of zinc oxide-based fine particles and the binder component is 0.1 to 99% by weight and 1 to 99.9% by weight, respectively, based on their total solids content. The resin molded article as a substrate has at least one form selected from the group consisting of a plate, a sheet, a film, and fiber. The substrate may be either transparent or semi-transparent.

If the amount of the fine particles exceeds the above range, the coating film has insufficient adhesion to the substrate, poor scratch resistance or abrasion resistance. If it is lower than that range, the effects of adding the fine particles are insufficient.

The total weight of the zinc oxide-based fine particles and the binder component is, for example, 1 to 80% based on the weight of the coating composition, being selected appropriately according to the purpose of use, workability, and the like. The balance of the coating composition comprises a solvent for dispersing the fine particles and for dissolving or dispersing the binder component and additives used according to the use of the composition, such as pigments.

The binder component useful in the coating composition is not particularly limited and includes (1) organic binders, such as thermoplastic or thermosetting synthetic resins, e.g., (meth)acrylic resins, vinyl chloride resins, silicone resins, melamine resins, urethane resins, styrene resins, alkyd resins, phenolic resins, epoxy reins, and polyester resins, and synthetic or natural rubbers, e.g., ethylene-propylene copolymer rubber, polybutadiene rubber, styrene-butadiene rubber, and acrylonitrile-butadiene rubber; and (2) inorganic binders, such as silica sol, alkali silicates, silicon alkoxides, and phosphates. These binder components are used either individually or as a combination of two or more thereof, being selected appropriately according to the requirements of the coating film formed by applying the coating composition onto a substrate and drying, such as heat resistance and scratch resistance, or the kind of the substrate.

The binder component may be used as dissolved, emulsified or suspended in a solvent.

The solvent for the binder component is selected appropriately according to the use of the coating composition and the kind of the binder. Examples of useful solvents include organic solvents, such as alcohols, aliphatic or aromatic carboxylic acid esters, ketones, ethers, ether esters, aliphatic or aromatic hydrocarbons, and halogenated hydrocarbons; water; mineral oil, vegetable oil, wax oil and silicone oil. Suitable solvents are selected according to the use. If desired, two or more of these solvents may be used as a mixture at an arbitrary ratio. The solvent for the binder component can be the solvent of the dispersion of the particles according to the invention.

The method of preparing the coating composition is not particularly limited. For example, the powder of the fine particles is dispersed in a solvent containing the binder component; a dispersion of the fine particles in a solvent and a solvent containing the binder component are mixed; or the binder component is added to a dispersion of the fine particles in a solvent. The dispersing method is not limited, and known techniques using, for example, a stirrer, a ball mill, a sand mill or an ultrasonic homogenizer can be applied.

The coating composition of the invention can also be obtained by adding the binder component or a solvent containing the binder component directly to the dispersion of zinc oxide-based particles as produced by the above-described processes.

The coating composition obtained by the above-described methods contains at least the fine particles, the binder component, and the solvent.

The resulting coating composition is applied to an arbitrary substrate and dried to provide a film containing the zinc oxide-based particles. The substrate includes plastic films or sheets, such as a polyester film; fiber, such as natural fiber or synthetic fiber; transparent or semitransparent synthetic resin plates made of, e.g., vinyl chloride resins, polycarbonate resins, acrylic resins, and a polyethylene terephthalate resin; glass; and paper.

If necessary, the coating film may be heated at a temperature below the deformation temperature of the substrate for the following purposes. To accelerate condensation reaction among the molecules of an inorganic binder component, e.g., a silicon alkoxide, thereby to form a tough film; to accelerate curing reaction of a thermosetting resin as a binder component, thereby to provide a cured film; and to help efficient progress of crosslinking reaction between a resin having two or more active hydrogen atoms, such as polyether and/or polyester, which is used as at least part of the binder component, and a crosslinking agent, such as an isocyanate compound, thereby to form a polyurethane film.

The coated film of the coated article of the invention is a film formed on drying or dry-curing (dry-crosslinking) the above-mentioned organic and/or inorganic binder.

The method of applying the coating composition of the invention is not particularly limited, and any known coating technique, such as dipping, spraying, screen printing, roll coating, and flow coating, can be used.

The coating film thus formed of the coating composition of the invention and the resulting coated articles of the invention comprises the binder component having dispersed therein the zinc oxide-based fine particles of the invention. Therefore, the coating film and the coated article exhibit the functions reflecting the characteristics possessed by the fine particles. That is, they have (a) UV-cutting power. Where the zinc oxide-based particles obtained by the process described in (27) to (36) or the zinc oxide-based particles described in (50) to (58) are used, the coating film and the coated article additionally have (b) infrared (IR; inclusive of near infrared rays (=heat rays) and far infrared rays)-cutting power and (c) controlled electrical conductivity. Where ultrafine particles are used, the coating film is excellent in visible light transmitting properties (=transparency). Where fine particles having a double layer structure, such as hollow particles, are used, the coating film is excellent in light scattering properties.

Since the zinc oxide-based fine particles of the invention mainly comprise ZnO, they have excellent antimicrobial properties, thereby providing coated articles having an antimicrobial action.

When all the fine particles in the coating composition are regular in shape and have a number average particle size of 0.1 to 10 $\mu$m with a coefficient of size variation of not more than 30%, the resulting coated film and the coated article exhibit at least the characteristics (a) to (c) and, in addition, slip properties and anti-blocking properties while retaining surface flatness.

[2] Resin Composition and Resin Molded Articles of the Invention

The resin composition according to the invention comprises at least one kind of the zinc oxide-based fine particles of the invention and a resin capable of forming a continuous phase in which the zinc oxide-based fine particles are dispersed. The amount of zinc oxide-based fine particles and the resin is 0.1 to 99% by weight and 1 to 99.9% by weight, respectively, based on their total solids content.

If the amount of the fine particles is larger than the above range, the resulting molded article tends to have insufficient mechanical strength. If the amount is smaller than the above range, the effects of the fine particles may not be exerted fully.

The resin molded article of the invention is an article obtained by molding the resin composition of the invention into a shape selected from the group consisting of a plate, a sheet, a film, and fiber.

The resin used in the resin composition and the resin molded article is not particularly limited in kind and is selected appropriately according to the end use. Illustrative examples of useful resins are (1) thermoplastic or thermosetting resins, such as polyolefin resins (e.g., polyethylene and polypropylene), polystyrene resins, vinyl chloride resins, vinylidene chloride resins, polyvinyl alcohol, polyester resins (e.g., polyethylene terephthalate and polyethylene naphthalate), polyamide resins, polyimide resins, (meth) acrylic resins (e.g., polymethyl (meth)acrylate), phenolic resins, urea resins, melamine resins, unsaturated polyester resins, polycarbonate resins, and epoxy resins, and (2) natural or synthetic rubbers, such as ethylene-propylene copolymer rubber, polybutadiene rubber, styrene-butadiene rubber, and acrylonitrile-butadiene rubber. These resins are used either individually or as a combination of two or more thereof.

The process for preparing the resin composition of the invention is not particularly limited, and the resin composition can be obtained by mixing and dispersing the fine particles of the invention in the resin. For example, the resin composition can be obtained by a conventionally known process, such as a masterbatching process, in which powder of the fine particles is added to the melt-kneading system of a pelletized or powdered resin, or a process comprising dispersive mixing of the fine particles in a resin solution followed by solvent removal. Alternatively, a process comprising dispersive mixing of the fine particles in the course of resin preparation can also be adopted. In the case of using polyester, for instance, powder of the fine particles, preferably a dispersion of the fine particles in the glycol component used as a starting material of the polyester, is added to the polyester preparation system at any stage of from interesterification through polymerization.

According to the above-described processes, there is obtained a resin composition comprising the resin having dispersed therein the fine particles of the invention. The resin composition can be formed into a general molding compound, such as pellets. On molding, the resin composition provides a molded article in the form of a plate, a sheet, a film, fiber, etc. which contains the fine particles of the invention and exhibits UV-cutting power. Where the zinc oxide-based particles obtained by the process described in (27) to (36) and the zinc oxide-based particles described in (50) to (58) are used, the molded article additionally has IR (inclusive of near infrared rays (=heat rays) and far infrared ryas)-cutting power and controlled electrical conductivity. Where ultrafine particles are used, it has excellent visible light transmitting properties (=transparency). Where fine particles having a double layer structure, such as hollow particles, are used, the molded article is excellent in light scattering properties.

Since the zinc oxide-based particles of the invention mainly comprise ZnO, they have excellent antimicrobial properties, thereby providing molded articles having an antimicrobial action.

When all the fine particles in the resin composition are regular in shape and have a number average particle size of 0.1 to 10 $\mu$m with a coefficient of size variation of not more than 30%, the resulting resin molded article exhibits slip properties and anti-blocking properties while retaining surface flatness. The molded article in film form, particularly an oriented film obtained by stretching the molded film has surface unevenness ascribed to the presence of the fine particles. In using the fine particles obtained in accordance with preferred embodiments of the invention, i.e., the particles regular in size and highly dispersed, the film has uniform and fine surface unevenness and excellent slip properties or anti-blocking properties while retaining extremely high flatness. For example, polyester films obtained in this way are useful as a base of magnetic tapes, wrap film or a film of a condenser.

The process of obtaining a molded article in a desired shape from the resin composition of the invention is not particularly limited, and conventional molding techniques can be adopted as they are. Illustrative examples of molding are shown below.

In the production of a polycarbonate resin plate containing the fine particles of the invention, pellets or powder of a polycarbonate resin and powder of a prescribed amount of the fine particles are melt kneaded to prepare a composition in which the fine particles are uniformly dispersed in the resin. The composition, either as it is or after pelletized, is then molded by injection molding, extrusion, compression molding, and the like into a flat or curved plate shape. As a matter of course, the resulting plate-shaped article can further be subjected to post processing into an arbitrary shape, such as a wavy plate shape. Plates of other resins, such as acrylic resins, vinyl chloride resins, and polyester resins, can also be obtained similarly.

In the production of fibers (e.g., nylon fiber and polyester fiber) or films (e.g., a polyolefin film, a polyamide film or a polyester film) containing the fine particles of the invention, powder of the fine particles and pellets or powder of a resin are melt kneaded to prepare a composition in which the fine particles are uniformly dispersed in the resin. The composition, either as it is or after pelletized, is then molded into fiber by a conventional technique, such as melt spinning, or sheeted by a conventional sheeting technique, such as extrusion into a sheet, which is, if necessary, uniaxially or biaxially stretched then.

The resin molded article of the invention includes laminated films or sheets comprising one or more layers containing the fine particles of the invention, which can be used as wrap film for food, etc., heat insulating film, gas barrier film, and the like. The laminated films or sheets can be produced by, for example, a process of laminating a film or sheet containing the fine particles of the invention with other films or sheets by heat fusion or via an adhesive (or an adhesive layer) or a process of coating a film or sheet with the above-described coating composition of the invention. Further, a laminated film or sheet can be produced by co-extruding (1) a composition of powder of the fine particles of the invention and resin pellets or powder or (2) resin pellets or powder previously containing the fine particles of the invention onto a base film or sheet or any functional film or sheet. Apparatus used therefor can be a conventional film extruder used for production of a multi-layer film or sheet.

Polyester fiber or polyester film having dispersed therein the fine particles of the invention can also be produced by the following conventional process.

Polyester fiber can be obtained by adding a dispersion of the fine particles, for example, a 0.1 to 50 wt % dispersion in a glycol component, to the polyester preparation system at any stage of from interesterification through polymerization, followed by completion of the polymerization reaction to obtain a polyester resin having dispersed therein the fine particles and melt spinning the resulting polyester resin in a conventional manner.

A polyester film can be obtained by preparing a polyester resin having dispersed therein the fine particles in the same manner as described above and extruding the resin into a sheet. If desired, the extruded sheet is stretched uniaxially or biaxially.

[3] Paper of the Invention

Paper according to the invention comprises pulp made into paper and at least one kind of the zinc oxide-based fine particles of the invention dispersed in the pulp. The amount of the zinc oxide-based fine particles is 0.01 to 50% by weight, preferably 0.1 to 20% by weight, based on the pulp. If the amount of the particles is smaller than 0.01%, the effects of addition of the fine particles are insufficient. If it exceeds 50%, the paper has reduced mechanical characteristics.

The paper as referred to herein is not restricted as far as it contains the fine particles of the invention and includes, for example, self-containing paper, coated paper, impregnated paper, and processed paper, such as film-laminated paper.

The terminology "self-containing paper" means paper having the fine particles dispersed in the inside thereof and/or on the outer surface thereof, which is obtained by adding the fine particles in an arbitrary stage of from beating of pulp through paper making. The manner of addition of the fine particles is not particularly limited. The fine particles are usually added in powder form or as dispersed in, e.g., water. The steps involved up to paper making and drying are carried out in accordance with conventionally known paper making techniques. Conventionally known raw materials can be used in the invention. For example, pulp is beaten by means of a pulper, etc. to prepare a pulp slurry, and an aqueous dispersion of the fine particles of the invention is added to the slurry. The pulp slurry is then made into paper and dried to obtain paper having dispersed therein the fine particles. If desired, a sizing agent, ammonium sulfate, a strengthening agent, etc. can be added in an arbitrary stage.

Coated paper is paper obtained by applying a coating composition containing the fine particles of the invention to a paper base and drying to form a coating film containing the fine particles. Impregnated paper is paper having the fine particles adhered on one or both sides thereof, which is obtained by impregnating a paper base with a dispersion of the fine particles in an aqueous or organic medium which may contain a binder, followed by drying.

Preparation of the coated paper and the impregnated paper is not particularly restricted, and any known coating or impregnation technique can be applied, using paper prepared by a general paper making process as a base, except for using the fine particles of the invention.

The fine particles-containing coating composition or dispersion to be used are prepared in a conventional manner using conventional raw materials, and the solvent or the binder to be used can be those conventionally employed.

The content of the fine particles in the coating composition or the dispersion is not further limited as long as it is within a range of from 0.1 to 100% by weight based on the solids content, and is decided appropriately according to the use, and the like.

The term "solids content" as used above means the total weight of the fine particles of the invention and a binder in the coating composition or the dispersion. The coating composition used for producing coated paper can be the one that is included in the above-described coating compositions according to the invention and contains a solvent. The dispersion medium of the dispersion used for producing coated paper can be the solvent usable in the above-described coating compositions of the invention. The coating composition may further contain additives, such as pigments, water repellents, lubricants, defoaming agents, fluidity modifiers, and water retaining agents, in addition to the above-described components in accordance with the purpose of use.

Film-laminated paper is paper composed of a paper base and a high polymer film bonded thereto, the high polymer film having dispersed therein the fine particles obtained by the above-described processes. The high polymer film can be the above-described resin molded article according to the invention.

The paper containing the fine particles of the invention which can be obtained by the above-mentioned processes is useful as paper with excellent appearance. The use of the resulting paper is arbitrary, and the paper finds a variety of applications as, for example, art paper or wall paper.

When all the fine particles contained in the paper are regular in shape and have a number average particle size of 0.1 to 10 $\mu$m with a coefficient of size variation of not more than 30%, preferably a number average particle size of 0.1 to 2 $\mu$m with a coefficient of size variation of not more than 15%, the paper possesses excellent surface flatness not heretofore attained and improved printability.

[4] Cosmetics of the Invention

The cosmetics according to the invention contain at least one kind of the zinc oxide-based fine particles of the invention in an amount of 0.1% by weight or more. The amount of the zinc oxide-based fine particles is usually from 0.1 to 50% by weight based on the total solids content of the cosmetics. As far as the effects of the invention are not impaired, the cosmetics contain other components commonly used in cosmetics in addition to the above essential component according to the purpose. For example, (1) one or more of oils, such as liquid fats and oils, solid fats and oils, waxes, and hydrocarbons, and polyhydric alcohols, such as polyethylene glycol and propylene glycol, and (2) one or more of surface active agents, thickeners, perfumes, drugs, antioxidants, chelating agents, coloring matter, water, antiseptics, antifungals, and the like can be added. Further, (3) one or more pigments selected from extender pigments, such as kaolin, talc, and mica, inorganic pigments, such as an iron oxide pigment and a $TiO_2$ pigment, and organic pigments, such as red #202 and yellow #4 and/or (4) one or more of organic UV absorbers, such as benzoic acid type, cinnamic acid type, salicylic acid type or benzophenone type UV absorbers can also be used in combination with the fine particles of the invention.

The cosmetics of the invention are superior cosmetics that can screen out ultraviolet light and are also excellent in antimicrobial properties and deodorizing properties. The purpose of incorporating the fine particles into the cosmetics includes anti-sunburn, furnishing antimicrobial activity, and furnishing deodorizing properties, varying depending on the composition, morphology, particle size, etc. of the fine particles used. For example, addition of the zinc oxide-based particles obtained by the process described in (27) to (36) or the zinc oxide-based particles described in (50) to (58) produces an effect of screening heat rays. Addition of the zinc oxide-polymer composite particles obtained by the process described in (10) to (18) or the zinc oxide-polymer composite particles described in (37) to (42) gives an effect of improving smoothness. Addition of hollow particles affords an effect of improving transparency, and addition of porous particles brings about an effect of improving moisture retention.

The use of the cosmetics of the invention is not particularly limited. The forms the cosmetics can take include powdery, creamy or oily foundation; skin-care cosmetics, such as clear lotion, emulsion, beauty oil, and cream; and makeup cosmetics, such as lipstick and eye shadow.

The cosmetics of the invention are not further limited in composition as far as the fine particles are contained, comprising a conventional cosmetic composition having incorporated therein the fine particles. Accordingly, raw materials generally used in cosmetics can be used as such.

Accordingly, the process for producing the cosmetics of the invention is not particularly limited provided that a requisite amount of the fine particles is added and dispersed in any arbitrary stage of conventional preparation of a cosmetic composition according to the use or kind of the cosmetics. Since the fine particles of the invention are hardly agglomerated and easily dispersible in general cosmetic compositions, a dispersive mixing method commonly used for powdery materials of cosmetics can be applied to provide cosmetics in which the fine particles are highly dispersed. The fine particles may be added as such or, if desired, can be subjected to a surface treatment commonly employed for powdery cosmetic materials for rendering lipophilic or hydrophilic, for example, a treatment with an anionic, cationic, nonionic or amphoteric surface active agent, a metallic soap, silicone, etc. The surface treatment may be conducted either before or during the addition and mixing.

The cosmetics of the invention have at least UV-cutting power. Additionally, when the zinc oxide-based particles obtained by the process described in (27) to (36) or the zinc oxide-based particles described in (50) to (58) are used, the cosmetics exhibit IR (inclusive of near infrared rays (=heat rays) and far infrared ryas)-cutting power. When the zinc oxide-polymer composite particles obtained by the process described in (10) to (18) or the zinc oxide-polymer composite particles described in (37) to (42) are used, smoothness is imparted to give excellent texture. When ultrafine particles are used, the cosmetics have excellent visible light transmitting properties (=transparency). when fine particles having a double layer structure, such as hollow particles, are used, the cosmetics have light scattering properties and transparency.

Since the zinc oxide-based particles of the invention mainly comprise ZnO, they have excellent antimicrobial properties, thereby providing cosmetics articles having an antimicrobial action.

When fine particles having interstices among crystals and/or a hollow structure are used, the cosmetics have moisture retaining properties and give a moisturized feeling. A perfume and the like can be held in such particles so as to be released slowly.

The zinc oxide-polymer composite particles obtained by the process described in (10) to (18) and the zinc oxide-polymer composite particles described in (37) to (42), particularly those having a double layer structure whose outer shell is made up by agglomeration of the above-described zinc oxide-based fine particles, exhibit high light diffusing properties. Therefore, coated articles obtained by coating a transparent or semitransparent substrate (e.g., glass or plastics) with a coating composition containing such composite particles and resin molded articles formed of a resin composition containing such composite particles are useful as a diffuser applicable to those members which require light diffusion, such as covers of general lights, emergency lights, guiding lights, indicator lights, etc.; display plates or panels; light transmitting covers; signs or markers and screens for image projection; and diffusers for back-lighting liquid crystal displays (LCD). Of the coating compositions containing such composite particles, those for printing ink are especially useful for offset printing because the composite particles effectively serve as a matting agent. Further, diffusers containing the composite particles and thereby showing improved transparency to visible light and improved visible light diffusion are effective for size or thickness reduction of such equipment as LCD or lights.

The coating composition containing the above-mentioned composite particles preferably comprises the composite particles of the invention, a binder component capable of forming a transparent or semitransparent continuous phase, and a solvent capable of dispersing and/or dissolving the binder component having dispersed therein the composite particles. The amount of the composite fine particles is, for example, 0.1 to 80% by weight, preferably 0.5 to 50% by weight, based on the total solids content of the composite fine particles and the binder component.

The coated article obtained by using the above-mentioned composite particles comprises a substrate and a coating film formed on the surface of the substrate. The substrate is, for example, at least one of a resin molded article, glass, and paper. The resin molded article is, for example, at least one of a plate, a sheet, a film, and fiber. The substrate is preferably transparent and/or semitransparent and includes synthetic resins, such as (meth)acrylic resins, polycarbonate resins, polyester resins, polyimide resins, vinyl chloride resins, polystyrene resins, and polyolefin resins; and glass. The coating film comprises the composite particles of the invention and the binder component forming a transparent or semitransparent continuous phase in which the composite particles are dispersed. The amount of the composite particles is, for example, 0.1 to 80% by weight, preferably 0.5 to 50% by weight, based on the total solids content of the composite particles and the binder component.

If the amount of the composite particles exceeds the above range, the coating film has insufficient adhesion to the substrate and poor scratch resistance or abrasion resistance. If it is lower than that range, the effects of adding the composite particles are insufficient.

The above-described coating composition contains the composite particles and the binder component in a total solids content of 1 to 80% by weight and 10 to 99% by weight of a solvent, both based on the total weight of the composition. The balance of the composition comprises additives added according to necessity, such as pigments.

Where the composite particles have an outer shell made by agglomeration of the zinc oxide-based fine particles, light scattering also takes place at the interface between the outer shell and the inside, to thereby provide a coating film and a coated article with excellent light diffusing properties. Where the polymer also exists in the outer shell and the composite particles are hollow, these characteristics are further enhanced.

The resin composition containing the composite particles contains the composite particles of the invention and a resin capable of forming a transparent or semitransparent continuous phase. The amount of the composite fine particles is, for example, 0.1 to 80% by weight, preferably 0.2 to 20% by weight, based on the total solids content of the composite fine particles and the resin.

The resin molded article is an article obtained by molding the above-described resin composition into a shape selected from the group consisting of a plate, a sheet, a film, and fiber. The resin molded article contains the composite particles of the invention and a resin forming a transparent or semitransparent continuous phase in which the composite particles are dispersed. The amount of the composite particles is, for example 0.1 to 80% by weight, preferably 0.1 to 20% by weight, based on the total solids content of the composite particles and the resin.

Where the composite particles have an outer shell made by agglomeration of the zinc oxide-based fine particles, since light scattering also takes place at the interface between the outer shell and the inside, the resulting resin molded article has excellent light diffusing properties. Where the polymer also exists in the outer shell and the composite particles are hollow, these characteristics are further enhanced.

Accordingly, the coating compositions, coated articles, resin compositions, resin molded articles and cosmetics containing the above-described composite particles have:

(1) light diffusing properties and light transmitting properties which owe to the composite particles and are controlled according to the end use, (2) UV screening properties, (3) high dispersibility in cosmetic compositions, and (4) antimicrobial and antifungal (antibacterial) actions.

The zinc oxide-polymer composite particles obtained by the process described in (10) to (18), the zinc oxide-based fine particles obtained by the process described in (27) to (36), the zinc oxide-polymer composite particles described in (37) to (42), and the zinc oxide-based fine particles described in (50) to (58) can have their light diffusing properties and light transmitting properties controlled in conformity with the end use. Therefore, a resin layer containing these composite particles or zinc oxide-based particles can be used advantageously as a diffuser for backlighting liquid crystal displays.

The process for producing the diffuser is not particularly limited. The diffuser can be produced in accordance with the above-mentioned processes for producing a coated article and a resin molded article.

Resins and additives which constitute a diffuser are not limited, and those used in the above-described resin molded articles can be used. Preferred resins for diffusers are at least one of polyethylene terephthalate resins, polycarbonate resins, and (meth)acrylic resins.

A diffuser as a coated article can be obtained by applying the above-described coating composition containing a binder to a transparent substrate to form a coating film. A preferred substrate is usually a polyester film or sheet or a polycarbonate film or sheet.

The inorganic compound particles obtained by the process described in (19) to (26) and the inorganic compound particles described in (43) to (49) contain 60 to 100% by weight of zinc oxide and have on their surface a cluster of thin plates with their tips projecting outward. Therefore, they are multifunctional fine particles having the following characteristics:

(1) having abnormal light diffusion characteristics, (2) scattering electromagnetic waves in the near infrared region without reducing a percent diffused transmission in the visible light, (3) being a porous body having an uneven surface and a large surface area, (4) having ultraviolet absorbing and scattering power, (5) being a light semiconductor, and (6) having antimicrobial and antifungal actions.

Since the inorganic compound particles function as porous particles or microcapsules, they are useful as antimicrobial agents, gas adsorbents, controlled releasing agents and adsorbents as well as the above-mentioned uses. Structures of these products containing the inorganic compound particles and process for manufacturing them are not particularly limited, and conventionally known structures and methods are used.

BEST MODE FOR CARRYING OUT THE INVENTION

Figure 1:
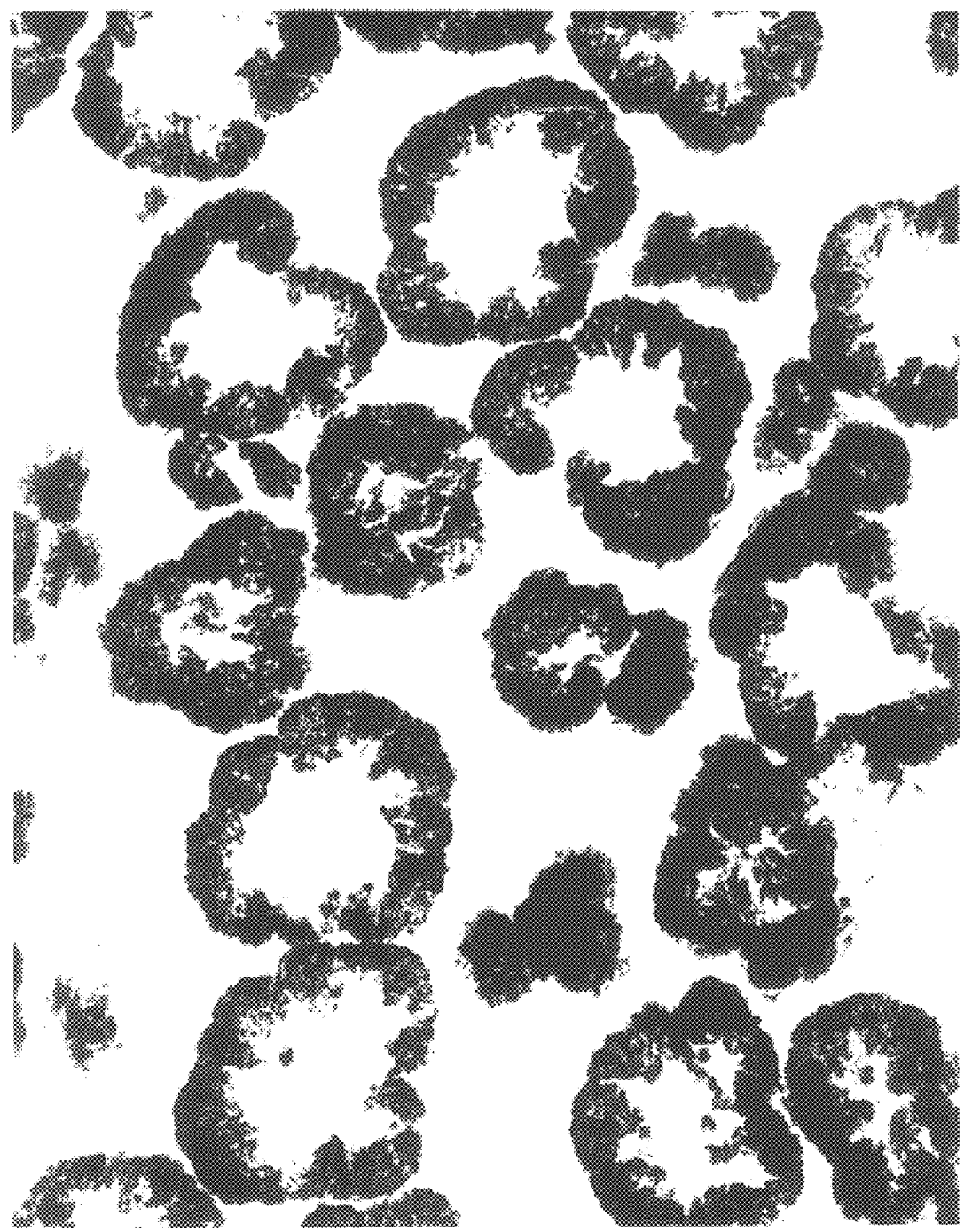
FIG. 1 is a transmission electron micrograph of powder P14 obtained in Example 14.

The present invention will now be illustrated in greater detail by way of Examples, but the invention should not be construed as being limited thereto.

For each dispersion of zinc oxide-based fine particles obtained, various physical properties such as the crystalline properties of the fine particles, the shape of the particles, the primary particle size, the state of dispersion or agglomeration, the concentration of the fine particles, the compositions, and the like were analyzed and evaluated according to the following methods. When the dispersion obtained in Examples should be powdered prior to the analysis and evaluation, it was powdered in accordance with the following method, and the resulting powder sample was subjected to measurement.

The fine particles obtained in Examples in powder form were subjected to all analyses as they were.

(Preparation of Powder Sample)

The fine particles of a dispersion were separated by centrifugation and dried at 80° C. in vacuo to completely drive out the volatile matter to obtain powder of the fine particles.

(Crystalline Properties)

Evaluated through powder X-ray diffractometry.

(Particle Shape)

Observed through a scanning electron microscope or a transmission electron microscope at a magnification of 10,000.

(Particle Size)

The particle diameters of arbitrarily selected 100 particles on a scanning electron micrograph or a transmission electron micrograph of 10,000 magnifications were measured to obtain an average particle size according to the following equation. In the case of using a scanning electron microscope, a noble metal alloy is deposited on the particles by vacuum evaporation prior to the measurement. Because the measured particle size is increased by the thickness of the deposit as compared with that obtained through a transmission electron microscope, the measured value was corrected accordingly.

Average particle size d: number average particle size

Di: particle size of individual particles n: number of particles (State of Dispersion or Agglomeration)

Evaluated by means of an optical microscope and a centrifugal precipitation type particle size distribution measuring apparatus and graded as follows:

A: Primary particles are dispersed.

B: Primary particles are partly agglomerated.

C: Primary particles are agglomerated.

(Concentration of Particles in Dispersion)

An aliquot of a dispersion was vacuum dried at 100° C. until the volatile matter such as a solvent was completely removed. The weight ratio of the resulting powder to the dispersion was taken as a concentration of the particles in the dispersion.

(Solvent Composition in Dispersion)

The solvent in a dispersion was separated by centrifugation and identified and determined by mass spectrometry and gas chromatography.

(Composition of Particles)

The composition of particles was determined by total judgement of the analytical results of a powdered sample obtained through elementary analysis, ion chromatography, IR absorption spectrophotometry, NMR, X-ray fluorometry, atomic-absorption spectroscopy, gravimetric analysis, and the like.

(Coefficient of Particle Size Variation)

The particle diameters (major axes) of arbitrary selected 100 particles on a scanning electron micrograph under 10,000 magnifications were measured to obtain a number average particle size of fine particles. The coefficient of particle size variation was calculated therefrom according to equation:

$$CV = 100 \sigma_{n-1}/d_n$$

CV: coefficient of variation of particle size $\sigma_{n-1}$: standard deviation of particle size distribution $d_n$: number average particle size The standard deviation of particle size distribution is calculated from equation:

$$\sigma_{n-1} = \left( \sum_{i=1}^{n} (d_n - D_i)^2 \right)^{1/2} \Big/ (n-1)$$

(Particle Shape)

Judged on the basis of an L/B (major axis/minor axis) ratio obtained by measurement on 100 particles on a scanning electron micrograph under 10,000 magnifications. The L/B ratio was obtained from equation:

$$L/B \text{ ratio} = \left( \sum_{i=1}^{n} (L_i/B_i) \right) \Big/ n$$

$L_i$: major axis of individual particles $B_i$: minor axis of individual particles Particles having an L/B ratio of 1.0 or higher and lower than 1.2 were judged to be spherical, and those having an L/B ratio of 1.2 to 5.0 were judged to be ellipsoidal.

(Size and Shape of Zinc Oxide Fine Particles)

Judged through a scanning electron microscope or a transmission electron microscope under 10,000 to 100,000 magnifications.

The micrograph of the cut section of composite fine particles was obtained by embedding the composite fine particles into a resin, slicing the preparation to prepare an ultrathin section, which was observed under a transmission electron micrograph.

(Composition of Fine Particles (Zinc Oxide Concentration))

A powdered sample was calcined in air at 600° C. for 2 hours, and the weight ratio of the resultant ash, taken as zinc oxide, was obtained.

(Optical Characteristics of Fine Particles-Containing Film, etc.)

A transmission at 800 to 200 nm was measured with an autographic spectrophotometer (UV-3100, manufactured by Shimadzu Corporation) to obtain a (total) transmission in the visible region, UV screening power, etc. as spectral characteristics.

The total transmission and a haze were measured with a turbidimeter (NDH-1001 DP, manufactured by Nihon Denshoku Kogyo K.K.).

(Specific Surface Area and Pore Size Distribution of Fine Particles)

Using a powdered sample, a BET specific surface area, a pore size distribution, etc. were measured by means of a full-automatic gas adsorption measuring apparatus (AUTOSORB-6, manufactured by Yuasa-Ionics).

(Size and Shape of Thin Crystal Grains)

Observed under a scanning electron microscope or a transmission electron microscope at a magnification of 10,000 to 100,000.

The micrograph on the section was taken of an ultrathin section of resin-embedded fine particles under a transmission electron microscope.

(State of Dispersion or Agglomeration)

Evaluated by means of an optical microscope and a centrifugal precipitation type particle size distribution measuring apparatus and graded as follows:

A: Fine particles are dispersed without being agglomerated.

B: Fine particles are partly agglomerated.

C: Fine particles are agglomerated.

The weight average particle size $d_w$ of the fine particles in a dispersion was measured with a centrifugal precipitation type particle size distribution measuring apparatus.

(Optical Characteristics of Fine Particles (Heat Ray-Cutting Performance, etc.))

A dispersion of fine particles as obtained by reaction was concentrated to obtain a concentrated dispersion having a particle concentration of 10% by weight. The concentrated dispersion was applied to a 2 mm thick glass plate by means of a bar coater with the coating weight being varied from 1 to 10 g/m$^2$ in terms of the fine particles, and dried at 80° C. in a nitrogen atmosphere to form a dry film. The spectral characteristics of each dry film were measured at a wavelength of 2200 to 200 nm with an autographic spectrophotometer (UV-3100, manufactured by Shimadzu Corporation). The spectral curve obtained for the film having a coating weight of 3 g/m$^2$ in terms of the fine particles was examined to evaluate the performances based on the following standards.

| Standard | Grade |
|---|---|
| UV cutting power: | |
| Transmission at 350 nm: | |
| ≦1% | A |
| 1 to 10% | B |
| >10% | C |
| Heat ray cutting power: | |
| Cut* at 2 μm: | |
| >40% | +++ |
| 20 to 40% | ++ |
| <20% | + |

-continued

| Standard | Grade |
|---|---|
| Visible light transmission:<br>Transmission at 600 nm: | |
| ≧80% | +++ |
| 70 to 80% | ++ |
| 60 to 70% | + |
| <60% | − |

*Cut of heat rays = [transmission (%) of substrate at 2 μm] − [transmission (%) of coated article at 2 μm]

For reference, the transmissions of the glass substrate plate used were as follows.

| wavelength: | 350 nm | 600 nm | 2 μm |
|---|---|---|---|
| Transmission (%): | 86 | 91 | 91 |

(Optical Characteristics of Coated Article)

Spectral characteristics of coated articles were evaluated by measuring the transmission at various wavelengths from 2200 to 200 nm with an autographic spectrophotometer (UV-3100, manufactured by Shimadzu Corporation).

Based on the results of measurement, the performances were evaluated as follows.

Heat ray cut=[transmission (%) of substrate at 2 μm]−[transmission (%) of coated article at 2 μm]

UV cutting power was evaluated in terms of transmission at 350 nm.

A total transmission and a haze value were measured with a turbidimeter (NDH-1001 DP, manufactured by Nihon Denshoku Kogyo K.K.).

(Electrical Conductivity of Fine Particles)

A powdered sample measuring 0.1 ml was sandwiched in between a 1.5 cm-square Pyrex glass plate having a comb type electrode formed thereon by vacuum evaporation of gold and a 1.5 cm-square Pyrex glass plate having no deposit. After the test piece was allowed to stand for 1 hour with a given pressure applied thereon at a temperature of 20° C. and 60% RH under shielding from light, the electric current (dark current) was measured under the above conditions with Electrometer 617 (manufactured by Kesley Corp.), which was converted to a surface resistivity (Ω).

The conductivity of the sample was evaluated by comparing the thus obtained resistivity with that of commercially available zinc oxide (Aenka 1-Go Tokusei, produced by Sakai Chemical Industry Co., Ltd.) as a reference sample. That is, evaluation was made based on r value (=resistivity of the reference sample/resistivity of the sample under analysis).

| Range of r Value | Grade of Conductivity |
|---|---|
| $1 \times 10^{-1} \leq r < 1 \times 10^{1}$ | − |
| $1 \times 10^{1} \leq r < 1 \times 10^{2}$ | + |
| $1 \times 10^{2} \leq r < 1 \times 10^{3}$ | ++ |
| $1 \times 10^{3} \leq r$ | +++ |

EXAMPLE 1

In a 10 l glass-made reactor equipped with a stirrer, a dropping opening, a thermometer, and a reflux condenser, 1.2 kg of acetic acid was dissolved in a mixed solvent of 2.0 kr of methanol and 2.0 kg of ion-exchanged water, and 1.08 kg of zinc acetate dihydrate was added thereto. The mixture was heated up to 60° C. while stirring to obtain a unifor zinc-containing solution (A1).

In a 20 l glass-made reactor which was equipped with a stirrer, a dropping opening, a thermometer, and an outlet for distillate gas and could be heated by an external heating medium, 12 kg of benzyl alcohol was charged, and the inner temperature was raised up to 150° C. and maintained at that temperature. To the heated benzyl alcohol was added dropwise 6.28 kg of the zinc-containing solution (A1) kept at 60° C. over a period of 30 minutes by means of a constant delivery pump. The temperature of the alcohol-based system varied from 150° C. to 138° C. After the dropwise addition, the inner temperature was elevated to 200° C., and the mixture was maintained at that temperature for 5 hours to obtain 5.80 kg of a white dispersion (D1). The dispersion (D1) was a dispersion in which crystalline zinc oxide fine particles having a primary particle size of 40 to 90 nm were dispersed in a considerably secondarily agglomerated state in a solvent mainly comprising benzyl alcohol. As a result of a compositional analysis, the dispersion (D1) was found to have a zinc oxide fine particle concentration of 7.0 wt % and, as a solvent component, a benzyl alcohol content of 61.4 wt % and a benzyl acetate content of 31.6 wt %. The physical properties of the dispersion (D1) and the zinc oxide fine particles in the dispersion (D1) are shown in Table 2 below.

EXAMPLE 2

In the same glass reactor as used in Example 1, 0.3 kg of commercially available zinc oxide powder was mixed with a mixed solvent of 1.5 kg of acetic acid and 1.5 kg of ion-exchanged water, followed by heating to 80° C. while stirring to prepare a uniform zinc-containing solution (A2).

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 150° C. and maintained at that temperature. To the heated alcohol was added dropwise 3.3 kg of the zinc-containing solution (A2) kept at 80° C. over a 30-minute period by means of a constant delivery pump. The temperature of the alcohol-based system varied from 150° C. to 128° C. After the dropwise addition, the inner temperature was increased. When the temperature reached 160° C., 0.15 kg of a solution of 0.015 kg of lauric acid in 2-butoxyethanol was added thereto and mixed. The temperature was further increased to 170° C., at which the mixture was maintained for 4 hours to obtain 9.9 kg of a milky white dispersion (D2).

The dispersion (D2) was substantially a monodispersion in which crystalline zinc oxide fine particles having a uniform primary particle size of 20 nm were dispersed. The physical properties of the dispersion (D2) and the zinc oxide fine particles in the dispersion (D2) are shown in Table 2 below.

EXAMPLE 3

A dispersion of zinc oxide fine particles was prepared in the same manner as in Example 2, except for altering the reaction conditions, such as the kind or amount of the raw materials and the additive, as shown in Table 1 below. The resulting dispersion was concentrated by evaporating part of the solvent by means of an evaporator under reduced pressure at 120° C. The concentration was adjusted with 2-butoxyethanol to give a dispersion containing 10 wt % of zinc oxide fine particles (D3). The physical properties of the dispersion (D3) and the zinc oxide fine particles in the dispersion are shown in Table 2 below.

EXAMPLE 4

A dispersion of zinc oxide fine particles was prepared in the same manner as in Example 2, except for altering the reaction conditions, such as the kind or amount of the raw materials and the additives, as shown in Table 1 below. The resulting dispersion was concentrated by evaporating part of the solvent by means of an evaporator at 120° C. under reduced pressure. The concentration was adjusted with 2-butoxyethanol to give a dispersion containing 25 wt % of zinc oxide fine particles (D4). The physical properties of the dispersion (D4) and the zinc oxide fine particles in the dispersion are shown in Table 2 below.

EXAMPLE 5

A dispersion of zinc oxide fine particles (D5) was prepared in the same manner as in Example 2, except for altering the reaction conditions, such as the kind or amount of the raw materials, as shown in Table 1 below. The physical properties of the dispersion (D5) and the zinc oxide fine particles in the dispersion are shown in Table 2 below.

TABLE 1

| | Zinc-Containing Solution | | | | Alcohol-Containing Solution | | Heating Temperature (° C.) |
|---|---|---|---|---|---|---|---|
| Example No. | Zinc-Containing Compound | Carboxyl-Containing Compound | Solvent | Solution Temperature (° C.) | Alcohol | Additive | |
| 1 | zinc acetate dihydrate (1.08) | acetic acid (1.2) | water (2.0) methanol (2.0) | 60 | benzyl alcohol (12) | — | 200 |
| 2 | zinc oxide (0.3) | acetic acid (1.5) | water (1.5) | 80 | 2-butoxy-ethanol (12) | lauric acid (0.015) | 170 |
| 3 | zinc hydroxide (0.36) | acetic acid (4.0) | water (1.5) | 80 | 2-butoxy-ethanol (12) | lauryl-amine (0.033) | 174 |
| 4 | zinc hydroxide (0.36) | acetic acid (4.0) | water (1.5) | 80 | 2-butoxy-ethanol (12) | Softanol M70 (0.067) | 170 |
| 5 | basic zinc carbonate*[1] (0.020) zinc oxide (0.285) | acetic acid (1.5) | water (1.5) | 80 | 2-butoxy-ethanol (12) | — | 174 |

Note:
*[1]: ZnO content: 74 wt %
The values in the parentheses indicate part(s) by weight.

TABLE 2

| | | | Average | | Composition of Dispersion (wt %) | | |
|---|---|---|---|---|---|---|---|
| Example No. | Crystalline Properties | Particle Shape | Primary Particle Size (nm) | State of Dispersion or Agglomeration | Zinc Oxide Fine Particles | Alcoholic Solvent | Ester Compound |
| 1 | crystal | granular | 70 | C | 7.0 | 61.4 | 31.6 |
| 2 | " | granular | 20 | A | 3.0 | 82.0 | 14.9 |
| 3 | " | granular | 30 | B | 10.0 | 41.0 | 49.0 |
| 4 | " | granular | 20 | B | 25.0 | 40.0 | 35.0 |
| 5 | " | granular | 15 | A | 4.2 | 76.1 | 19.7 |

EXAMPLE 6

The dispersion (D2) obtained in Example 2 was concentrated in the same manner as in Example 3 to obtain a concentrated dispersion (D6) having a zinc oxide concentration of 20 wt %. The dispersion (D6) was diluted with methanol to obtain a slurry (S6) having a zinc oxide concentration of 10 wt %. The slurry (S6) was powdered by use of a vacuum flash evaporator.

A long pipe of stainless steel measuring 8 mm in inside diameter and 9 m in length was kept heated by passing compressed steam through a jacket covering the long pipe. The slurry (S6) was continuously supplied from one end of the long pipe (slurry inlet) at a flow rate of 10 kg/hr by a metering pump. The other end of the long pipe was maintained at a reduced pressure of 50 Torr and connected to a bag filter where powder was separated from the vaporized solvent. The powder (P6) of the zinc oxide fine particles thus separated in the bag filter was collected in a powder collecting chamber also kept at 50 Torr.

The resulting powder (P6) was easily dispersible in its primary particle state in organic solvents, such as aromatic hydrocarbons (e.g., toluene), ketones (e.g., methyl ethyl ketone), esters (e.g., butyl acetate), and alcohols (e.g., methanol and isopropyl alcohol).

COMPARATIVE EXAMPLE 1

A zinc-containing solution (A1) was prepared in the same manner as in Example 1. The solution containing a zinc oxide precursor was added dropwise to a solvent in the same manner as in Example 1, except for replacing benzyl alcohol as a solvent by o-xylene. The resulting mixture was kept at 140° C. for 2 hours to obtain a suspension. X-Ray diffractometry of the suspension revealed that the fine particles contained were not zinc oxide fine particles.

COMPARATIVE EXAMPLE 2

A zinc-containing solution (A2) was prepared in the same manner as in Example 2. The solution containing a zinc oxide precursor was added dropwise to a heated solvent in the same manner as in Example 2, except for replacing 2-butoxyethanol as a solvent by ethylene glycol n-butyl ether acetate. The resulting mixture was kept at 170° C. for 2 hours to obtain a suspension. X-Ray diffractometry of the suspension revealed that the fine particles contained were not zinc oxide fine particles.

EXAMPLE 8

The dispersion (D2) obtained in Example 2 was concentrated in the same manner as in Example 3, and the concentration was adjusted with toluene to give a dispersion (D2-2) containing zinc oxide fine particles in a concentration of 10 wt %. The dispersion (D2-2) was formulated into a coating composition according to the following formulation:

| Formulation of Coating Composition | |
|---|---|
| Dispersion (D2-2) | 100 parts by weight |
| Alloset 5247 (produced by Nippon Shokubai Kagaku Kogyo Co., Ltd.; solid content: 45 wt %) | 200 parts by weight |
| Toluene | 100 parts by weight |

The coating composition was applied to each of a glass plate, a polyester film and an acrylic resin plate by means of a bar coater and dried to form a coating film. On every substrate, the coating film screened out ultraviolet rays effectively while having excellent visible light transmitting properties. In Table 3 below are shown the spectral transmission of the glass plate having the coating film (thickness: 11 μm).

COMPARATIVE EXAMPLE 3

A coating composition containing 10 wt % of zinc oxide was prepared in the same manner as in Example 8, except for using zinc oxide fine particles obtained by a French process (average primary particle size: 0.04 μm) in place of the dispersion (D2) as used in Example 8, and applied to a glass plate in the same manner to form a coating layer having a thickness of 10 μm. The coating film had lower transparency and a lower UV cutting ratio than the coating film obtained in Example 8. The spectral transmission of the glass plate having the coating film are shown in Table 3.

TABLE 3

| | Visible Light Transmission (500 nm) | UV Transmission (360 nm) |
|---|---|---|
| Coated glass plate obtained in Example 8 | 80 | 2 |
| Coated glass plate obtained in Comparative Example 3 | 73 | 10 |
| Glass plate | 90 | 86 |

EXAMPLE 9

A dispersion (D2-2) was obtained in the same manner as in Example 8 and was formulated into a coating composition according to the following formulation:

Formulation of Coating Composition
  Dispersion (D2-2) 100 parts by weight
  Silica sol 120 parts by weight
  (OSCAL 1432, produced by Shokubai Kasei Kogyo Co., Ltd.)
  Isopropyl alcohol 100 parts by weight The coating composition was applied to a glass plate by means of a bar coater and dried to form a coating film. The coating film was a scratch-resistant film having excellent visible light transmitting properties and yet UV absorbing properties.

EXAMPLE 10

Ten parts by weight of the powder (P6) obtained in Example 6 and 500 parts by weight of polycarbonate resin pellets were mixed and melt-kneaded to obtain a molten mixture having uniformly dispersed therein 2 wt % of zinc oxide fine particles. Subsequently the mixture was extruded into a polycarbonate plate (A) having a thickness of 2 mm. The polycarbonate plate (A) effectively cut ultraviolet rays while having excellent visible light transmitting properties.

EXAMPLE 11

The dispersion (D2) obtained in Example 2 was subjected to centrifugation to remove the solvent. The resultant zinc oxide fine particles containing a slight amount of a residual solvent component were dispersed in methyl methacrylate (hereinafter abbreviated as MMA), and the dispersion was again centrifuged. The above operation was repeated several times to finally obtain 50 parts by weight of an MMA dispersion containing 20 wt % of the zinc oxide fine particles.

To 50 parts by weight of the MMA dispersion was added 0.4 part by weight of a polymerization initiator V-65, and the dispersion was added to 200 parts by weight of a 5 wt % aqueous solution of Poval (PVA 205, produced by Kuraray Co., Ltd.), followed by stirring for 5 minutes. The mixture was further dispersed in a disperser to prepare a suspension containing the zinc oxide fine particles in MMA as a dispersing medium.

The suspension was put in a glass container equipped with a stirrer, a reflux condenser and a thermometer and kept at 70° C. for 30 minutes with stirring. The temperature was gradually raised, and the system was maintained at 95° C. or higher for 3 hours to cause MMA to polymerize to obtain an aqueous suspension of particles of polymethyl methacrylate (hereinafter abbreviated as PMMA) containing the zinc oxide fine particles. The suspension was centrifuged, and the solid was washed with water. After repeating the centrifugation and washing several times, the particles were dried at 60° C. to obtain PMMA particles containing the zinc oxide fine particles. As a result of analysis, the PMMA particles were found to be composite particles having a particle size of 10 to 70 $\mu$m and a zinc oxide content of 18 wt % in which the zinc oxide fine particles were uniformly dispersed in PMMA. The PMMA particles effectively cut ultraviolet rays and are useful as, for example, a filler for cosmetics.

EXAMPLE 12

Ten parts by weight of the powder (P6) obtained in Example 6 and 100 parts by weight of polyester resin pellets were mixed and melt-kneaded to obtain a polyester composition having uniformly dispersed therein 5 wt % of zinc oxide fine particles. The composition was extruded into a sheet, and the extruded sheet was stretched to obtain a polyester film having a thickness of 50 pm. The film was a substantially transparent film in which the zinc oxide fine particles were uniformly and highly dispersed and which cut ultraviolet rays effectively.

In the same manner, a polyester composition containing 5 wt % of the zinc oxide fine particles was prepared and melt-spun to obtain polyester fiber. The resulting fiber had uniformly and highly dispersed therein the zinc oxide fine particles and cut ultraviolet rays effectively.

EXAMPLE 13

The dispersion (D5) obtained in Example 5 was subjected to centrifugation to remove the solvent. The resultant zinc oxide fine particles containing a slight amount of a residual solvent component were dispersed in ion-exchanged water, followed by centrifugation again. The above operation was repeated several times, and the finally obtained zinc oxide fine particles were dispersed in ion-exchanged water to give 50 parts by weight of an aqueous dispersion (D5-2) containing 20 wt % of the zinc oxide fine particles.

The aqueous dispersion (D5-2) was mixed with an acrylic resin emulsion (Acryset® ES-285E, produced by Nippon Shokubai Co., Ltd.) as a binder resin to prepare a coating composition. Polyester fiber was soaked in the coating composition and dried to obtain polyester fiber having the zinc oxide fine particles at an add-on of 0.5 g/m$^2$. The resulting fiber exhibited improved light resistance.

EXAMPLE 14

In a glass reactor equipped with a stirrer, a dropping opening, a thermometer, and a reflux condenser, 0.3 kg of commercially available zinc oxide powder was mixed with a mixed solvent of 1.5 kg of acetic acid and 1.5 kg of ion-exchanged water, followed by heating to 80° C. while stirring to dissolve the zinc oxide in the mixed solvent to obtain a uniform zinc-containing solution.

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 154° C. and maintained at that temperature. To the heated alcohol was added dropwise 3.3 kg of the zinc-containing solution kept at 80° C. over a 30-minute period by means of a constant delivery pump. With the dropwise addition, the temperature of the alcohol-based system decreased from 154° C. to 134° C. After the dropwise addition, the inner temperature was increased. When the temperature reached 167° C., 1.5 kg of a solution of 53 g of a methyl methacrylate-acrylic acid copolymer (methyl methacrylate/acrylic acid=9/1 by weight; weight average molecular weight: 7,500) in 2-butoxyethanol was added thereto and mixed. The temperature was further increased to 170° C., at which the mixture was maintained for 2 hours to obtain 10.65 kg of a dispersion of fine particles.

The fine particles were removed from the dispersing medium by centrifugation, washed with isopropyl alcohol, and dried in vacuo (10 Torr) at 50° C. for 24 hours to obtain powder P14 of the fine particles.

The powder P14 had a number average particle size of 2.0$\mu$ as measured from its scanning electron micrograph. Observation under a transmission electron microscope revealed that the powder P14 had a double layer structure in which zinc oxide fine particles having a particle size of 8 to 30 nm (number average particle size: 20 nm) were localized in the outer shell. The powder P14 was broken, and the broken particles were observed under a scanning electron microscope to find the fine particles hollow. The ZnO content in the powder P14 was found to be 87.7 wt %. The zinc oxide fine particles were confirmed to be ZnO crystals through X-ray diffractometry. The elementary analysis, FT-IR, etc. provided confirmation that the powder P14 contained the methyl methacrylate-acrylic acid copolymer. It was confirmed from all these results that the powder P14 was zinc oxide-polymer composite fine particles.

Figure 2:
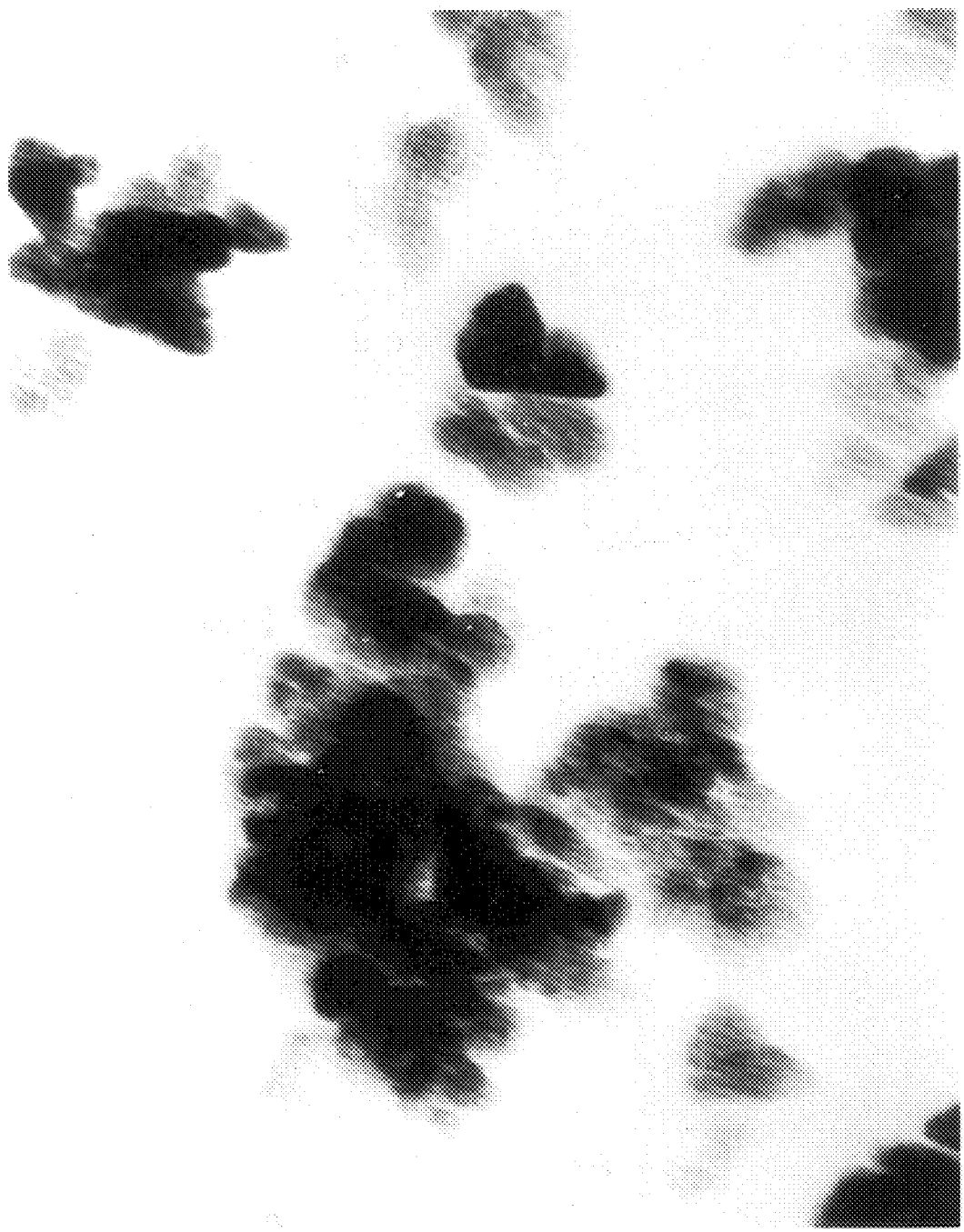
FIG. 2 is a transmission electron micrograph of zinc oxide fine particles in powder P14 obtained in Example 14.

The cross section of the fine particles obtained with a transmission electron microscope is shown in FIG. 1, and the transmission electron micrograph of the ZnO ultrafine particles present in the outer shell is shown in FIG. 2. The small black dots in FIG. 1 indicate zinc oxide fine particles. It is seen that a great number of the small black dots gather to form the outer shell of the lumpy composite fine particles. In FIG. 2, the line at the bottom right-hand corner of the picture is 20 nm long from end to end. In FIG. 2, the images of gray to black are zinc oxide fine particles. It is seen that a number of the zinc oxide fine particles are agglomerated.

The powder P14 was evaluated for gas adsorbing properties (deodorizing performance). The powder P14 weighing 1 g was put in a Tedlar bag, 3 l of air was introduced therein, and the bag was sealed. Then, trimethylamine was put in the bag, and the bag was allowed to stand at room temperature. The change in trimethylamine concentration in the bag was measured with time. The same test was carried out on methylmercaptan and propionic acid. The results obtained are shown below (gas concentration after a prescribed time period was relatively expressed taking the initial gas concentration as 100).

|  | 10 min | 1 hr | 3 hrs |
|---|---|---|---|
| Trimethylamine | 57 | 45 | 39 |
| Methylmercaptan | 52 | 25 | 18 |
| Propionic acid | 100 | 59 | 14 |

EXAMPLES 15 TO 18

Dispersions of zinc oxide-polymer composite fine particles were prepared in the same manner as in Example 14, except for replacing the methyl methacrylate-acrylic acid copolymer with the polymer shown in Table 4 below and altering the reaction conditions as shown in Table 4. Powders P15 to P18 of the composite fine particles were obtained from the resulting dispersions in the same manner as in Example 14. The physical properties of the polymers P14 to P5 are shown in Table 5 below.

TABLE 4

| | | Reaction Conditions | | | | | | |
|---|---|---|---|---|---|---|---|---|
| | Polymer Solution Added | | | | Zn-Monocarboxylic Acid Solution | | | |
| Example No. | Polymer | Amount of Polymer (kg) | Solvent | Reaction Solvent (kg) | Zinc Source (kg) | Mono-carboxylic Acid (kg) | Solvent (kg) | Solution Temp. (° C.) | Reaction Time & Temperature*[1] |
| 14 | methyl methacrylate-acrylic acid copolymer (MW: 7,500; COOH equiv.: 770) | 53 | 2-butoxy ethanol | 2-butoxy ethanol (12) | zinc oxide (0.3) | acetic acid (1.5) | water (1.5) | 80 | 170° C. 3 hrs |
| 15 | acrylic acid-hydroxyethyl methacrylate-styrene lauryl methacrylate copolymer (Mw: 20,000; COOH equiv.: 3000) | 92 | 2-butoxy ethanol | 2-butoxy ethanol (12) | zinc oxide (0.3) | acetic acid (1.5) | water (1.5) + methanol (1.5) | 60 | 170° C. 3 hrs |
| 16 | methyl methacrylate-methacrylamide copolymer (Mw: 5,000; amide equiv.: 500) | 40 | 2-butoxy ethanol | benzyl alcohol (5.5) + triethylene glycol (4.5) | zinc oxide. $2H_2O$ (0.81) | propionic acid (0.4) + acetic acid (1.0) | water (1.5) + methanol (3.0) | 40 | 200° C. 0.5 hr |
| 17 | polymethyl methacrylate (Mw: 120,000) | 20 | propylene glycol methyl ether acetate | 2-butoxy ethanol (12) | zinc oxide. $2H_2O$ (0.81) | acetic acid (1.5) | water (1.5) | 80 | 165° C. 1 hr |
| 18 | methyl methacrylate-methacryloxypropyltrimethoxysilane copolymer (Mw: 105,000) | 120 | cyclohexanol | cyclohexanol (10) + diethylene glycol (3) + dimethylformamide (2) | zinc oxide (0.3) | isobutyric acid (0.2) + acetic acid (1.0) | water (1.5) | 80 | 140° C. 1 hr |

Note:
*The time and temperature for/at which the system was maintained finally.

TABLE 5

Zinc Oxide-Polymer Composite Fine Particles

| Example No. | Powder Sample | Shape | Number Average Particle Size (μm) | Coefficient of Size Variation (%) | Inside Structure | Zinc Oxide Content (wet %) | Number Average Particle Size of ZnO Particles (nm) |
|---|---|---|---|---|---|---|---|
| 14 | P14 | spherical | 2.0 | 18 | double layer structure (ZnO localized in outer shell) | 87.8 | 20 |
| 15 | P15 | spherical | 1.4 | 4 | double layer structure (ZnO localized in outer shell) | 76.5 | 15 |
| 16 | P16 | spherical | 5.1 | 8 | double layer structure (ZnO localized in outer shell) | 85.7 | 150 |
| 17 | P17 | nearly spherical (ellipsoidal) | 2.0 | 22 | homogeneous structure (ZnO dispersed uniformly) | 93.0 | 80 |
| 18 | P18 | spherical | 0.45 | 14 | double layer structure (ZnO localized in outer shell) | 69.2 | 10 |

EXAMPLES 19 TO 21

Coating compositions (1) to (3) having the following formulation were prepared by using the powder P14 obtained in Example 14.

|  | Coating Composition (1) (Example 19) | Coating Composition (2) (Example 20) | Coating Composition (3) (Example 21) |
|---|---|---|---|
| Formulation (part by weight): |  |  |  |
| Powder P14 | 10 | 20 | 30 |
| Acrylic resin polymer solution* | 200 | 178 | 156 |
| Toluene | 250 | 222 | 194 |

*: Alloset 5247, produced by Nippon Shokubai Co., Ltd.; solid content: 45 wt %.

Each of the coating compositions (1) to (3) was applied to a glass plate and dried to obtain coated articles (1) to (3) having formed thereon a coating film whose thickness is shown below. The optical properties of the coated articles (1) to (3) are also shown below.

|  | Coated Article | Film Thickness (μm) | Total Transmission (%) | Haze (%) |
|---|---|---|---|---|
| Example 19 | (1) | 21 | 87 | 74 |
| Example 20 | (2) | 19 | 78 | 86 |
| Example 21 | (3) | 18 | 70 | 90 |
| Glass plate | — | none | 91 | 0.3 |

As is shown above, the coated articles of the invention have a greatly increased haze, which is indicative of light diffusion properties, over that of the glass plate substrate, while the total transmission of the coated articles is almost equal to or at least about 75% of that of the glass plate.

COMPARATIVE EXAMPLES 4 AND 5

Comparative coating compositions (1) and (2) were prepared in the same manner as in Example 19, except for replacing the powder P14 with ultrafine particles of ZnO having an average particle size of 0.02 μm (Comparative Example 4) or zinc oxide fine particles obtained by a French process (Aenka 1-Go Tokusei, a product of Sakai Chemical Industry Co., Ltd.). The coating compositions (1) and (2) were each applied to a glass plate and dried to obtain comparative coated articles (1) and (2), respectively, in the same manner as in Example 19. The optical properties of the comparative coated articles (1) and (2) are shown in the following table.

|  | Comparative Coated Article | Film Thickness (μm) | Total Transmission (%) | Haze (%) |
|---|---|---|---|---|
| Comparative Example 4 | (1) | 25 | 89 | 60 |
| Comparative Example 5 | (2) | 25 | 71 | 78 |

Comparing Examples 19 to 21 with Comparative Examples 4 to 5, it is apparent that the compositions containing the specific composite fine particles of the invention exhibit excellent light diffusion (diffuse transmission= total transmission×haze) while having a high percent transmission (total transmission) and that such excellent light diffusion properties are manifested even through the amount of the composite fine particles in the composition is small.

EXAMPLES 22 AND 23

A coating composition (4) was prepared by using the powder P14 obtained in Example 14 according to the following formulation.

Formulation of Coating Composition (4):

| Powder P14 | 10 parts by weight |
|---|---|
| Acrylic resin polymer solution (Alloset 5247, produced by Nippon Shokubai Co., Ltd.; | 200 parts by weight |

-continued

Formulation of Coating Composition (4):

solid content: 45 wt %
Toluene 250 parts by weight

The coating composition was applied to a polyester film or a methacrylic resin plate and dried to obtain a coated article (4) or (5), respectively. The optical properties of the resulting coated articles are shown in the following table.

| | Coated Article | Film Thickness (μm) | Total Transmission (%) | Haze (%) | UV-Screening Power |
|---|---|---|---|---|---|
| Example 22 | (4) | 5 | 88 | 20 | exhibited |
| Example 23 | (5) | 33 | 86 | 77 | exhibited |

EXAMPLE 24

Two parts by weight of the powder P17 obtained in Example 17 and 998 parts by weight of polycarbonate resin pellets were mixed and melt-kneaded to obtain a molten composition having uniformly dispersed therein 0.2 wt % of the fine particles. The composition was extruded into a plate having a thickness of 5.0 mm. The resulting polycarbonate plate had highly dispersed therein the composite fine particles and exhibited excellent visible light transmission, having a total transmission of 85% or more, and excellent ultraviolet screening effects.

EXAMPLE 25

Twenty-five parts by weight of the powder P14 obtained in Example 14 and 475 parts by weight of methacrylic resin pellets were mixed and melt-kneaded to obtain a molten composition having uniformly dispersed therein 5 wt % of the fine particles. The composition was extruded into a sheet having a thickness of 2 mm. The resulting methacrylic resin sheet had highly dispersed therein the fine particles and exhibited high visible light transmitting properties and excellent light diffusing properties, having a total transmission of 83% and a haze of 86%, and excellent ultraviolet screening effects.

COMPARATIVE EXAMPLE 6

A 2 mm thick methacrylic resin sheet containing 5 wt % of fine particles was obtained in the same manner as in Example 25, except for replacing the powder P14 with 25 parts by weight of zinc oxide fine particles obtained by a French process (Aenka 1-Go, a product of Sakai Chemical Industry Co., Ltd.). The resulting sheet contained the fine particles in a secondarily agglomerated and non-uniform state and was white turbid, lacking transparency.

EXAMPLE 26

Two parts by weight of the powder P15 obtained in Example 15 and 98 parts by weight of polyester resin pellets were mixed and melt-kneaded to obtain a polyester composition having uniformly dispersed therein 2 wt % of the composite fine particles. The composition was extruded into a sheet, and the extruded sheet was stretched to obtain a polyester film having a thickness of 40 μm. The film had uniformly and highly dispersed therein the fine particles and was excellent in visible light transmission, light diffusion, and ultraviolet screening.

COMPARATIVE EXAMPLE 7

A 40 μm thick polyester film containing 2 wt % of zinc oxide fine particles was obtained in the same manner as in Example 26, except for replacing the powder P15 obtained in Example 15 with zinc oxide fine particles obtained by a French process (Aenka 1-Go, a product of Sakai Chemical Industry Co., Ltd.). The resulting film contained the fine particles in a secondarily agglomerated state and therefore had a poor UV screening effect and was white turbid, lacking transparency.

The surface of the films obtained in Example 26 and Comparative Example 7 was observed under a transmission electron microscope. As a result, the surface of the film of Example 26 was found covered with uniform and fine projections because of the existence of fine particles, whereas the surface of the film of Comparative Example 7 was found to have poor quality due to non-uniform projections, including coarse projections resulting from agglomeration of fine particles.

EXAMPLE 27

A polyester composition containing 2 wt % of powder P17 was prepared in the same manner as in Example 26 except for replacing the powder 15 as used in Example 26 with powder P17 obtained in Example 17. The resulting polyester composition was melt-spun to obtain polyester fiber. The fiber had uniformly and highly dispersed therein the fine particles and exhibited transparency and an excellent UV screening effect.

COMPARATIVE EXAMPLE 8

Polyester fiber containing zinc oxide fine particles was obtained in the same manner as in Example 27 except for replacing the powder P17 with zinc oxide fine particles obtained by a French process (Aenka 1-Go, a product of Sakai Chemical Industry Co., Ltd.). The resulting fiber contained the fine particles in a secondarily agglomerated state and therefore had a low UV screening effect and was white turbid, lacking transparency.

EXAMPLE 28

The dispersion obtained in Example 17 was subjected to centrifugation to remove the solvent. The resultant composite fine particles containing a slight amount of the residual solvent component were dispersed in ion-exchanged water, followed by centrifugation again. The above operation was repeated several times, and the finally obtained particles were dispersed in ion-exchanged water to give 50 parts by weight of an aqueous dispersion containing 20 wt % of the fine particles.

Fifty parts by weight of the aqueous dispersion were mixed with 20 parts by weight of an acrylic resin emulsion (Acryset® ES-285E, produced by Nippon Shokubai Co., Ltd.; solids content: 50 wt %) as a binder to prepare a coating composition. Polyester fiber was soaked in the coating composition and dried to obtain polyester fiber having the fine particles at an add-on of 7.0 g/m². The resulting fiber exhibited excellent transparency and effectively cut ultraviolet light.

COMPARATIVE EXAMPLE 9

Ten parts by weight of zinc oxide fine particles obtained by a French process (Aenka 1-Go, a product of Sakai Chemical Industry Co., Ltd.) were mixed with 40 parts by weight of ion-exchanged water and dispersed by means of an ultrasonic homogenizer to give 50 parts by weight of an aqueous dispersion containing 20 wt % of the fine particles. Polyester fiber having an add-on of 6.8 g/m² of the fine particles was obtained by using the resulting aqueous dispersion in the same manner as in Example 28. The resulting fiber exhibited a UV-screening effect but was white turbid.

EXAMPLE 29

A cosmetic (O/W type cream) containing the powder P17 obtained in Example 17 was prepared according to the following formulation.

Formulation:
Aqueous Phase:

| (a) Powder | 6 parts by weight |
|---|---|
| (b) Propylene glycol | 5 parts by weight |
| (c) Glycerin | 10 parts by weight |
| (d) Potassium hydroxide | 0.2 part by weight |
| (e) Ion-exchanged water | 45 parts by weight |

Oily Phase:

| (f) Cetanol | 5 parts by weight |
|---|---|
| (g) Liquid paraffin | 5 parts by weight |
| (h) Stearic acid | 3 parts by weight |
| (i) Isostearyl myristate | 2 parts by weight |
| (j) Glycerol monostearate | 2 parts by weight |

The components (a) to (e) were mixed by stirring to prepare an aqueous phase, which was kept at 80° C. The components (f) to (j) were mixed uniformly to prepare an oily phase, which was kept at 80° C. The oily phase was added to the aqueous phase, followed by stirring. The mixture was emulsified by means of a homomixer, followed by cooling to room temperature to obtain cream. The resulting cream was clear and yet had a UV screening effect.

EXAMPLE 30

Cream was prepared in the same manner as in Example 29, except for replacing the powder P17 with the powder P14 obtained in Example 14.

The resulting cream had an excellent UV screening effect.

COMPARATIVE EXAMPLE 10

Cream was prepared in the same manner as in Example 29, except for replacing the powder P17 obtained in Example 17 with zinc oxide fine particles obtained by a French process (Aenka 1-Go, a product of Sakai Chemical Industry Co., Ltd.).

In the resulting cream the fine particles were dispersed poorly. Therefore, the cream had a rough feel and poor spreadability. Besides, it was nontransparent due to high whiteness.

EXAMPLE 31

The powder P15 obtained in Example 15 was mixed with ion-exchanged water to prepare an aqueous dispersion containing 10 wt % of the fine particles.

Separately, filter paper for quantitative determination (No. 5C, a product of Toyo Roshi K.K.) was beaten in a Niagara type beater into pulp having a C.S. freeness of 400 cc. The above prepared aqueous dispersion was added to the pulp to give a fine particle to pulp weight ratio of 1 wt %. The resulting pulp slurry was diluted to a solids content of 0.1 wt %, dehydrated in a TAPPI sheeting machine, and pressed to obtain a web having a basis weight of 75 g/m², which was then dried in a rotary drier at 100° C. to obtain paper containing 1 wt % of the fine particles. The resulting paper showed a satisfactory particle dispersed state and therefore exhibited excellent UV screening properties and had high surface flatness.

COMPARATIVE EXAMPLE 11

Paper was prepared in the same manner as in Example 31, except for replacing the powder P15 obtained in Example 15 with zinc oxide fine particles obtained by a French process (Aenka 1-Go, a product of Sakai Chemical Industry Co., Ltd.). The resulting paper contained the fine particles in secondarily agglomerated state and therefore had a poor UV screening effect. Further, the paper had poor surface conditions with coarse projections due to the agglomerated particles.

EXAMPLE 32

In a glass-made reactor equipped with a stirrer, a dropping opening, a thermometer, and a reflux condenser, 0.3 kg of commercially available zinc oxide powder was mixed with a mixed solvent of 1.5 kg of acetic acid and 1.5 kg of ion-exchanged water. The mixture was heated up to 80° C. while stirring to prepare a uniform zinc-containing solution (A32) comprising zinc oxide dissolved in the mixed solvent.

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 154° C. and maintained at that temperature. To the heated alcohol was added dropwise 3.3 kg of the zinc-containing solution (A32) kept at 80° C. over a 30-minute period by means of a constant delivery pump. The temperature of the alcohol-based system varied from 154° C. to 134° C. After the dropwise addition, the inner temperature was increased. When the temperature reached 167° C., 0.15 kg of a solution of 6.6 g of lactic acid in 2-butoxyethanol was added thereto and mixed. The temperature was further increased to 170° C., at which the mixture was maintained for 2 hours to obtain 10.0 kg of a dispersion (D32).

The fine particles contained in the dispersion (D32) had a weight average particle size of 2.0 μm as measured with a centrifugal precipitation type particle size distribution measuring apparatus.

The fine particles of the dispersion (D32) were separated from the dispersion medium by centrifugation, washed with methanol, and dried in vacuo (10 Torr) at 80° C. for 12 hours to obtain powder of the fine particles (P32).

The powder (P32) was made up of spherical fine particles having a number average particle size of 2.0 μm as measured from its scanning electron micrograph, with a coefficient of particle size variation of 3.4% and an L/B ratio of 1.06.

On performing calculation based on the weights of the dispersion (D32) and the powder (P32), the dispersion (D32) was found to be the one in which the individual particles of the powder (P32) were dispersed in a concentration of 3.1 wt % without undergoing secondary agglomeration.

The microstructure of the fine particles in the dispersion (D32) was analyzed under a scanning electron microscope and a transmission electron microscope. It was confirmed that the fine particles were clusters of thin plate crystals stacked one on another, each thin flat plate having an average thickness of 70 nm and an average major axis of 250 nm. It was also confirmed that the thin flat plates were zinc oxide crystals as a result of powder X-ray diffractometry of the fine particles and that the fine particles contained 96.0 wt % of zinc oxide (ZnO).

Figure 3:
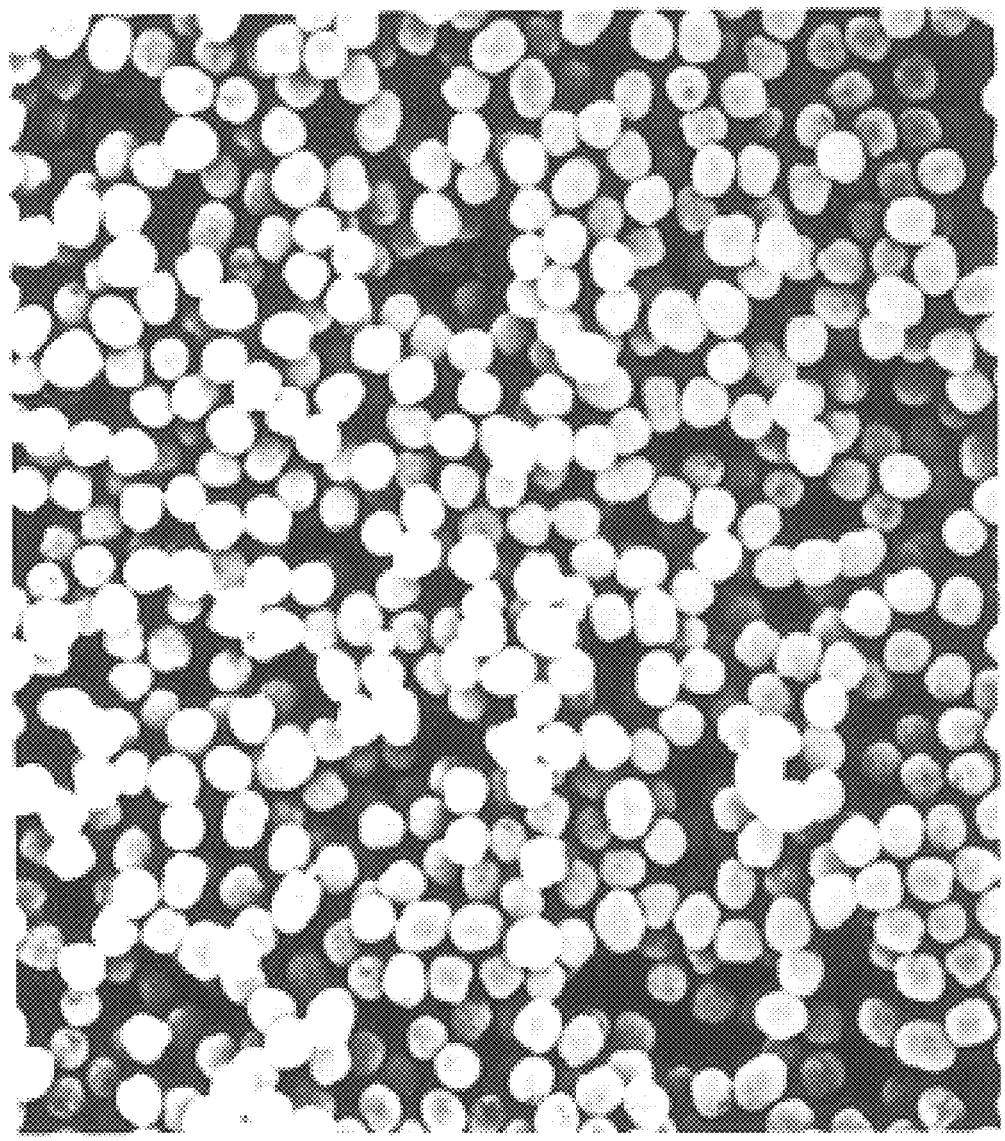
FIG. 3 is a scanning electron micrograph of powder (P32) obtained in Example 32.
Figure 4:
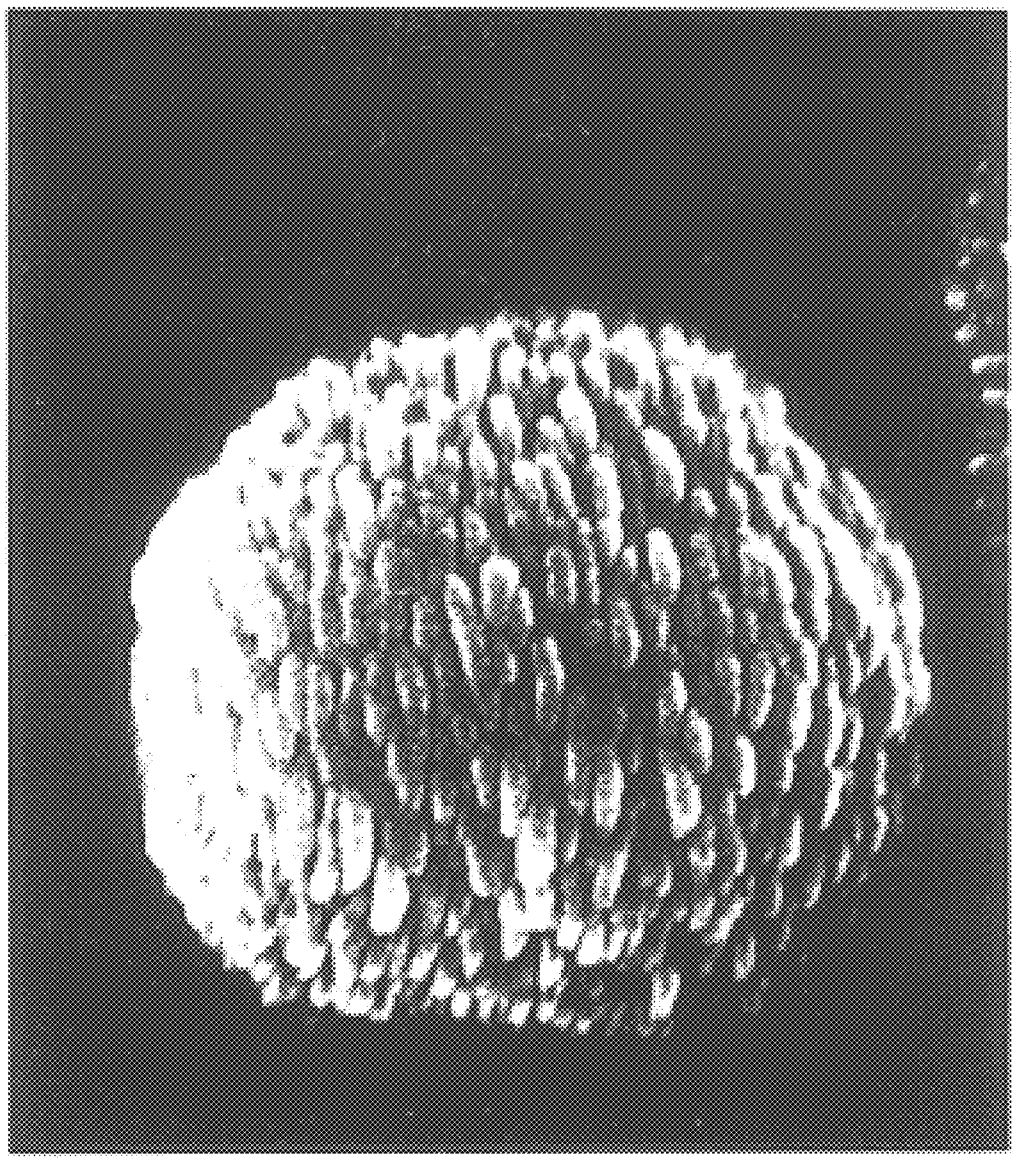
FIG. 4 is a scanning electron micrograph of fine particles in powder (P32) obtained in Example 32.
Figure 5:
FIG. 5 is a transmission electron micrograph of the cut section of the fine particles in powder (P32) obtained in Example 32.

The scanning electron micrograph of the fine particles in the powder (P32) and the transmission electron micrograph of the cut section of the fine particles are shown in Figures. FIG. 3 is a scanning electron micrograph of the powder (P32), in which the white to gray beads are fine particles of the powder (P32). FIG. 4 is a scanning electron micrograph of the individual fine particles in the powder (P32), in which the eleven white spots at the lower part of the picture were 860 nm long from end to end. In FIG. 4, the individual fine particles have on their surface a cluster of thin plates each having a rounded, long, and narrow shape. The cluster comprises thin plate like zinc oxide crystals. FIG. 5 is a transmission electron micrograph of the cut section of the individual fine particles in the powder (P32), in which the line at the bottom right-hand corner of the picture is 500 nm long from end to end. In FIG. 5, each fine particle has on its surface a cluster of thin plates with their end facing outward (the black sharp projections). The cluster have interstices among the individual thin plates. The individual fine particles are hollow, having almost no crystals in their inside.

It was confirmed that the individual fine particles were porous fine particles having a specific surface area of 16.9 m$^2$/g and a pore size of 4 nm.

The dispersion (D32) was heated at 120° C. under reduced pressure in an evaporator to evaporate part of the solvent. The thus concentrated dispersion was diluted with isopropyl alcohol to prepare a dispersion (D32a) containing 40 wt % of the fine particles.

The powder (P32) was evaluated for gas adsorbing properties (deodorizing performance). The powder (P32) weighing 1 g was put in a Tedlar bag, 3 l of air was introduced therein, and the bag was sealed. Then, trimethylamine was put in the bag, and the bag was allowed to stand at room temperature. The change in trimethylamine concentration in the bag was measured with time. The same test was carried out on methylmercaptan and propionic acid. The results obtained are shown below (gas concentration after a prescribed time period was relatively expressed taking the initial gas concentration as 100).

|  | 10 min | 1 hr | 3 hrs |
| --- | --- | --- | --- |
| Trimethylamine | 77 | 77 | 73 |
| Methylmercaptan | 85 | 38 | 25 |
| Propionic acid | 88 | 21 | 8 |

The antimicrobial activity of the powder (P32) was evaluated. A suspension of microbial cells of *E. coli* and *Staph. aureus* was inoculated to an agar plate medium containing the powder (P32) in a varied concentration and cultivated. The minimum concentration of the powder (in the agar medium) at which the growth of the bacteria were inhibited, i.e., minimum inhibition concentration (MIC), was obtained. The results are shown below.

|  | E. coli | Staph. aureaus |
| --- | --- | --- |
| MIC (μg/ml) | 3200 | 1600 |

The antimicrobial activity of zinc oxide powder prepared by a French process (Aenka 1-Go, a product of Sakai Chemical Industry Co., Ltd.; BET specific surface area: 2.9 m$^2$/g; average particle size: 0.52 μm) was examined in the same manner as described above. As a result, the MIC against *E. coli* was as high as 100000 μg/ml or more.

EXAMPLE 33

A dispersion of fine particles (D33) was obtained in the same manner as in Example 32, except for changing the amount of lactic acid added as shown in Table 6. The state of dispersion or agglomeration of the fine particles in the resulting dispersion and various physical properties of the dispersed fine particles are shown in Table 6.

Figure 6:
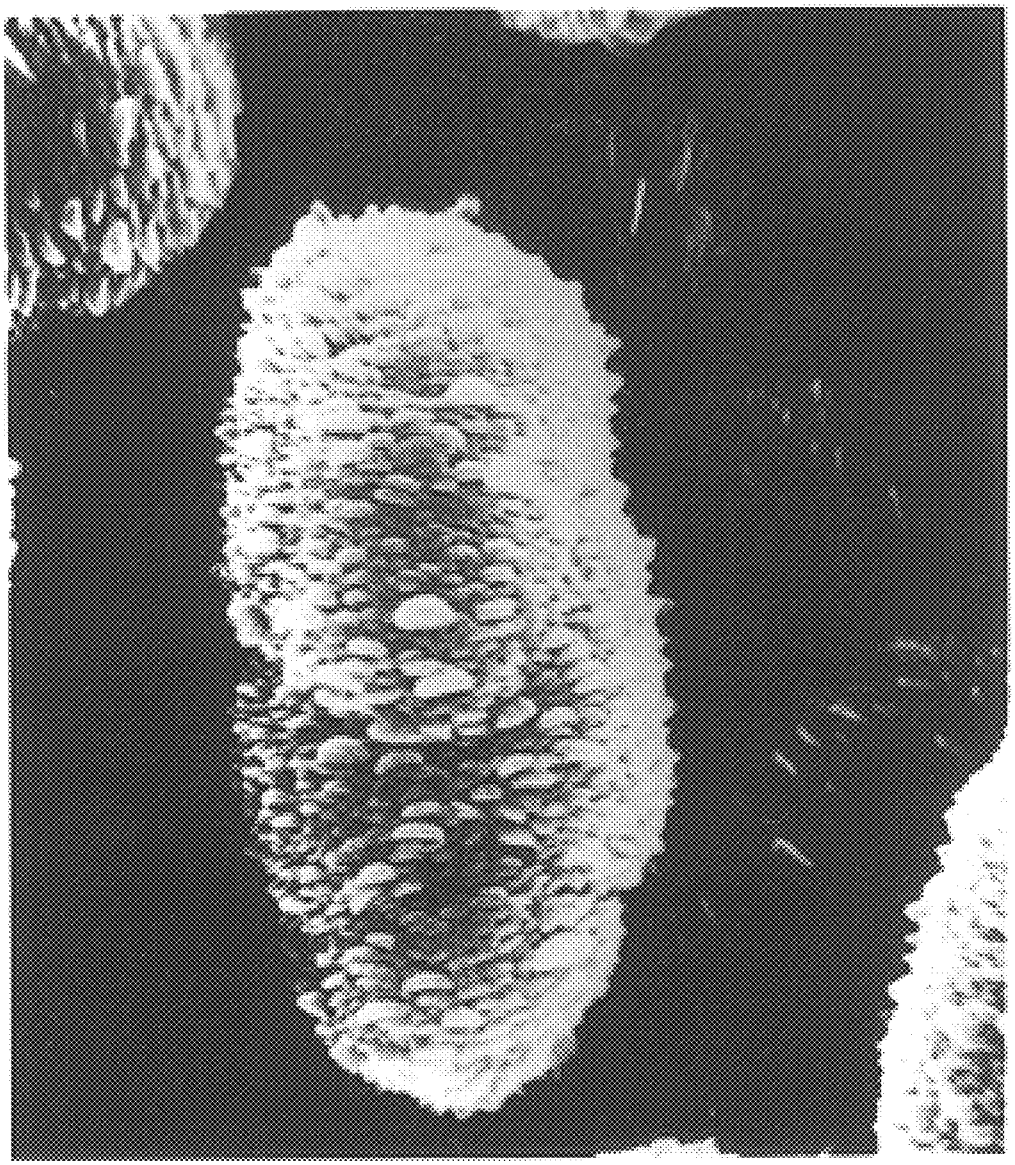
FIG. 6 is a scanning electron micrograph of fine particles in the powder obtained in Example 33.

The scanning electron micrograph of the fine particles in the powder obtained in Example 33 is shown in FIG. 6. The big and bright ellipse in the center of FIG. 6 is a single fine particle. In FIG. 6, the fine particle has on its surface a cluster of thin and rounded plates having a long and narrow shape or a fan shape. The cluster is made up of thin plates that are thin plate like zinc oxide crystals.

EXAMPLE 34

A dispersion of fine particles (D34) was prepared in the same manner as in Example 32, except for replacing zinc oxide as a zinc source with zinc acetate, using propionic acid in combination as a monocarboxylic acid, and changing the amount of lactic acid added as shown in Table 6. The state of dispersion or agglomeration of the fine particles in the dispersion (D34) and the physical properties of the fine particles are shown in Table 7.

EXAMPLE 35

In a glass-made reactor equipped with a stirrer, a dropping opening, a thermometer, and a reflux condenser, 0.3 kg of commercially available zinc oxide powder and 11.1 g of zinc lactate trihydrate were mixed with a mixed solvent of 1.5 kg of acetic acid and 1.5 kg of ion-exchanged water. The mixture was heated up to 80° C. while stirring to prepare a uniform zinc-containing solution (A35) comprising zinc oxide and zinc lactate dissolved in the mixed solvent.

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 160° C. and maintained at that temperature. To the heated alcohol was added dropwise the whole amount of the zinc-containing solution (A35) kept at 80° C. over a 30-minute period by means of a constant delivery pump. The temperature of the alcohol-based system dropped from 160° C. to 140° C. After the dropwise addition, the inner temperature was increased. When the temperature reached 170° C., the mixture was maintained at that temperature for 2 hours to obtain 9.1 kg of a dispersion (D35).

The state of dispersion or agglomeration of the fine particles in the dispersion (D35) and the physical properties of the fine particles are shown in Table 7.

EXAMPLE 36

A dispersion of fine particles (D36) was prepared in the same manner as in Example 35, except for changing the amounts of the raw materials used for the preparation of the zinc-containing solution as shown in Table 6. The state of dispersion or agglomeration of the fine particles in the dispersion (D36) and the physical properties of the fine particles are shown in Table 7.

EXAMPLE 37

A dispersion of fine particles (D37) was prepared in the same manner as in Example 35, except for changing the amounts of the raw materials used for the preparation of the zinc-containing solution as shown in Table 6. The state of dispersion or agglomeration of the fine particles in the dispersion (D37) and the physical properties of the fine particles are shown in Table 7.

The reaction conditions used in Examples 32 to 37 are shown in Table 6, and the physical properties of the fine particles obtained in Examples 32 to 37 are shown in Table 7.

TABLE 6

| | Reaction Conditions | | | | | | | | |
|---|---|---|---|---|---|---|---|---|---|
| | Zinc Source | | Monocarboxylic Acid | | Lactic Acid Source | | | | Reaction |
| Example No. | Kind | Amount (kg) | Kind | Amount (kg) | Kind | Amount (g) | Molar Ratio to Zinc | Stage of Addition | Temp. & Time* |
| 32 | zinc oxide | 0.3 | acetic acid | 1.5 | lactic acid | 6.6 | 2 | at the heating | 170° C. 2 hrs |
| 33 | zinc oxide | 0.3 | acetic acid | 1.5 | lactic acid | 1.7 | 0.5 | at the heating | 170° C. 0.5 hr |
| 34 | zinc acetate dihydrate | 0.81 | propionic acid acetic acid | 0.4 1.0 | lactic acid | 16.6 | 5 | at the heating | 170° C. 5 hrs |
| 35 | zinc oxide | 0.3 | acetic acid | 1.5 | zinc lactate trihydrate | 11.1 | 2 | at the prepn. of Zn-containing solution | 170° C., 1 hr |
| 36 | zinc acetate dihydrate | 1.00 | isobutyric acid acetic acid | 0.2 1.0 | zinc lactate trihydrate | 81.2 | 12 | at the prepn. of Zn-containing solution | 170° C. 10 hrs |
| 37 | zinc hydroxide | 0.37 | acetic acid | 1.5 | calcium lactate | 12.2 | 3 | at the prepn. of Zn-containing solution | 170° C. 1 hr |

Note:
*The time and temperature for/at which the system was maintained finally.

TABLE 7

Characteristics of Fine Particles

| Example No. | State of Dispersion or Agglomeration | Inorganic Compound Kind | Inorganic Compound Amount (wt %) | Shape | Number Average Particle Size (μm) | Coefficient of Size Variation (%) | L/B Ratio | Cluster of Thin plates Flatness | Cluster of Thin plates Major Axis (μm) |
|---|---|---|---|---|---|---|---|---|---|
| 32 | A | zinc oxide | 96.0 | spherical | 2.0 | 3.4 | 1.06 | 13 | 0.40 |
| 33 | A | zinc oxide | 97.9 | nearly spherical | 5.5 | 5.7 | 1.90 | 17 | 0.33 |
| 34 | B | zinc oxide | 92.8 | spherical | 1.4 | 9.3 | 1.08 | 6.7 | 0.15 |
| 35 | A | zinc oxide | 94.4 | spherical (spindle-shape) | 2.0 | 4.5 | 1.30 | 10 | 0.62 |
| 36 | C | zinc oxide | 80.1 | spherical | 2.4 | 18.0 | 1.04 | 105 | 0.84 |
| 37 | B | zinc oxide | 93.5 | spherical | 2.2 | 12.0 | 1.07 | 7.0 | 0.20 |

EXAMPLE 38

Methanol was added to the dispersion (D32a) obtained in Example 32 to prepare a slurry (S38) having a zinc oxide concentration of 10 wt %. The slurry (S38) was powdered in a vacuum flash evaporator illustrated below.

The vacuum flash evaporator had a jacketed stainless steel long pipe of 8 mm in inner diameter and 9 m in length. The long pipe was heated to 200° C. by circulating pressurized steam through the jacket. The slurry (S38) was continuously fed from one end of the long pipe (feed opening) at a flow rate of 10 kg/hr by a constant delivery pump. The other end of the long pipe was maintained at a reduced pressure of 50 Torr and connected to a back filter where powder is separated from the evaporated solvent. The powder (P38) of the zinc oxide fine particles thus separated was collected in a powder collecting chamber also kept at 50 Torr.

The resulting powder (P38) was easily dispersible in organic solvents, such as aromatic hydrocarbons (e.g., toluene), ketones (e.g., methyl ethyl ketone), esters (e.g., butyl acetate), and alcohols (e.g., methanol and isopropyl alcohol).

The resulting powder (P38) was substantially equal to the fine particles as dispersed in the dispersion (D32) in terms of particle size and shape, size and shape of the zinc oxide crystals, and the like.

EXAMPLE 39

A coating composition was prepared by using the dispersion (D32a) obtained in Example 32 according to the following formulation.

Formulation of Coating Composition:

| | |
|---|---|
| Dispersion (D32a) | 100 parts by weight |
| Toluene | 250 parts by weight |
| Alloset 5247 (aqueous acrylic resin emulsion produced by Nippon Shokubai Co., Ltd.; solid content: 45 wt %) | 4.5 parts by weight |

The coating composition was applied to each of a glass plate, a polyester film, and an acrylic resin plate and dried to form a coating film having a thickness of about 2 μm. The coating film on every substrate had a high diffuse transmission in the visible region and exhibited a heat ray screening effect as well as an excellent UV screening effect. Moreover, it assumed a pale pink or green color depending on the viewing angle or angle of light incidence, producing an extremely attractive appearance. The spectral transmission curves (a diffuse transmission curve and a vertical transmission curve) of the coated glass plate are shown in FIG. 7, in which $T_1$ is a diffuse transmission curve, $T_2$ a vertical transmission curve, and T3 a diffusion transmission curve of the uncoated glass plate.

COMPARATIVE EXAMPLE 12

A coating composition having a zinc oxide concentration of 10 wt % was prepared in the same manner as in Example 39, except for replacing the dispersion (D32a) with a dispersion of zinc oxide fine particles obtained by a French process (Aenka 1-Go, a product of Sakai Chemical Industry Co., Ltd.) in isopropyl alcohol, and the composition was applied to a glass plate to form a coating film having a thickness of 10 μm. The coating film was a white film having no characteristic in color. The spectral transmission curves (diffuse transmission curve $T_1$ and vertical transmission curve $T_2$) of the coated glass are shown in FIG. 8.

Figure 7:
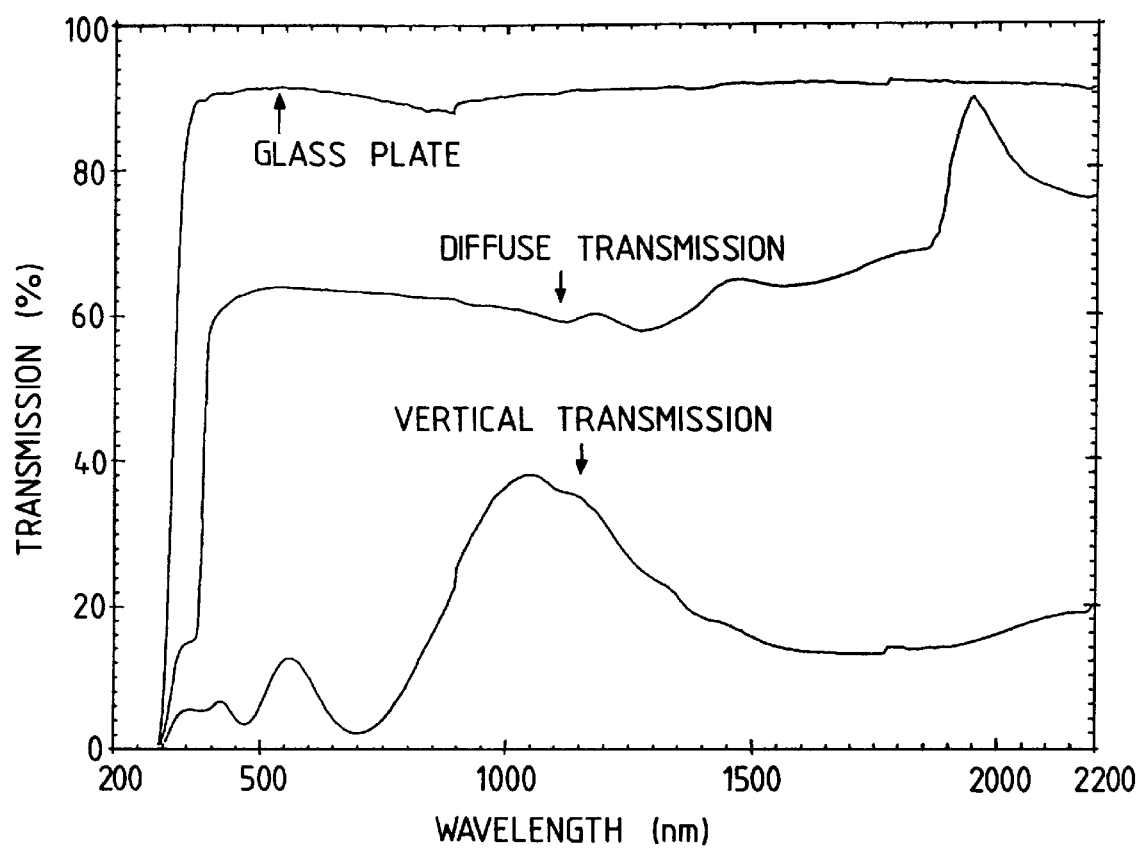
FIG. 7 shows spectral transmission curves of the coated article obtained in Example 39.
Figure 8:
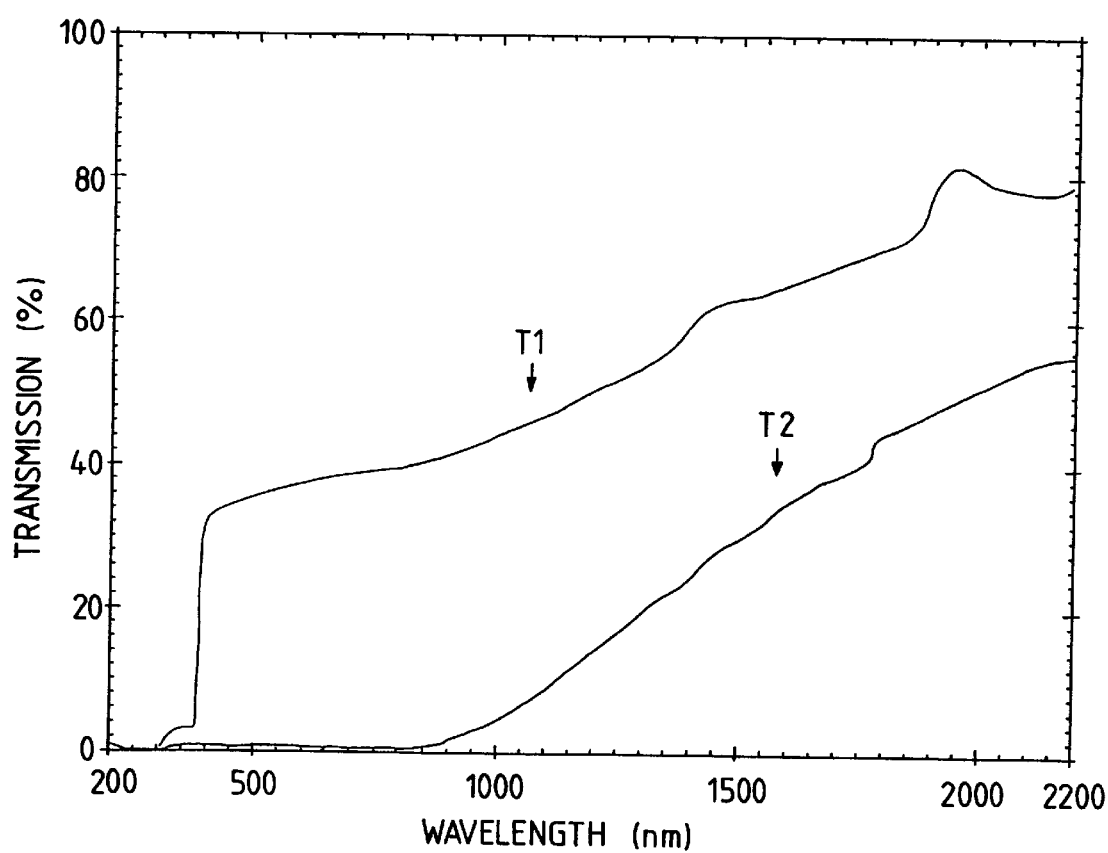
FIG. 8 shows spectral transmission curves of the coated article obtained in Comparative Example 12.

The comparison between FIGS. 7 and 8 proves that the coating film containing the fine particles obtained in Example 32 not only cuts ultraviolet light but screens out near infrared light without reducing the diffuse transmission in the visible region.

EXAMPLE 40

Fifteen parts by weight of the powder (P32) obtained in Example 32 and 485 parts by weight of polycarbonate resin pellets were mixed and melt-kneaded to obtain a molten composition having uniformly dispersed therein 3 wt % of the fine particles. The composition was extruded into a plate having a thickness of 1.5 mm. The resulting polycarbonate plate (A) was excellent in transparency, exhibited a UV screening effect and a heat ray screening effect, and presented an extremely attractive appearance, assuming a pale pink or green color depending on the viewing angle or angle of light incidence.

COMPARATIVE EXAMPLE 13

A 1.5 mm thick polycarbonate plate (B) containing 3 wt % of fine particles was prepared in the same manner as in Example 40, except for replacing the powder (P32) with 15 parts by weight of zinc oxide fine particles obtained by a French process (Aenka 1-Go, a product of Sakai Chemical Industry Co., Ltd.). The resulting polycarbonate plate was a white turbid plate with no characteristic in color.

EXAMPLE 41

Five parts by weight of the powder (P32) obtained in Example 32 and 95 parts by weight of polyester resin pellets were mixed and melt-kneaded to obtain a polyester composition having uniformly dispersed therein 5 wt % of the zinc oxide fine particles. The composition was extruded into a sheet, and the extruded sheet was stretched to obtain a polyester film having a thickness of 20 $\mu$m. The resulting film was a film having uniformly and highly dispersed therein the fine particles. The film was transparent, exhibited an excellent UV screening effect and a heat ray screening effect, and presented an attractive appearance, assuming a pale pink or green color depending on the viewing angle or angle of light incidence.

COMPARATIVE EXAMPLE 14

A polyester film containing zinc oxide fine particles was obtained in the same manner as in Example 41, except for replacing the powder (P32) obtained in Example 32 with zinc oxide fine particles obtained by a French process (Aenka 1-Go, a product of Sakai Chemical Industry Co., Ltd.). The resulting film had a UV screening effect but was white turbid.

Observation of the surface of the films obtained in Example 41 and Comparative Example 14 under a transmission electron microscope revealed that the surface of the film obtained in Example 41 was covered with uniform and fine projections due to the fine particles, whereas the surface of the film of Comparative Example 14 had a poor profile having irregular projections containing coarse projections due to the agglomerated particles.

EXAMPLE 42

A polyester composition containing 5 wt % of fine particles was prepared in the same manner as in Example 41. The resulting polyester composition was melt-spun to obtain polyester fiber. The fiber had dispersed therein the fine particles uniformly and finely and had a heat ray screening effect as well as transparency and an excellent UV screening effect. In addition, the fiber had an excellent appearance similarly to the film obtained in Example 41.

COMPARATIVE EXAMPLE 15

Polyester fiber containing zinc oxide fine particles was obtained in the same manner as in Example 42, except for replacing the powder obtained in Example 32 with zinc oxide fine particles obtained by a French process (Aenka 1-Go, a product of Sakai Chemical Industry Co., Ltd.). The resulting fiber had a UV screening effect but was white turbid.

EXAMPLE 43

The dispersion (D32a) prepared in Example 32 was subjected to centrifugation to remove the solvent. The resultant zinc oxide fine particles containing a slight amount of the residual solvent component were dispersed in ion-exchanged water, followed by centrifugation again. The above operation was repeated several times, and the finally obtained particles were dispersed in ion-exchanged water to obtain 50 parts by weight of an aqueous dispersion containing 20 wt % of the fine particles.

Fifty parts by weight of the aqueous dispersion were mixed with 20 parts by weight of an acrylic resin emulsion (Acryset® 285E, produced by Nippon Shokubai Co., Ltd.; solids content: 50 wt %) as a binder to prepare a coating composition. Polyester fiber was soaked in the coating composition and dried to obtain polyester fiber having the fine particles at an add-on of 7.0 g/m$^2$. The resulting fiber not only cut ultraviolet rays and heat rays effectively but presented an attractive appearance similarly to the film obtained in Example 41.

COMPARATIVE EXAMPLE 16

Ten parts by weight of zinc oxide fine particles obtained by a French process (Aenka 1-Go, a product of Sakai Chemical Industry Co., Ltd.) were mixed with 40 parts by weight of ion-exchanged water and dispersed by means of an ultrasonic homogenizer to give 50 parts by weight of an aqueous dispersion containing 20 wt % of the fine particles. Polyester fiber having an add-on of 6.8 g/m$^2$ of the fine particles was obtained by using the resulting aqueous dispersion in the same manner as in Example 43. The resulting fiber exhibited a UV-screening effect but was white turbid.

EXAMPLE 44

A cosmetic (O/W type cream) containing the powder (P32) obtained in Example 32 was prepared according to the following formulation.

Formulation:

Aqueous Phase:

| | |
|---|---|
| (a) Powder | 6 parts by weight |
| (b) Propylene glycol | 5 parts by weight |
| (c) Glycerin | 10 parts by weight |
| (d) Potassium hydroxide | 0.2 part by weight |
| (e) Ion-exchanged water | 45 parts by weight |

Oily Phase:

| | |
|---|---|
| (f) Cetanol | 5 parts by weight |
| (g) Liquid paraffin | 5 parts by weight |
| (h) Stearic acid | 3 parts by weight |
| (i) Isostearyl myristate | 2 parts by weight |
| (j) Glycerol monostearate | 2 parts by weight |

The components (a) to (c) were mixed by stirring to prepare an aqueous phase, which was kept at 80° C. The components (f) to (j) were mixed uniformly to prepare an oily phase, which was kept at 80° C. The oily phase was added to the aqueous phase, followed by stirring. The mixture was emulsified by means of a homomixer, followed by cooling to room temperature to obtain cream. The resulting cream was clear and assumed a pale pink color to produce an attractive appearance and also exhibited an excellent UV screening effect and a heat ray screening effect.

COMPARATIVE EXAMPLE 17

Cream was prepared in the same manner as in Example 44, except for replacing the powder obtained in Example 32 with zinc oxide fine particles obtained by a French process (Aenka 1-Go, a product of Sakai Chemical Industry Co., Ltd.).

The resulting cream had a UV screening effect but was opaque with a high degree of whiteness.

COMPARATIVE EXAMPLE 18

Cream was prepared in the same manner as in Example 44, except for replacing the powder obtained in Example 32 with thin plate like zinc oxide fine particles having an average particle size of 0.8 μm and an average thickness of 0.1 μm.

The resulting cream was slightly transparent and had a UV screening effect but was white in tone and had no attractive appearance.

EXAMPLE 45

The powder (P32) obtained in Example 32 was mixed with ion-exchanged water to prepare an aqueous dispersion containing 10 wt % of the fine particles.

Separately, filter paper for quantitative determination (No. 5C, a product of Toyo Roshi K.K.) was beaten in a Niagara type beater to pulp having a C.S. freeness of 400 cc. The above prepared aqueous dispersion was added to the pulp to give a fine particle to pulp weight ratio of 1 wt %. The resulting pulp slurry was diluted to a solids content of 0.1 wt %, dehydrated in a TAPPI sheeting machine, and pressed to obtain a web having a basis weight of 75 g/m$^2$, which was then dried in a rotary drier at 100° C. to obtain paper containing 1 wt % of the fine particles. The resulting paper presented an attractive appearance, assuming a pale pink or green color depending on the viewing angle or angle of light incidence, and also had a smooth surface.

COMPARATIVE EXAMPLE 19

Paper was prepared in the same manner as in Example 45, except for replacing the powder obtained in Example 32 with zinc oxide particles in the form of thin flat plate having an average particle size of 0.8 μm and an. average thickness of 0.1 μm. The resulting paper was white, presenting no beautiful appearance, and had a poor surface.

EXAMPLE I-1

In a 10 l glass-made reactor equipped with a stirrer, a dropping opening, a thermometer, and a reflux condenser, 0.3 kg of zinc oxide powder and 36.3 g of indium acetate dihydrate were mixed with a mixed solvent of 1.6 kg of acetic acid and 1.6 kg of ion-exchanged water. The mixture was heated up to 100° C. while stirring to prepare a uniform zinc-containing solution (AI-1).

In a 20 l glass-made reactor which was equipped with a stirrer, a dropping opening, a thermometer, and an outlet for distillate gas and could be heated by an external heating medium, 14 kg of 2-butoxyethanol was charged, and the inner temperature was raised up to 153° C. and maintained at that temperature. To the heated alcohol was added dropwise the whole amount of the zinc-containing solution (AI-1) kept at 100° C. over a 30-minute period by means of a constant delivery pump. The temperature of the alcohol-based system dropped from 153° C. to 131° C. After the dropwise addition, the inner temperature was increased. When the temperature reached 168° C., 400 g of a 2-butoxyethanol solution containing 36.9 g of lauric acid was added thereto over a period of 1 minute, and the mixture was maintained at that temperature for 5 hours to obtain 7.89 kg of a bluish gray dispersion (DI-1). The dispersion (DI-1) was a 3.5 wt % dispersion of thin and fine particles having an average particle size of 5 nm. The dispersed fine particles were X-ray crystallographically crystalline zinc oxide and had a metal oxide content of 94.5 wt % and contained indium at an atomic ratio of 3.0% to the total number of metallic atoms.

The physical properties of the resulting dispersion and the fine particles are shown in Table 10.

EXAMPLE I-2

A zinc-containing solution (AI-2) was prepared in the same manner as in Examine I-1, except for changing the kinds and amounts of the raw materials used in the zinc-containing solution (AI-1) of Example I-1 as shown in Table 8. Further, a dispersion (DI-2) was prepared in the same manner as in Example I-1, except for changing the amount of 2-butoxyethanol to 12 kg and using no lauric acid.

The physical properties of the resulting dispersion and the fine particles are shown in Table 10.

To 227 parts by weight of the dispersion (DI-2) obtained above was added 1 part by weight of octadecyltriethoxysilane, followed by stirring. The solvent was removed in an evaporator under reduced pressure at a bath temperature of 130° C., and the residue was further dried in vacuo at 100° C. to obtain 12 parts by weight of powder (PI-2-1).

EXAMPLE I-3

In the same 10 l glass-made reactor as used in Example I-1, equipped with a stirrer, a dropping opening, a thermometer, and a reflux condenser, 0.809 kg of zinc acetate dihydrate was mixed with a mixed solvent of 2.2 kg of acetic acid and 2.2 kg of ion-exchanged water. The mixture was heated up to 100° C. while stirring to prepare a uniform zinc-containing solution (AI-3).

In a 20 l glass-made reactor which was equipped with a stirrer, a dropping opening, a thermometer, and an outlet for distillate gas and could be heated by an external heating medium, 8 kg of 2-butoxyethanol and 5 kg of ethylene glycol n-butyl ether acetate were charged, and the inner temperature was increased to 162° C. and maintained at that temperature. To the heated alcohol solution was added dropwise the whole amount of the zinc-containing solution (AI-3) kept at 100° C. over a 30-minute period by means of a constant delivery pump. After the dropwise addition, the inner temperature was increased. When the temperature reached 168° C., a uniform solution of 90.8 g of aluminum tris(sec-butoxide) in 400 g of 2-butoxyethanol was added thereto all at once, and the mixture was maintained at 170° C. for 5 hours to obtain a dispersion (DI-3).

The physical properties of the resulting dispersion and the fine particles are shown in Table 10.

EXAMPLE I-4

A zinc-containing solution (AI-4) was prepared in the same manner as for the zinc-containing solution (AI-1) of Examine I-1, except for changing the kinds and amounts of the raw materials as shown in Table 8. Further, a dispersion (DI-4) was prepared in the same manner as in Example I-1, except for changing the amount of 2-butoxyethanol to 10.7 kg.

The physical properties of the resulting dispersion and the dispersed fine particles are shown in Table 10.

EXAMPLE I-5

In the same 10 l glass-made reactor as used in Example I-1, equipped with a stirrer, a dropping opening, a thermometer, and a reflux condenser, 0.30 kg of zinc oxide was mixed with a mixed solvent of 1.5 kg of acetic acid and 1.5 kg of ion-exchanged water. The mixture was heated up to 80° C. while stirring to prepare a uniform zinc-containing solution (AI-5).

In a 20 l glass-made reactor which was equipped with a stirrer, a dropping opening, a thermometer, and an outlet for distillate gas and could be heated by an external heating medium, 14 kg of 2-butoxyethanol and 60.6 g of ethylacetoacetatoaluminum diisopropylate were charged, and the inner temperature was raised up to 150° C. and maintained at that temperature. To the heated alcohol solution was added dropwise the whole amount of the zinc-containing solution (AI-5) kept at 80° C. over a 30-minute period by means of a constant delivery pump. After the dropwise addition, the inner temperature was increased to 170° C., at which the mixture was maintained for 5 hours to obtain a dispersion (DI-5).

The physical properties of the resulting dispersion and the fine particles are shown in Table 10.

The fine particles contained in the dispersion (DI-5) were separated from the dispersion medium by centrifugation, washed with methanol, and dried in vacuo (10 Torr) at 50° C. for 24 hours to obtain powder of the fine particles (PI-5).

The resulting powder (PI-5) had an average thickness of 0.025 $\mu$m, an average major axis of 0.08 $\mu$m, an L/B ratio of 2, a flatness of 3.2, a metal oxide content of 87.3 wt %, and an aluminum content of 5.5% in terms of atomic ratio to the total number of metallic atoms. The individual fine particle of the powder consisted of a stack of 2 to 5 thin plates (flakes) showing an X-ray diffraction pattern characteristic of crystalline zinc oxide.

COMPARATIVE EXAMPLE I-1

A dispersion of fine particles (DI-R1) was prepared in the same manner as in Example I-1, except that indium acetate was not used and the amount of 2-butoxyethanol was changed to 12.0 kg. The physical properties of the resulting dispersion and the fine particles are shown in Table 10.

EXAMPLE I-6

In a 10 l glass-made reactor equipped with a stirrer, a dropping opening, a thermometer, and a reflux condenser, 0.3 kg of zinc oxide powder and 36.3 g of indium acetate dihydrate were mixed with a mixed solvent of 1.6 kg of acetic acid and 1.6 kg of ion-exchanged water. The mixture was heated up to 100° C. while stirring to prepare a uniform zinc-containing solution (AI-6).

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 158° C. and maintained at that temperature. To the heated alcohol was added dropwise the whole amount of the zinc-containing solution (AI-6) kept at 100° C. over a 60-minute period by means of a constant delivery pump. After the dropwise addition, the inner temperature was increased. When the temperature reached 168° C., 500 g of a 2-butoxyethanol solution containing 300.0 g of an acrylic polymer (methyl methacrylate-hydroxyethyl methacrylate-maleic acid copolymer=8/1/1 by weight; weight average molecular weight: 4,500) was added thereto over a 1-minute period, and the mixture was maintained at 168° C. for 5 hours to obtain 9.80 kg of a bluish gray dispersion (DI-6).

The dispersion (DI-6) was a 3.1 wt % dispersion of fine particles having an average particle size of 20 nm. The dispersed fine particles were X-ray crystallographically crystalline zinc oxide, having a metal oxide content of 55 wt % and containing indium at an atomic ratio of 3.0% to the total number of metallic atoms. Observation under a transmission electron microscope provided confirmation that the individual fine particles were metal oxide particles coated with the acrylic polymer added.

The fine particles of the dispersion (DI-6) were separated from the dispersion medium by centrifugation, washed with isopropyl alcohol, and dried in vacuo (10 Torr) at 50° C. for 24 hours to obtain powder of the fine particles (PI-6).

It was confirmed that the fine particles of the powder (PI-6) were substantially equal to those in the dispersion.

The powder (PI-6) showed excellent dispersibility in organic solvents, such as alcohols (e.g., methanol, isopropyl alcohol, n-butanol, benzyl alcohol, and 2-ethoxyethanol); ketones (e.g., methyl ethyl ketone, methyl isobutylketone, and cyclohexanone), esters (e.g., butyl acetate and ethyl acetate), and aromatic hydrocarbons (e.g., benzene and toluene) and was easily re-dispersed in these solvents while retaining its single particle state.

EXAMPLE I-7

In a 10 l glass-made reactor equipped with a stirrer, a dropping opening, a thermometer, and a reflux condenser, 0.3 kg of zinc oxide powder and 36.3 g of indium acetate dihydrate were mixed with a mixed solvent of 1.6 kg of acetic acid and 1.6 kg of ion-exchanged water. The mixture was heated up to 100° C. while stirring to prepare a uniform zinc-containing solution (AI-7).

In a 20 l glass-made reactor which was equipped with a stirrer, a dropping opening, a thermometer, and an outlet for distillate gas and could be heated by an external heating medium, 12 kg of 2-butoxyethanol was charged, and the inner temperature was raised up to 158° C. and maintained at that temperature. To the heated alcohol was added dropwise the whole amount of the zinc-containing solution (AI-7) kept at 100° C. over a 30-minute period by means of a constant delivery pump. After the dropwise addition, the inner temperature was increased. When the temperature reached 168° C., 400 g of a 2-butoxyethanol solution containing 50.0 g of a methyl methacrylate-acrylic acid copolymer (9/1 by weight; weight average molecular weight: 7,200) was added thereto over several seconds, and the mixture was further maintained at 168° C. for an additional 5 hour period to obtain 11.79 kg of a bluish gray dispersion (DI-7). The dispersion (DI-7) was a 3.1 wt % dispersion of spherical fine particles having a metal oxide content of 86.0 wt %, an average particle size of 0.5 $\mu$m, and a hollow structure in which microcrystallites having a particle size of about 20 to 30 nm formed an outer shell of 0.2 $\mu$m in thickness.

The fine particles of the dispersion (DI-7) were separated from the dispersion medium by centrifugation, washed with isopropyl alcohol, and dried in vacuo (10 Torr) at 50° C. for 24 hours to obtain powder (PI-7) of the fine particles.

The resulting powder (PI-7) was spherical fine particles showing an X-ray diffraction pattern characteristic of crystalline zinc oxide, having an average particle size of 0.5 $\mu$m, and a metal oxide content of 86.0 wt %, and an indium content at an atomic ratio of 3.0% to the total number of metallic atoms. It was confirmed that the individual particles had a hollow structure made by localization of metal oxide fine particles having a diameter of about 25 nm and the methyl methacrylate-acrylic acid copolymer in the outer shell thereof. The diameter of the hollow portion was 0.1 $\mu$m in average. Observation under a scanning electron microscope provided confirmation that the surface of the fine particles had fine unevenness.

The powder (PI-7) had excellent dispersibility in organic solvents, such as alcohols (e.g., methanol, isopropyl alcohol, n-butanol, benzyl alcohol, and 2-ethoxyethanol); ketones (e.g., methyl ethyl ketone, methyl isobutylketone, and cyclohexanone), esters (e.g., butyl acetate and ethyl acetate), and aromatic hydrocarbons (e.g., benzene and toluene).

EXAMPLE I-8

Reaction was carried out in the same manner as in Example I-7, except for using 72.5 g of indium acetate dihydrate in place of 36.3 g of indium acetate dihydrate and using 800 g of a propylene glycol methyl ether acetate solution containing 30 g of polymethyl methacrylate (PMMA; weight average molecular weight: 60,000) in place of the 2-butoxyethanol solution of the methyl methacrylate-acrylic acid copolymer, to obtain 10.0 kg of a bluish gray dispersion (DI-8).

The fine particles of the dispersion (DI-8) were separated from the dispersion medium by centrifugation, washed with isopropyl alcohol, and dried in vacuo (10 Torr) at 50° C. for 24 hours to obtain powder (PI-8) of the fine particles.

The resulting powder (PI-8) was spherical fine particles showing an X-ray diffraction pattern characteristic of crystalline zinc oxide, having an average particle size of 3.0 $\mu$m, a metal oxide content of 90.1 wt % and containing indium at an atomic ratio of 5.8% to the total number of metallic atoms. It was confirmed that the individual particles comprised PMMA having uniformly dispersed therein granular metal oxide fine particles having a particle size of about 20 nm.

EXAMPLE I-9

Reaction was carried out in the same manner as in Example I-7, except for using 6.05 g of indium acetate dihydrate in place of 36.3 g of indium acetate dihydrate and using 200 g of a 2-butoxyethanol solution containing 7 g of lactic acid in place of the 2-butoxyethanol solution of the methyl methacrylate-acrylic acid copolymer, to obtain a bluish gray dispersion (DI-9).

The fine particles of the dispersion (DI-9) were separated from the dispersion medium by centrifugation, washed with methanol, and dried in vacuo (10 Torr) at 50° C. for 24 hours to obtain powder (I-9) of the fine particles.

The resulting powder (PI-9) was spherical fine particles showing an X-ray diffraction pattern characteristic of crystalline zinc oxide, having an average particle size of 1.2 $\mu$m, a metal oxide content of 96.0 wt % and containing indium at an atomic ratio of 0.5% to the total number of metallic atoms. The individual particles had a hollow structure in which the diameter of the hollow portion was 0.6 $\mu$m, and the outer shell consisted of densely stacked thin plates of metal oxide fine particles having a major axis of 0.3 $\mu$m and a flatness of 18.

Further, the powder (PI-9) had excellent dispersibility in polar solvents, such as water, alcohols (e.g., methanol, isopropyl alcohol, n-butanol, benzyl alcohol, and 2-ethoxyethanol); ketones (e.g., methyl ethyl ketone, methyl isobutylketone, and cyclohexanone), and esters (e.g., butyl acetate and ethyl acetate).

EXAMPLE I-10

A zinc-containing solution (AI-10) was prepared in the same manner as in Example I-1, except for changing the kinds and amounts of the raw materials used in the zinc-containing solution (AI-1) of Example I-1 as shown in Table 9. A dispersion (DI-10) was prepared from the zinc-containing solution (AI-10) in the same manner as in Example I-1, except for changing the amount of the 2-butoxyethanol to 12 kg and replacing lauric acid with 30.0 g of monoethanolamine.

The physical properties of the resulting dispersion and the fine particles of the dispersion are shown in Table 10.

TABLE 8

| | Zinc-Containing Solution | | | | Alcohol Solution | | Additive Solution | |
|---|---|---|---|---|---|---|---|---|
| Example No. | Zinc Source [Amount] (kg) | Monocarboxylic Acid [Amount] (kg) | Others [Amount] (kg) | Metal (M) Compound [Amount] (g) | Alcohol [Amount] (kg) | Metal (M) Compound [Amount] (g) | Metal (M) Compound [Amount] (g) | Others [Amount] (g) |
| I-1 | zinc oxide [0.30] | acetic acid [1.60] | water [1.60] | indium acetate dihydrate [36.3] | 2-butoxy-ethanol [14.0] | — | — | lauric acid [36.9] |
| I-2 | zinc oxide [0.285] basic zinc carbonate* [0.0203] | acetic acid [2.20] | water [2.20] | indium hydroxide (In$_2$O$_3$.5H$_2$O) [20.33] | 2-butoxy-ethanol [12.0] | — | — | — |
| I-3 | zinc acetate dihydrate [0.809] | acetic acid [2.20] | water [2.20] | — | 2-butoxy ethanol [8.0] ethylene glycol n-butyl ether acetate [5.0] | — | aluminum tris(sec-butyrate) [90.8] | — |
| I-4 | zinc oxide [0.30] | acetic acid [2.20] | water [1.60] | indium hydroxide (In$_2$O$_3$.5H$_2$O) [13.55] | 2-butoxy-ethanol [10.7] | — | — | lauric acid [36.9] |

TABLE 8-continued

| | Zinc-Containing Solution | | | | Alcohol Solution | | Additive Solution | |
|---|---|---|---|---|---|---|---|---|
| Example No. | Zinc Source [Amount] (kg) | Monocarboxylic Acid [Amount] (kg) | Others [Amount] (kg) | Metal (M) Compound [Amount] (g) | Alcohol [Amount] (kg) | Metal (M) Compound [Amount] (g) | Metal (M) Compound [Amount] (g) | Others [Amount] (g) |
| I-5 | zinc oxide [0.30] | acetic acid [1.50] | water [1.500] | — | 2-butoxy-ethanol [14.0] | ethyl-acetoacetato-aluminum diisopropylate [60.6] | — | — |

Note:
*ZnO content: 74.0 wt %

TABLE 9

| | Zinc-Containing Solution | | | | Alcohol Solution | | Additive Solution | |
|---|---|---|---|---|---|---|---|---|
| Example No. | Zinc Source [Amount] (kg) | Monocarboxylic Acid [Amount] (kg) | Others [Amount] (kg) | Metal (M) Compound [Amount] (g) | Alcohol [Amount] (kg) | Metal (M) Compound [Amount] (g) | Metal (M) Compound [Amount] (g) | Others [Amount] (g) |
| Comparative Example I-1 | zinc oxide [0.30] | acetic acid [1.60] | water [1.60] | — | 2-butoxy-ethanol [12.0] | — | — | lauric acid [36.9] |
| I-6 | zinc oxide [0.30] | acetic acid [1.60] | water [1.60] | indium acetate dihydrate [36.3] | 2-butoxy-ethanol [12.0] | — | — | methyl methacrylate-hydroxyethyl methacrylate-maleic acid copolymer [300.0] |
| I-7 | zinc oxide [0.30] | acetic acid [1.60] | water [1.60] | indium acetate dihydrate [36.3] | 2-butoxy-ethanol [12.0] | — | — | methyl methacrylate-acrylic acid copolymer [50.0] |
| I-8 | zinc oxide [0.30] | acetic acid [1.60] | water [1.60] | indium acetate dihydrate [72.5] | 2-butoxy ethanol [12.0] | — | — | polymethyl methacrylate [30.0] |
| I-9 | zinc oxide [0.30] | acetic acid [1.60] | water [1.60] | indium acetate dihydrate [6.05] | 2-butoxy-ethanol [12.0] | — | — | lactic acid [7] |
| I-10 | zinc oxide [0.30] | acetic acid [2.20] | water [2.20] | indium hydroxide ($In_2O_3 \cdot 5H_2O$) [5.42] | 2-butoxy-ethanol [12.0] | — | — | monoethanol-amine [30.0] |

TABLE 10

| Example No. | Dispersion No. | Concn. of Particles in Dispersion (wt %*) | Metal Oxide Content (wt %) | Metal (M)/ Total Metal (atom %) | Particle Shape | Average Particle Size ($\mu$m) | X-ray Diffraction Pattern | UV Cutting Power | Heat Ray Cutting Power | Electric conductivity | Visible Light Transmission (Transparency) |
|---|---|---|---|---|---|---|---|---|---|---|---|
| I-1 | Di-1 | 3.5 | 94.5 | 3.0 | thin plate | 0.005 | ZnO crystal | A | +++ | +++ | +++ |
| I-2 | Di-2 | 4.4 | 95.8 | 2.9 | granular | 0.01 | ZnO crystal | A | +++ | +++ | +++ |
| I-3 | Di-3 | 5.5 | 92.0 | 9.2 | granular | 0.21 | ZnO crystal | B | ++ | ++ | ++ |
| I-4 | Di-4 | 5.0 | 95.0 | 2.0 | granular | 0.01 | ZnO crystal | A | +++ | ++ | +++ |
| I-5 | Di-5 | 3.6 | 87.3 | 5.5 | thin plate | 0.08(1) 0.025(t) | ZnO crystal | A | ++ | + | ++ |
| I-6 | Di-6 | 3.1 | 55.0 | 3.0 | granular | 0.02 | ZnO crystal | A | +++ | ++ | +++ |
| Comparative I-1 | Di-R1 | 3.7 | 94.8 | 0 | granule | 0.02 | ZnO crystal | A | + | − | +++ |
| I-7 | Di-7 | 3.1 | 86.0 | 3..0 | granular | 0.50 | ZnO crystal | B | +++ | ++ | + |
| I-8 | Di-8 | 3.3 | 90.1 | 5.8 | granular | 3.0 | ZnO crystal | B | +++ | ++ | + |
| I-9 | Di-9 | 5.8 | 96.0 | 0.5 | granular | 1.2 | ZnO crystal | B | ++ | ++ | + |
| I-10 | Di-10 | 3.2 | 87.0 | 0.8 | granular | 0.003 | ZnO crystal | A | ++ | +++ | ++ |

Note:
*Concentration as converted to metal oxides

The dispersions (DI-1) and (DI-R1) obtained in Example I-1 and Comparative Example I-1 were each concentrated in an evaporator under reduced pressure at a bath temperature of 130° C. to have a particle concentration of 10 wt % to prepare a concentrated dispersion (DI-1C) and (DI-RC), respectively. To 100 parts by weight of the concentrated dispersion was added 1.11 part by weight of an acrylic resin solution (Alloset 5210 produced by Nippon Shokubai Co., Ltd.; solids content: 45 wt %), followed by stirring for 2 hours to prepare a coating composition.

Each coating composition was applied by spin coating to a Pyrex glass plate having thereon a comb type electrode made of gold by vacuum evaporation, dried at room temperature, and heated at 50° C. to provide a dry film (DI-1M) or (DI-RM). Each coating film was a homogeneous film having a thickness of 1.0 $\mu$m.

After the dried film was allowed to stand at 20° C. and 60% RH for 1 hour with light shielded, the surface resistivity of the film was measured under the above environmental conditions with Electrometer 617 (produced by Kesley Corp.). The results were as follows.

| | |
|---|---|
| DI-1M | $2.7 \times 10^{11}$ $\Omega$ per square |
| DI-RM | $3.9 \times 10^{14}$ $\Omega$ per square |

The surface resistivity of the film Di-1M was also measured after it was allowed to stand at 20° C. and at the relative humidity shown below for 1 hour with light shielded. The results were as follows.

| Relative Humidity | Surface Resistivity ($\Omega$ per square) |
|---|---|
| 20% | $1.9 \times 10^{11}$ |
| 60% | $2.7 \times 10^{11}$ |
| 85% | $2.8 \times 10^{11}$ |

Coating compositions were prepared using the dispersions (DI-2) to (DI-5) obtained in Examples I-2 to I-5 and applied to a glass plate to form a coating film having a thickness of 1 $\mu$m in the same manner as described above. The surface resistivity of the resulting film was measured at 20° C. and 60% RH. As a result, the surface resistivity (unit: $\Omega$ per square) of every coating film was on the order of $10^{11}$ or $10^{12}$. It was also confirmed that the surface resistivity was constant irrespective of humidity similarly to the case of Example I-1.

These results provide confirmation that the fine particles of the dispersions obtained in Examples I-1 to I-5 were more conductive than conventional zinc oxide particles. It was also confirmed that the conductivity of these particles was independent on humidity. Therefore, the fine particles (or dispersions) obtained by the invention are suitable materials of an antistatic film.

Figure 10:
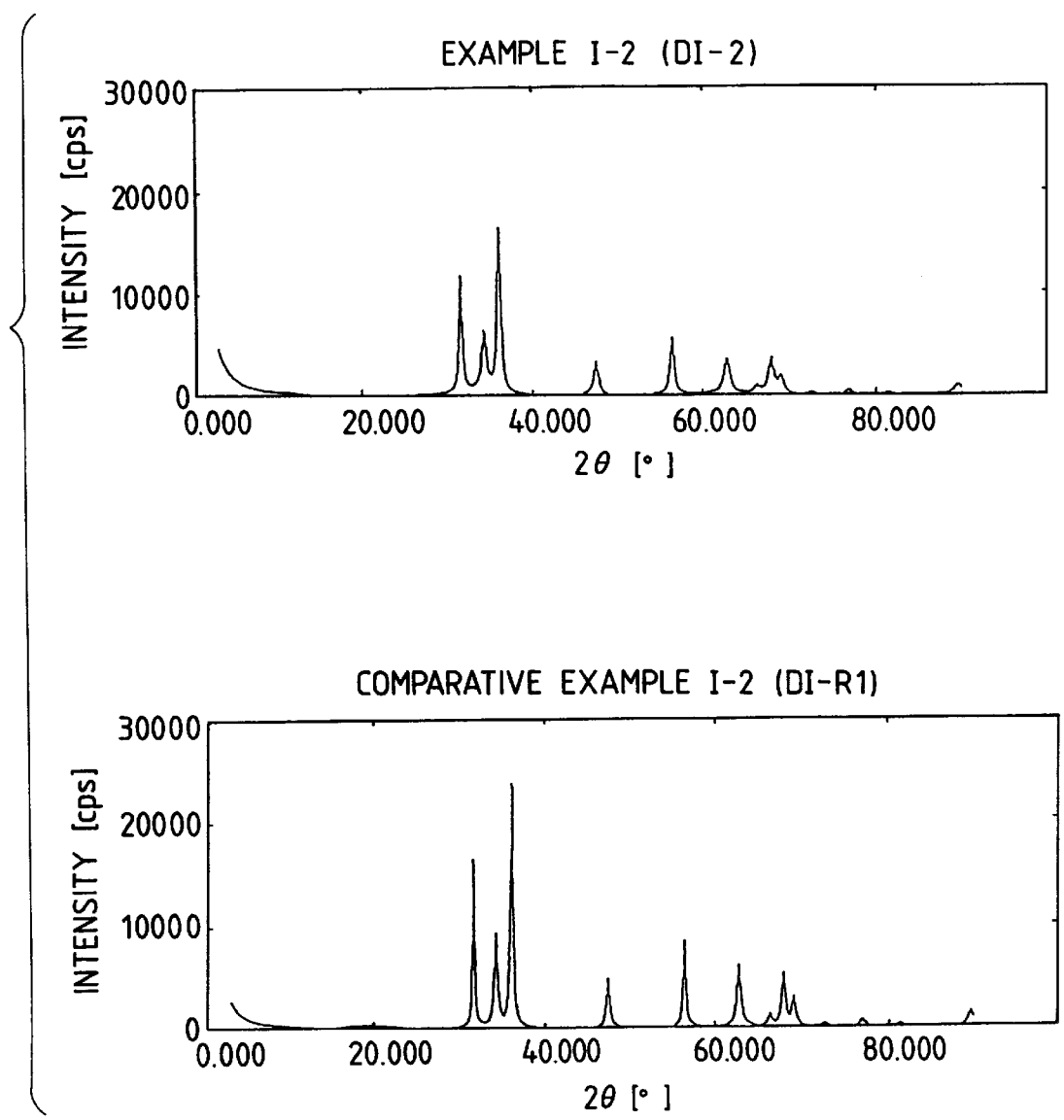
FIG. 10 shows X-ray diffraction patterns of powders.

Powder samples were obtained from the dispersions (DI-2) and (DI-R1) obtained in Example I-2 and Comparative Example I-1 in the same manner as described above. The results of powder X-ray diffractometry on the resulting powder samples are shown in FIG. 10, in which the abscissa indicates a diffraction angle (2θ; °), and the ordinate the intensity (cps). As is shown in FIG. 10, it can be seen that both Di-2 and Di-R1 show sharp peaks assigned to ZnO.

COMPARATIVE EXAMPLE I-2

In 500 g of ion-exchanged water was dissolved 35.0 g of ammonium bicarbonate to prepare a solution A.

In ion-exchanged water was dissolved 6.1778 g of aluminum sulfate hydrate ($Al_2(SO_4)_3.nH_2O$: n=14 to 18) to prepare a solution B.

A hundred grams of zinc oxide prepared by a French process (Aenka 1-Go, a product of Sakai Chemical Industry Co., Ltd.) were added to 180 g of ion-exchanged water to obtain a slurry C.

Further, 1.00 g of silica fine powder (Aerosil 200, produced by Nippon Aerosil K.K.) was added to 50 g of ion-exchanged water, followed by stirring to prepare a dispersion D.

The solution B was added to the solution A while stirring at room temperature, whereupon the mixture became an emulsion. The stirring of the emulsion was continued for 10 minutes.

In a 1 l glass-made reactor which was equipped with a stirrer, a dropping opening, a thermometer, and a reflux condenser and could be heated by an external heating medium, the slurry C was charged, and the above-prepared emulsion was added thereto through the dropping opening while stirring at room temperature. The heating medium temperature was set at 80° C., and heating was started. About 30 minutes later when the inner temperature reached 61° C., the dispersion D was added, followed by stirring for 1 hour under heating. One hour later, when the inner temperature reached 76.6° C., heating was stopped, and the system was allowed to cool while continuing stirring. When the inner temperature dropped to room temperature, the whole amount of the slurry was subjected to vacuum filtration. The thus separated fine particles were thoroughly washed with ion-exchanged water, dried in vacuo at 50° C. for 12 hours and then dried in vacuo at 100° C. for 4 hours to give white powder.

Figure 11:
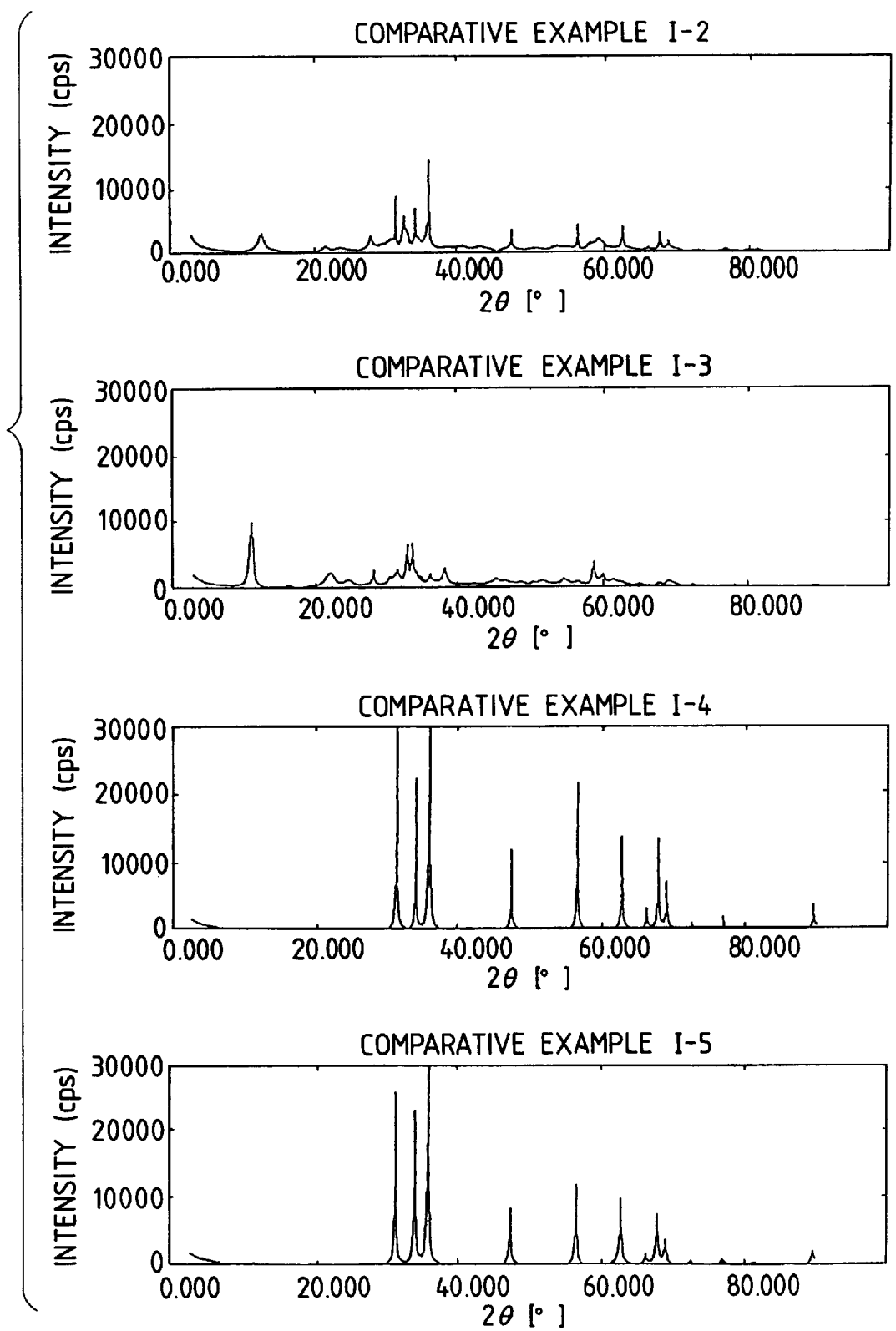
FIG. 11 shows X-ray diffraction patterns of powders.

The X-ray diffraction pattern of the resulting white powder showed not only the diffraction peaks assigned to ZnO but also peaks assigned to impurity, which was ascribable to basic zinc carbonate $Zn_4CO_3(OH)_6.H_2O$. It was thus confirmed that ZnO had low crystalline properties. The X-ray diffraction pattern of the powder is shown in FIG. 11.

COMPARATIVE EXAMPLE I-3

In 50 g of ion-exchanged water were dissolved 8.3753 g of zinc chloride ($ZnCl_2$) and 0.3167 g of aluminum chloride ($AlCl_3.6H_2O$) to obtain a uniform solution. A 14 wt % ammonia aqueous solution was added dropwise to the solution while stirring at room temperature. The dropwise addition was stopped when the pH of the system reached 8.21. The amount of the 14 wt % aqueous ammonia added was 20.0 g.

After the dropwise addition, the mixture was stirred for 10 minutes, followed by filtration. The filter cake was thoroughly washed with water, followed by centrifugation to recover the fine particles. The particles were vacuum dried at 50° C. for 12 hours and then dried in vacuo at 100° C. for 4 hours to furnish white powder.

The X-ray diffraction pattern of the resulting white powder showed no peak assigned to ZnO. The X-ray diffraction pattern of the powder is shown in FIG. 11.

COMPARATIVE EXAMPLE I-4

White powder was prepared in the same manner as in Comparative Example I-2. The resulting white powder was put in a calcining furnace and heated from room temperature to 640° C., kept at this temperature for 1 hour in a nitrogen atmosphere, and cooled to room temperature to give grayish white powder.

It was confirmed by X-ray diffractometry that the resulting powder was ZnO crystals. The X-ray diffraction pattern of the powder is shown in FIG. 11.

Figure 12:
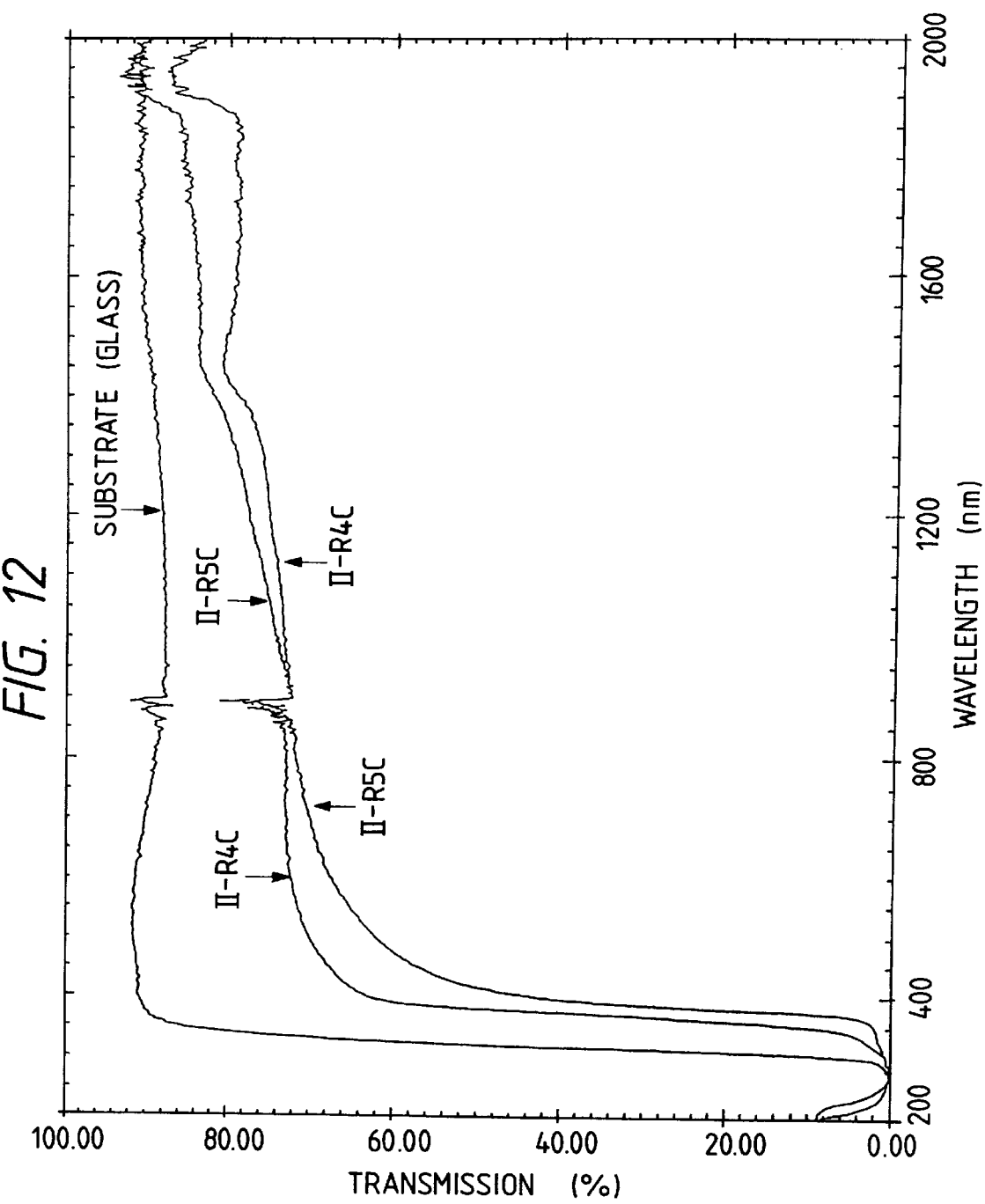
FIG. 12 shows spectral transmission curves of a coated article.

The powder was formulated into a coating composition of the following composition, and the coating composition was applied to a glass plate substrate to obtain a coated article (II-R4C) having a 3.1 μm thick coating film. The resulting coated article (II-R4C) was white turbid and had low transparency to visible light, having a haze as high as 78%. It exhibited UV screening properties but no heat ray screening properties. The spectral transmission curve of the coated article (II-R4C) is shown in FIG. 12.

Formulation of Coating Composition:

| Powder | 10 parts by weight |
|---|---|
| 2-Butoxyethanol | 90 parts by weight |
| Acrylic resin solution* | 50 parts by weight |

*Alloset 5247 (produced by Nippon Shokubai Co., Ltd.; solid content: 45 wt %) was diluted with toluene to a solids content of 20 wt %.

Preparation of Coating Composition:

The powder was added to 2-butoxyethanol and dispersed in an ultrasonic homogenizer for 20 minutes. The acrylic resin solution was added thereto, followed by stirring for 2 hours. The mixture was further dispersed in an ultrasonic homogenizer for 20 minutes to obtain a coating composition.

COMPARATIVE EXAMPLE I-5

White powder was obtained in the same manner as in Comparative Example I-3. The powder was heated from room temperature to 640° C. in a nitrogen atmosphere in a calcining furnace, maintained at 640° C. for 1 hour, and cooled to room temperature to obtain slightly greenish gray-tinted powder.

As a result of X-ray diffractometry, it was confirmed that the resulting powder was ZnO crystals. The X-ray diffraction pattern of the powder is shown in FIG. 11, in which the abscissa indicates a diffraction angle (2θ; °), and the ordinate the intensity (cps).

The powder was formulated into a coating composition in the same manner as in Comparative Example I-4, and the coating composition was applied to a glass plate to obtain a coated article (II-R5C) having a 3.2 μm thick film. The coated article (II-R5C) was white turbid and had low transparency to visible light, having a haze as high as 83%. It exhibited UV screening properties but no heat ray screening properties. The spectral transmission curve of the coated article (II-R5C) is shown in FIG. 12.

EXAMPLE II-1

The dispersion (DI-1) obtained in Example I-1 was concentrated in an evaporator under reduced pressure at a bath temperature of 130° C. to have a particle concentration of 10 wt % to prepare a concentrated dispersion (DI-1C).

An acrylic resin solution (Alloset 5210 produced by Nippon Shokubai Co., Ltd.; solids content: 45 wt %) was diluted with toluene to a resin concentration of 20 wt %. To 50 parts by weight of the diluted resin solution was added 100 parts by weight of the concentrated dispersion (DI-1C), followed by stirring to prepare 150 parts by weight of a coating composition (II-1).

EXAMPLE II-2

The dispersion (DI-2) obtained in Example I-2 was concentrated in an evaporator under reduced pressure at a bath temperature of 130° C. to have a particle concentration of 10 wt % to prepare a concentrated dispersion (DI-2C).

The concentrated dispersion (DI-2C) was separated by centrifugation into a precipitate of the fine particles and the solvent (supernatant liquid). The precipitate was added to ion-exchanged water and dispersed in a sand mill to obtain an aqueous dispersion (DI-2W) having finely dispersed therein 10 wt % of the fine particles.

To 100 parts by weight of an aqueous solution containing 10 wt % of a vinyl resin (Poval R2105, produced by Kuraray Co., Ltd.) was added 100 parts by weight of the aqueous dispersion (DI-2W), followed by stirring to obtain a coating composition (II-2) containing 5 wt % of the fine particles and 5 wt % of the binder.

monohydrate was further added thereto, followed by stirring. Ultrasonication of the mixture gave a coating composition (II-4).

The coating compositions (II-1) to (II-4) obtained in Examples II-1 to II-4 were applied to various substrates with a bar coater and dried to obtain coated articles (II-1C1), (II-1C2), (II-2C), (II-3C), and (II-4C), respectively.

The film formation conditions, the thickness of the coating film, and the optical characteristics of the coated articles are shown in Table 11 below.

TABLE 11

| | Film Forming Conditions | | | | Physical and Optical Properties of Coated Article | | | | | |
|---|---|---|---|---|---|---|---|---|---|---|
| Coated Article | Coating Composition | Substrate | Coating Method | Drying Conditions | Film Thickness ($\mu$m) | Heat Ray Cut (2 $\mu$m) (%) | UV Cutting Power (Transmission) | Transmission (600 nm) (%) | Total Transmission (%) | Haze (%) |
| II-1C1 | II-1 | glass | bar coater | 80° C., 30 min | 1.2 | 17 | B (6%) | 85 | 87 | 20 |
| II-1C2 | II-1 | glass | bar coater | 80° C., 30 min | 5.5 | 54 | A (0%) | 73 | 76 | 35 |
| II-2C | II-2 | acrylic resin plate | bar coater | 100° C., 30 min | 3.7 | 55 | A (0%) | 83 | 84 | 9 |
| II-3C | II-3 | PC plate | bar coater | 200° C., 30 min | 0.8 | 42 | B (2%) | 78 | 80 | 29 |
| II-4C | II-4 | PET film | bar coater | 110° C., 5 min | 1.2 | 30 | A (1%) | 84 | 85 | 13 |

EXAMPLE II-3

The dispersion (DI-1) obtained in Example I-1 was concentrated in an evaporator under reduced pressure at a bath temperature of 130° C. to have a particle concentration of 10 wt % to prepare a concentrated dispersion (DI-1C).

In a 4-necked flask equipped with a reflux condenser, a stirrer, and a thermometer were charged successively 24 parts by weight of isopropyl alcohol, 16 parts by weight of water, and 0.005 part by weight of 35% hydrochloric acid. To the mixture were further added 10 parts by weight of methyltrimethoxysilane and 30 parts by weight of tetraethoxysilane while stirring, and the mixture was heated at 80° C. for 2 hours, followed by cooling. The resulting mixture (x) was a uniform solution having a non-volatile content of 17.0 wt %.

Twelve parts by weight of the mixture (x) were added to 80 parts by weight of the concentrated dispersion (DI-1C) while stirring to prepare a coating composition (II-3).

EXAMPLE II-4

In the same manner as in Example II-2, an aqueous dispersion (DI-2W) having finely dispersed therein 10 wt % of fine particles was prepared from the dispersion (DI-2) obtained in Example I-2.

To 20 parts by weight of an aqueous solution containing 10 wt % of a vinyl resin (Poval 205, produced by Kuraray Co., Ltd.) was added 100 parts by weight of the aqueous dispersion (DI-2W), and 20 parts by weight of an aqueous solution containing 1.23 part by weight of copper acetate The coating film of every coated article was homogeneous and screened out ultraviolet rays and heat rays while having excellent transparency to visible light.

The sunlight transmission and visible light transmission of the coated articles (II-1C1) and (II-1C2) were measured to give the following results. The results provide confirmation that the coating film was transparent and yet exhibited heat insulating properties.

| | Sunlight Transmission (a) (%) | Visible Light Transmission (b) (%) | (a) − (b) (%) |
|---|---|---|---|
| II-1C1 | 70.22 | 71.00 | +0.78 |
| II-1C2 | 82.99 | 84.84 | +1.85 |
| glass plate (substrate) | 89.82 | 91.52 | −1.70 |

The coated article (II-3C) was hard, having a surface hardness of 6 (pencil hardness), and had a surface resistivity of $1 \times 10^9$ Ω per square, which indicates antistatic properties.

COMPARATIVE EXAMPLE II-1

A coating composition (II-R1) was prepared in the same manner as in Example II-1, except for replacing the dispersion (DI-1) as used in Example II-1 with the dispersion (DI-R1) obtained in Comparative Example I-1. The coating composition (II-R1) was applied and dried on the same glass substrate as used in the coating articles II-1 and II-2 in the same manner as for the coating articles II-1 and II-2 to obtain a coated article (II-R1C) having a 6.3 µm thick film containing ZnO fine particles. The resulting coated article (II-R1C) was effective in screening ultraviolet rays but exhibited no heat ray screening effect.

Figure 9:
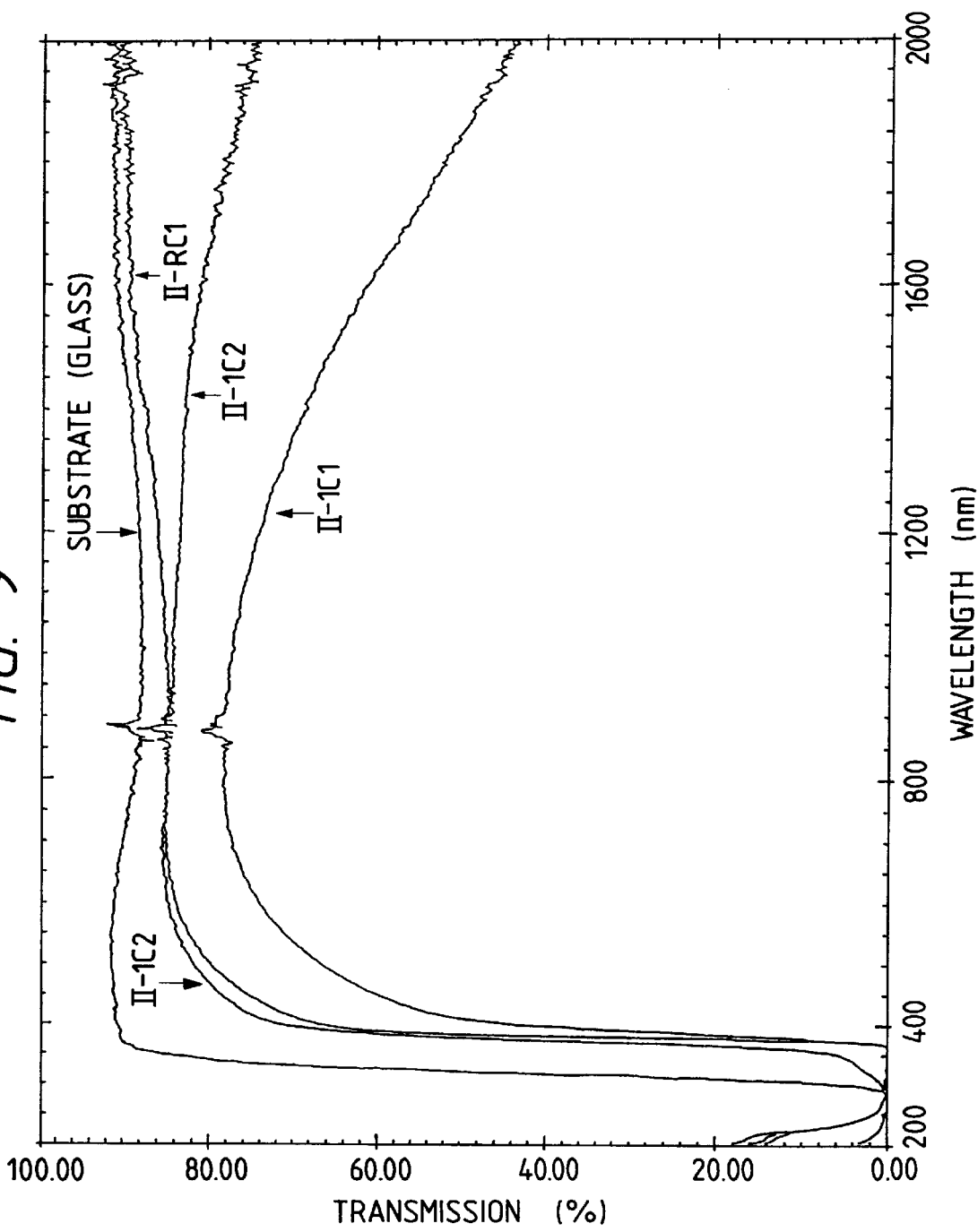
FIG. 9 shows spectral transmission curves of a coated article.

The spectral transmission curves of the coated articles (II-1C1) and (II-1C2) obtained in Examples and the coated article (II-R1C) obtained in Comparative Example (II-1) are shown in FIG. 9, in which the abscissa indicates the wavelength of incident light (nm), and the ordinate the transmission (%). The spectral transmission curve of the glass substrate is also shown in FIG. 9.

EXAMPLE II-5

In the same manner as in Example II-2, an aqueous dispersion (DI-2W) having finely dispersed therein 10 wt % of fine particles was prepared from the dispersion (DI-2) obtained in Example I-2.

A hundred parts by weight of the aqueous dispersion were mixed with 20 parts by weight of an acrylic resin emulsion (Acryset® ES-285E, produced by Nippon Shokubai Co., Ltd.; solids content: 50 wt %) as a binder to prepare a coating composition (II-5). Polyester fiber was soaked in the coating composition and dried to obtain polyester fiber having the fine particles at an add-on of 4.0 g/m². The resulting fiber was excellent in transparency while cutting ultraviolet rays and heat rays.

COMPARATIVE EXAMPLE II-5

In the same manner as in Example II-2, an aqueous dispersion having finely dispersed therein 10 wt % of fine particles was prepared from the dispersion (DI-R1) obtained in Comparative Example I-1.

A hundred parts by weight of the aqueous dispersion were mixed with 20 parts by weight of an acrylic resin emulsion (Acryset® ES-285E, produced by Nippon Shokubai Co., Ltd.; solids content: 50 wt %) as a binder resin to prepare a coating composition (II-R5). Polyester fiber was soaked in the coating composition and dried to obtain polyester fiber having the fine particles at an add-on of 4.2 g/m². The resulting fiber was excellent in transparency and cut ultraviolet rays but had no heat ray screening effect.

EXAMPLE II-6

In the same manner as in Example II-2, an aqueous dispersion (DI-2W) having finely dispersed therein 10 wt % of fine particles was prepared from the dispersion (DI-2) obtained in Example I-2.

A hundred parts by weight of the aqueous dispersion were mixed with 30 parts by weight of an acrylic resin emulsion (Acryset® ES-285E, produced by Nippon Shokubai Co., Ltd.; solids content: 50 wt %) as a binder resin to prepare a coating composition (II-5). Polyster fiber was soaked in the coating composition and dried to obtain polyester fiber having the fine particles at an add-on of 3.0 g/m². The resulting fiber was excellent in transparency while cutting ultraviolet rays and heat rays.

EXAMPLE II-7

Ten parts by weight of the powder (PI-2-1) obtained in Example 1-2 and 90 parts by weight of polypropylene (PP) pellets were melt-kneaded to obtain PP pellets (A) containing 10 wt % of the powder (PI-2-1).

A double-layered PP film was prepared using an extruder equipped with a feed block die for multilayer extrusion as follows. PP pellets (B) containing no fine particles were fed to the main extruder and melted at 220° C., while the PP pellets (A) were fed to the secondary extruder and melted at 180° C. Both resins were extruded while adjusting the extrusion rate of each extruder to obtain a laminate sheet composed of a PP (A) layer (powder-containing layer) and a PP (B) layer. The extruded laminate sheet was stretched to obtain an OPP film (biaxially stretched polypropylene film) composed of a 8 µm thick PP (A) layer and a 20 µm thick PP (B) layer.

The resulting film was a multilayer film having a thin layer (A) in which the fine particles were uniformly and highly dispersed, which was excellent in visible light transmitting properties while exhibiting excellent UV screening and heat ray screening properties.

EXAMPLE II-8

Fifty parts by weight of the powder (PI-6) obtained in Example I-6 and 50 parts by weight of polyethylene terephthalate (PTE) pellets were melt-kneaded to prepare PET pellets (A) containing 50 wt % of the powder (PI-6).

A double-layered PET film was prepared using the same extruders and stretching machine as used in Example II-7 as follows. PET pellets (B) containing no fine particles were fed to the main extruder and melted at 310° C., while the PET pellets (A) were fed to the secondary extruder and melted at 280° C. Both resins were extruded while adjusting the extrusion rate of each extruder to obtain a laminate sheet composed of a PET (A) layer (powder-containing layer) and a PET (B) layer. The extruded laminate sheet was stretched to obtain a PET film composed of a 2 µm thick PET (A) layer and a 20 µm thick PET (B) layer.

The resulting film was a multilayer film having a thin layer (A) in which the fine particles were uniformly and highly dispersed, which was excellent in visible light transmitting properties while exhibiting excellent UV screening and heat ray screening properties.

EXAMPLE II-9

The dispersion (DI-4) obtained in Example I-4 was concentrated in an evaporator under reduced pressure at a bath temperature of 130° C. to prepare a concentrated dispersion (DI-4C) having a particle concentration of 25 wt %.

A coating composition was prepared using an acrylic resin solution (Alloset 5858, produced by Nippon Shokubai Co., Ltd.; solid content: 60 wt %) as a binder component as follows.

Seventeen parts by weight of the acrylic resin solution, 40 parts by weight of the concentrated dispersion (DI-4C), and 23 parts by weight of n-butanol were mixed by stirring and dispersed in an ultrasonic homogenizer to prepare 80 parts by weight of a coating composition (II-9).

EXAMPLE II-10

In the same manner as in Example II-2, an aqueous dispersion (DI-4W) having finely dispersed therein 10 wt % of fine particles was prepared from the dispersion (DI-4) obtained in Example I-4.

To 100 parts by weight of an aqueous solution containing 10 wt % of a vinyl resin (Poval 205, produced by Kuraray Co., Ltd.) was added 100 parts by weight of the aqueous dispersion (DI-4W), followed by stirring. The mixture was dispersed in an ultrasonic homogenizer to obtain a coating composition (II-10).

EXAMPLE II-11

To 80 parts by weight of the concentrated dispersion (DI-4C) was added 150 parts by weight of the mixture (x)

while stirring, followed by stirring. The mixture was dispersed in an ultrasonic homogenizer to obtain a coating composition (II-11).

The resulting coating compositions (II-9) to (II-11) were applied to various substrates with a bar coater and dried to obtain coated articles (II-9C1), (II-9C2), (II-9C3), (II-9C4), and (II-4C), respectively.

The total transmission and haze of the substrates used are shown below.

| Substrate | Total Transmission (%) | Haze (%) |
|---|---|---|
| glass | 92 | <0.1 |
| PET | 89 | 2.0 |
| OPP | 88 | 3.2 |
| PC | 84 | 3.0 |

The film formation conditions, the thickness of the coating film, and the optical characteristics of the coated articles are shown in Table 12 below.

TABLE 12

| Coated Article | Coating Composition | Substrate | Drying Conditions | Film Thickness ($\mu$m) | Heat Ray Cut (2 $\mu$m) (%) | UV Cutting Power (Transmission) | Total Transmission (%) | Haze (%) |
|---|---|---|---|---|---|---|---|---|
| 9C1 | II-9 | glass | 80° C., 30 sec | 3.2 | 50 | A (0%) | 90 | 0.4 |
| 9C2 | II-9 | PET | " | 3.1 | 47 | A (1%) | 88 | 2.2 |
| 9C3 | II-9 | OPP | " | 3.3 | 52 | B (2%) | 84 | 4.0 |
| 9C4 | II-10 | PC | 120° C., 10 min | 2.5 | 40 | B (2%) | 82 | 3.5 |
| 4C | II-11 | PC | 200° C., 10 min | 4.0 | 55 | A (0%) | 90 | 0.4 |

EXAMPLE III-1

Five parts by weight of the powder (PI-6) obtained in Example I-6 and 995 parts by weight of polycarbonate resin pellets were mixed and melt-kneaded to obtain a molten mixture having uniformly dispersed therein 0.5 wt % of the fine particles. The composition was extruded to obtain a polycarbonate plate having a thickness of 2.0 mm. The resulting polycarbonate plate had highly dispersed therein the fine particles and exhibited excellent visible light transmitting properties, having a total transmission of 85% or higher, UV screening properties, and heat ray screening properties.

EXAMPLE III-2

Twenty-five parts by weight of the powder (PI-7) obtained in Example I-7 and 475 parts by weight of methacrylic resin pellets were mixed and melt-kneaded to obtain a molten composition having uniformly dispersed therein 5 wt % of the fine particles. The composition was extruded to obtain a methacrylic resin sheet having a thickness of 2 mm. The resulting sheet had highly dispersed therein the fine particles and had a total transmission of 83% and a haze of 86%, exhibiting high visible light transmitting properties and excellent diffuse transmitting properties, and also had excellent UV and heat ray screening effects.

COMPARATIVE EXAMPLE III-1

A 2 mm thick polycarbonate plate containing 0.5 wt % of fine particles was obtained in the same manner as in Example III-1, except for replacing the powder (PI-6) as used in Example III-1 with zinc oxide fine particles prepared by a French process (Aenka 1-Go, a product of Sakai Chemical Industry Co., Ltd.). The resulting polycarbonate plate was found to contain the fine particles non-uniformly in a secondarily agglomerated state. As compared with the one obtained in Example 111-1, the polycarbonate plate was white turbid, lacking transparency, and had a low UV screening effect. A heat ray screening effect was not observed.

EXAMPLE III-3

Two parts by weight of the powder (PI-6) obtained in Example I-6 and 98 parts by weight of polyester resin pellets were mixed and melt-kneaded to obtain a polyester composition having uniformly dispersed therein 2 wt % of the zinc oxide fine particles. The composition was extruded into a sheet, and the extruded sheet was stretched to obtain a polyester film having a thickness of 40 $\mu$m. The resulting film was a film having the fine particles uniformly and highly dispersed therein which was excellent in visible light transmitting properties, UV screening properties, and heat ray screening properties.

COMPARATIVE EXAMPLE III-2

A 40 $\mu$m thick polyester film containing 2 wt % of fine particles was obtained in the same manner as in Example III-3, except for replacing the powder (PI-6) as used in Example III-3 with zinc oxide fine particles prepared by a French process (Aenka 1-Go, a product of Sakai Chemical Industry Co., Ltd.). The resulting film was found to contain the fine particles in a secondarily agglomerated state and therefore had a low UV screening effect and was white turbid, lacking transparency. No heat ray screening effect was observed.

The section of the films obtained in Example III-3 and Comparative Example III-2 was observed through a transmission electron microscope. As a result, the film obtained in Example III-3 was a practically homogeneous film in which the fine particles were highly dispersed, whereas the film obtained in Comparative Example III-2 had a poor surface profile with coarse projections due to agglomeration of the fine particles. Besides, the film had insufficient abrasion resistance and scratch resistance on account of gaps between the fine particles and the PET matrix.

EXAMPLE III-4

A polyester composition containing 2 wt % of the powder (PI-6) was prepared in the same manner as in Example III-3. The resulting polyester composition was melt-spun to obtain polyester fiber. The fiber had uniformly and highly dispersed therein the fine particles and exhibited transparency and excellent UV and heat ray screening properties.

COMPARATIVE EXAMPLE III-3

Polyester fiber containing zinc oxide fine particles was obtained in the same manner as in Example III-4, except for replacing the powder (PI-6) as used in Example III-4 with zinc oxide fine particles prepared by a French process (Aenka 1-Go, a product of Sakai Chemical Industry Co., Ltd.). The resulting fiber was found to contain the fine particles in a secondarily agglomerated state and therefore had a low UV screening effect and was white turbid, lacking transparency. No heat ray screening effect was observed.

EXAMPLE IV-1

In the same manner as in Example II-2, an aqueous dispersion (DI-1W) having finely dispersed therein 10 wt % of fine particles was prepared from the dispersion (DI-1) obtained in Example I-1. A cosmetic (O/W type cream) containing the aqueous dispersion was prepared according to the following formulation.

Formulation:
Aqueous Phase:

| | |
|---|---|
| (a) Aqueous dispersion | 50 parts by weight |
| (b) Propylene glycol | 5 parts by weight |
| (c) Glycerin | 10 parts by weight |
| (d) Potassium hydroxide | 0.2 part by weight |

Oily Phase:

| | |
|---|---|
| (e) Cetanol | 5 parts by weight |
| (f) Liquid paraffin | 5 parts by weight |
| (g) Stearic acid | 3 parts by weight |
| (h) Isostearyl myristate | 2 parts by weight |
| (i) Glycerol monostearate | 2 parts by weight |

The components (a) to (d) were mixed by stirring to prepare an aqueous phase, which was kept at 80° C. The components (e) to (i) were mixed uniformly to prepare an oily phase, which was kept at 80° C. The oily phase was added to the aqueous phase, followed by stirring. The mixture was emulsified by means of a homomixer, followed by cooling to room temperature to obtain cream. The resulting cream was clear and yet excellent in UV screening effect and heat ray screening effect.

COMPARATIVE EXAMPLE IV-1

Cream was prepared in the same manner as in Example IV-1, except for replacing the aqueous dispersion (DI-1W) as used in Example IV-1 with 50 parts by weight of an aqueous dispersion containing 5 parts by weight of zinc oxide fine particles obtained by a French process (Aenka 1-Go, a product of Sakai Chemical Industry Co., Ltd.) in a concentration of 10 wt %.

The resulting cream had an insufficient UV screening effect on account of poor dispersion of the fine particles and was opaque with a high degree of whiteness. No heat ray screening properties was observed.

[Example of Paper Making]

EXAMPLE V-1

In the same manner as in Example II-2, an aqueous dispersion (DI-2W) having finely dispersed therein 10 wt % of fine particles was prepared from the dispersion (DI-2) obtained in Example I-2.

Separately, filter paper for quantitative determination (No. 5C, a product of Toyo Roshi K.K.) was beaten in a Niagara type beater to pulp having a C.S. freeness of 400 cc. The above prepared aqueous dispersion was added to the pulp to give a fine particle to pulp weight ratio of 1 wt %. The resulting pulp slurry was diluted to a solids content of 0.1 wt %, dehydrated in a TAPPI sheeting machine, and pressed to obtain a web having a basis weight of 75 g/m$^2$, which was then dried in a rotary drier at 100° C. to obtain paper containing 1 wt % of the fine particles. The fine particles being dispersed satisfactorily, the resulting paper had excellent UV screening properties, a heat ray screening effect, and excellent surface smoothness. Further, the paper hardly attracted dirt, etc.

COMPARATIVE EXAMPLE V-1

Paper was prepared in the same manner as in Example V-1, except for replacing the aqueous dispersion (DI-2W) as used in Example V-1 with an aqueous dispersion containing 10 wt % of zinc oxide fine particles obtained by a French process (Aenka 1-Go, a product of Sakai Chemical Industry Co., Ltd.). The resulting paper had a low UV screening effect due to secondary agglomeration of the fine particles. The surface conditions were poor with coarse projections due to the agglomerated particles. The paper had no heat ray screening properties and easily attracted dirt, etc.

Industrial Utility

The process for producing zinc oxide fine particles according to the present invention is a highly productive process, in which zinc oxide fine particles are obtained with controlled particle size, controlled particle shape, controlled surface conditions, and a controlled state of dispersion or agglomeration. The zinc oxide fine particles obtained by the process exhibit excellent functions and characteristics as fine particles, such as UV screening properties and transparency, and are therefore useful in coating compositions, coated articles, resin compositions, resin molded articles, paper, cosmetics, and the like.

The zinc oxide-polymer composite particles according to the present invention have UV screening power, controlled visible light transmitting properties and controlled light diffusing properties, and excellent dispersibility. They are useful in coating compositions, coated articles, resin compositions, resin molded articles, paper, cosmetics, diffusers for-back-lighting liquid crystal displays, and the like.

The inorganic compound particles according to the present invention have on the surface a cluster of thin plate like zinc oxide crystals whose tips project outward. Based on such unique geometrical characteristics not heretofore achieved, the particles exhibit abnormal light transmitting properties and can be used in coating compositions, coated articles, resin compositions, resin molded articles, paper, cosmetics, and the like to provide products having near infrared ray screening properties without impairing attractiveness and transparency of the products.

The zinc oxide-based particles according to the present invention mainly comprise zinc oxide endowed with heat ray screening properties and electrical conductivity in addition to excellent UV screening properties. Therefore, they can be used in coating compositions, coated articles, resin compositions, resin molded articles, paper, cosmetics, and the like to furnish products which exhibit excellent transparency, screen out ultraviolet rays and infrared rays, such as heat rays, and have controlled conductivity, such as antistatic properties.

What is claimed is:

1. Zinc oxide-based particles comprising a metal oxide co-precipitate containing, as a metallic component, at least one element additive selected from the group consisting of the group IIIB metal elements and the group IVB metal elements and zinc, having a zinc content of 80 to 99.9% in terms of the ratio of the number of zinc atoms to the total number of the atoms of said metallic components, and having X-ray crystallographically exhibiting zinc oxide crystalline properties.

2. Zinc oxide-based particles according to claim 1, wherein said element additive is indium and/or aluminum.

3. A cosmetic containing 0.1% by weight or more of the zinc oxide-based particles described in claim 1.

4. Zinc oxide-polymer composite particles which comprise zinc oxide fine particles and a polymer, the proportion of said zinc oxide fine particles being 50 to 99% by weight based on the total weight of said zinc oxide fine particles and said polymer, and the composite particles having an outer shell composed of a mixture and/or a composite of said zinc oxide fine particles and said polymer with the inside of said outer shell being hollow.

5. Composite particles comprising:
   (i) zinc oxide-based particles comprising a metal oxide co-precipitate containing, as a metallic component, (a) at least one element additive selected from the group consisting of metals of Group IIIB and metals of Group IVB, and (b) zinc, and having a zinc content of 80 to 99.9% in terms of the ratio of the number of zinc atoms to the total number of the atoms of said metallic components, and having X-ray crystallographically exhibiting zinc oxide crystalline properties, and (ii) a polymer.

6. Inorganic compound particles containing 60 to 100% by weight of zinc oxide and having on their surface a cluster of thin plate zinc oxide crystals with their tips projecting outward.

7. Inorganic compound particles according to claim 6, wherein said particles are hollow.

8. Inorganic compound particles according to claim 6, wherein said particles are porous.

9. Inorganic compound particles according to claim 6, wherein said zinc oxide crystals are thin plates having a flatness of 2 to 200.

10. Inorganic compound particles according to claim 9, wherein said thin plates have a major axis of 5 to 1,000 nm.

11. A cosmetic containing 0.1% by weight or more of the inorganic compound particles described in claim 6.

12. An antimicrobial agent comprising the inorganic compound particles described in claim 6.

13. An adsorbent comprising the inorganic compound particles described in claim 6.

14. A process for producing zinc oxide fine particles comprising:
    forming a mixture comprising a zinc source, a carboxyl-containing compound, and an alcohol, and
    heating said mixture to form said particles.

15. A process for producing zinc oxide fine particles according to claim 14, wherein said heating step is carried out in the presence of a compound additive containing one or more than one atomic group of at least one kind selected from the group consisting of a carboxyl group, an amino group, a quaternary ammonio group, an amido group, an imido bond, a hydroxyl group, a carboxylic acid ester bond, a urethane group, a urethane bond, a ureido group, a ureylene bond, an isocyanate group, an epoxy group, a phosphoric acid group, a metallic hydroxyl group, a metallic alkoxy group, and a sulfonic acid group in the molecule thereof and having a molecular weight of less than 1,000.

16. A process for producing zinc oxide fine particles according to claim 14, wherein said heating step is carried out in the presence of carbon dioxide and/or a carbonic acid source.

17. Zinc oxide fine particles produced by a process described in claim 14.

18. A process for producing zinc oxide-based particles comprising:
    forming a mixture comprising a zinc source, a carboxyl-containing compound, at least one element additive selected from the group consisting of the group IIIB metal elements and the group IVB metal elements, and an alcohol, and
    heating said mixture at a temperature of 100° C. or above to form said particles.

19. A process for producing zinc oxide-based particles according to claim 18, wherein said group IIIB metal element is indium and/or aluminum.

20. A process for producing inorganic compound particles having on their surface a cluster of zinc oxide crystals with their tip projecting outward, which comprises:
    forming a mixture comprising a zinc source, a carboxyl-containing compound, lactic acid or a compound thereof, and an alcohol, and
    heating said mixture at a temperature of 100° C. or above to form said particles.

21. A process for producing zinc oxide-polymer composite particles, which comprises:
    forming a mixture comprising a zinc source, a carboxyl-containing compound, a polymer, and an alcohol at a temperature of 1000 or above; and
    heating said mixture to form said particles.

* * * * *